(12) United States Patent
Church et al.

(10) Patent No.: US 12,305,226 B2
(45) Date of Patent: May 20, 2025

(54) BARCODED PROTEIN ARRAY FOR MULTIPLEX SINGLE-MOLECULE INTERACTION PROFILING

(71) Applicant: President and Fellows of Harvard College, Cambridge, MA (US)

(72) Inventors: George M. Church, Brookline, MA (US); Liangcai Gu, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 100 days.

(21) Appl. No.: 17/944,306

(22) Filed: Sep. 14, 2022

(65) Prior Publication Data

US 2023/0295704 A1  Sep. 21, 2023

Related U.S. Application Data

(63) Continuation of application No. 17/671,931, filed on Feb. 15, 2022, now abandoned, which is a continuation of application No. 17/361,508, filed on Jun. 29, 2021, now abandoned, which is a continuation of application No. 17/073,509, filed on Oct. 19, 2020, now abandoned, which is a continuation of application No. 15/128,145, filed as application No. PCT/US2015/022388 on Mar. 25, 2015, now Pat. No. 10,858,698.

(60) Provisional application No. 61/969,997, filed on Mar. 25, 2014.

(51) Int. Cl.
  *C12Q 1/6853* (2018.01)
  *C12Q 1/6806* (2018.01)
  *C12Q 1/6809* (2018.01)

(52) U.S. Cl.
  CPC ......... *C12Q 1/6853* (2013.01); *C12Q 1/6806* (2013.01); *C12Q 1/6809* (2013.01)

(58) Field of Classification Search
  CPC .. C12Q 1/6853; C12Q 1/6806; C12Q 1/6809; C12N 15/1065
  See application file for complete search history.

(56) References Cited

U.S. PATENT DOCUMENTS

| | | |
|---|---|---|
| 2002/0013003 A1 | 1/2002 | Wagner et al. |
| 2002/0127552 A1 | 9/2002 | Church et al. |
| 2005/0037397 A1 | 2/2005 | Mirkin et al. |
| 2005/0074898 A1 | 4/2005 | Datwani et al. |
| 2006/0040314 A1* | 2/2006 | Christians ............ C12Q 1/6837 435/6.11 |
| 2008/0003599 A1 | 1/2008 | Dary et al. |
| 2008/0171322 A1 | 7/2008 | Heyduk et al. |
| 2009/0018024 A1 | 1/2009 | Church et al. |
| 2009/0088329 A1 | 4/2009 | Brennan et al. |
| 2009/0105082 A1 | 4/2009 | Chetverin et al. |
| 2011/0143955 A1 | 6/2011 | Weiner |
| 2012/0277113 A1 | 11/2012 | Huang |
| 2012/0322978 A1 | 12/2012 | Huang |
| 2013/0143749 A1 | 6/2013 | Ghadessy et al. |
| 2013/0210031 A1 | 8/2013 | Boyer et al. |

FOREIGN PATENT DOCUMENTS

| | | |
|---|---|---|
| WO | 0168671 A1 | 9/2001 |
| WO | 2012019765 A1 | 2/2012 |

OTHER PUBLICATIONS

Yamaguchi et al.( "cDNA display: a novel screening method for functional disulfide-rich peptides by solid-phase synthesis and stabilization of mRNA-protein fusions." Nucleic acids research 37.16 (2009): 13 pages). (Year: 2009).*
Mitra et al.( Nucleic Acids Research 27.24 (1999): e34-e39). (Year: 1999).*
Hirsch et al.( "Easily reversible desthiobiotin binding to streptavidin, avidin, and other biotin-binding proteins: uses for protein labeling, detection, and isolation." Analytical biochemistry 308.2 (2002): 343-357). (Year: 2002).*
Tran et al. "A Universal DNA-Based Protein Detection System," Journal of American Chemical Society, Sep. 25, 2013 (Sep. 25, 2013), vol. 135, No. 38, pp. 14008-14011 and Supporting Information. entire document.
Yamaguchi et al. "cDNA display: a novel screening method for functional disulfide-rich peptides by solid-phase synthesis and stabilization of mRNA-protein fusions," Nucleic Acids Research, Jun. 15, 2009 (Jun. 15, 2009), vol. 37, No. 16, e108 {p. 1-13 for citations). entire document.
Mitra et al. "In situ localized amplification and contact replication of many individual DNA molecules," Nucleic Acids Research, Dec. 15, 1999 (Dec. 15, 1999), vol. 27, No. 24, e34 (p. 1-6 for citations). entire document.
Hirsch et al. "Easily reversible desthiobiotin binding to streptavidin, avidin, and other biotin-binding proteins: uses for protein labeling, detection, and isolation," Analytical Biochemistry, 2002, vol. 308, p. 343-357. entire document.
Pjanic et al. "Nuclear Factor I genomic binding associates with chromatin boundaries," BMC Genomics, Feb. 12, 2013 (Feb. 12, 2013), vol. 14, No. 99, pp. 1-18. entire document.

(Continued)

*Primary Examiner* — Sahana S Kaup
(74) *Attorney, Agent, or Firm* — Banner & Witcoff, Ltd.

(57) ABSTRACT

Methods for attaching barcodes to polypeptides are provided. Methods for detecting molecular interactions at the single molecule level are provided. Embodiments of the invention are directed to a ONA barcoded protein array technology for parallel protein interaction profiling on a single molecule basis. DNA barcodes are attached to proteins collectively via ribosome display or individually via enzymatic conjugation. Novel methods are described herein that measure protein interactions based on the statistical analysis of co-localized polonies arising from barcoding DNAs of interacting proteins.

10 Claims, 36 Drawing Sheets

Specification includes a Sequence Listing.

(56) References Cited

OTHER PUBLICATIONS

Gu et al. "Multiplex single-molecule interaction profiling of DNA-barcoded proteins," Nature, Sep. 21, 2014 (Sep. 21, 2014), vol. 515, pp. ~54-557 and Supplementary Information. entire document.

* cited by examiner

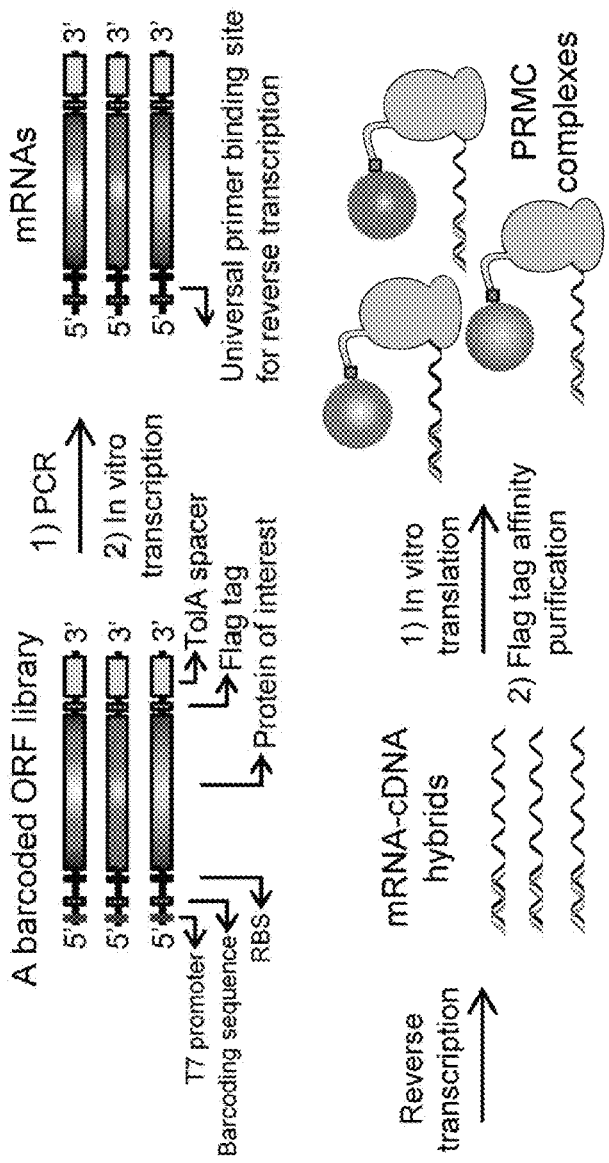
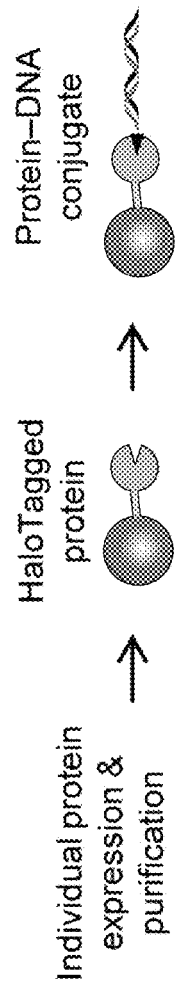
FIG. 1A
FIG. 1B

| Name | Details | Protein length (a. a.) | Observed polonies for different dilutions | | | | | | |
|------|---------|------------------------|------|------|------|------|------|------|------|
| | | | 10x | 100x | 1000x | 10,000x | 100,000x | 1000,000x |
| Scfv | Single-chain variable fragment (Oportuzumab) | 254 | 3,457,566 | 354,491 | 37,034 | 3,343 | 342 | 43 |
| | | | 3,783,673 | 384,958 | 40,638 | 3,595 | 415 | 41 |
| Nanobody | Single-domain antibody (Caplacizumab) | 260 | 3,139,771 | 319,974 | 33,354 | 2,932 | 394 | 31 |
| | | | 3,419,354 | 349,061 | 36,785 | 3,257 | 345 | 49 |
| Adnectin | Engineered the tenth fibronectin type III domain, CT-322 | 103 | 3,386,196 | 346,682 | 36,263 | 3,238 | 378 | 28 |
| | | | 3,722,036 | 379,665 | 39,761 | 3,745 | 391 | 30 |
| Affibody | Engineered Z domain of protein A, ABY-025 | 59 | 3,904,925 | 398,140 | 41,749 | 3,773 | 373 | 41 |
| | | | 4,307,520 | 440,476 | 45,790 | 4,335 | 509 | 25 |
| DARPin | Engineered ankyrin repeat proteins, MP0112 | 136 | 2,632,662 | 267,989 | 28,038 | 2,563 | 265 | 30 |
| | | | 2,893,576 | 295,016 | 30,697 | 2,990 | 327 | 25 |
| Anticalin | Engineered lipocalin, PRS-050 | 155 | 2,579,188 | 263,339 | 28,315 | 2,520 | 279 | 26 |
| | | | 2,830,314 | 289,320 | 30,149 | 2,704 | 269 | 46 |
| Knottin | Engineered cystine-knot miniprotein, 2.5D | 34 | 3,990,730 | 406,311 | 42,426 | 3,885 | 468 | 41 |
| | | | 4,407,769 | 448,907 | 47,177 | 4,174 | 452 | 26 |
| TUBEs | Tandem ubiquitin-binding entities, ubiquilin-1 | 252 | 2,311,215 | 235,068 | 24,739 | 2,339 | 288 | 18 |
| | | | 2,525,796 | 258,409 | 27,117 | 2,429 | 286 | 31 |
| HB36 | Computationally designed hemagglutinin binding protein | 93 | 2,391,775 | 242,272 | 25,598 | 2,322 | 255 | 37 |
| | | | 2,622,536 | 267,086 | 28,051 | 2,662 | 275 | 23 |
| GP120 | The outer domain of HIV envelope glycoprotein GP120 | 192 | 1,693,019 | 172,836 | 18,255 | 1,671 | 169 | 14 |
| | | | 1,854,037 | 188,939 | 19,322 | 1,878 | 182 | 10 |
| IFNB1 | Human interferon beta 1 | 166 | 1,396,290 | 142,750 | 15,082 | 1,390 | 151 | 8 |
| | | | 1,527,030 | 155,242 | 16,298 | 1,492 | 189 | 1 |
| Toxin A | Clostridium difficile toxin A receptor-binding domain | 1048 | 441,523 | 45,073 | 4,717 | 439 | 37 | 3 |
| | | | 461,514 | 47,540 | 4,784 | 364 | 46 | 1 |

| ScFv # | Original mAb | Construction method | Binding target |
|---|---|---|---|
| 1-20 | Anrukinzumab | V$_H$-linker-V$_L$ | IL13 |
| 21-40 | Ustekinumab | V$_H$-linker-V$_L$ | IL12B |
| 41-60 | Canakinumab | V$_H$-linker-V$_L$ | IL1B |
| 61-80 | Conatumumab | V$_H$-linker-V$_L$ | TNFRSF10B |
| 81-100 | Ibalizumab | V$_H$-linker-V$_L$ | CD4 |
| 101-120 | Oportuzumab | V$_H$-linker-V$_L$ | CD326 |
| 121-140 | Otelixizumab | V$_H$-linker-V$_L$ | CD3E |
| 141-160 | Ranibizumab | V$_H$-linker-V$_L$ | VEGFA |
| 161-180 | Siltuximab | V$_H$-linker-V$_L$ | IL6 |
| 181-200 | Tanezumab | V$_H$-linker-V$_L$ | NGF |

| Human protein # | Entrez Gene symbol | Entrez Gene ID | Protein length (a.a.) |
|---|---|---|---|
| 1 | IL1B | 3553 | 270 |
| 2 | IL2 | 3558 | 154 |
| 3 | IL3 | 3562 | 153 |
| 4 | IL4 | 3565 | 154 |
| 5 | IL6 | 3569 | 212 |
| 6 | IL7 | 3574 | 178 |
| 7 | IL8 | 3576 | 100 |
| 8 | IL9 | 3578 | 145 |
| 9 | IL10 | 3586 | 179 |
| 10 | IL12B | 3593 | 328 |
| 11 | IL13 | 3596 | 147 |
| 12 | IL15 | 3600 | 163 |
| 13 | IL17A | 3605 | 156 |
| 14 | IL17B | 27190 | 181 |
| 15 | IL17F | 112744 | 164 |
| 16 | IL18 | 3606 | 194 |
| 17 | IL20 | 50604 | 177 |
| 18 | IL25 | 64806 | 178 |
| 19 | IL26 | 55801 | 172 |
| 20 | IL28A | 282616 | 201 |
| 21 | IL29 | 282618 | 201 |
| 22 | IL31 | 386653 | 165 |
| 23 | CD1A | 909 | 312 |
| 24 | CD1E | 913 | 334 |
| 25 | CD3E | 916 | 208 |
| 26 | CD4 | 920 | 459 |
| 27 | CD7 | 924 | 241 |
| 28 | CD27 | 939 | 261 |
| 29 | CD38 | 952 | 301 |
| 30 | CD40 | 958 | 278 |
| 31 | CD52 | 1043 | 62 |
| 32 | CD58 | 965 | 241 |
| 33 | CD59 | 966 | 129 |
| 34 | CD79B | 974 | 230 |
| 35 | CD74 | 972 | 233 |
| 36 | CD80 | 941 | 289 |
| 37 | CD207 | 50489 | 329 |
| 38 | CD247 | 919 | 165 |
| 39 | CD274 | 29126 | 291 |
| 40 | CD302 | 9936 | 171 |
| 41 | CD320 | 51293 | 283 |
| 42 | CD326 | 4072 | 314 |
| 43 | CNTF | 1270 | 201 |
| 44 | CSF2 | 1437 | 145 |
| 45 | CSF3 | 1440 | 201 |
| 46 | NGF | 4803 | 241 |
| 47 | NODAL | 4838 | 348 |
| 48 | OSM | 5008 | 253 |
| 49 | THPO | 7066 | 350 |
| 50 | VEGFA | 7422 | 237 |
| 51 | FASLG | 356 | 282 |
| 52 | LTA | 4049 | 206 |
| 53 | TNF | 7124 | 234 |
| 54 | TNFRSF10B | 8795 | 440 |
| 55 | TNFRSF13B | 23495 | 248 |

| Raf-RBD | Ras (nM) | Total Raf-RBD polonies | Total Ras polonies | Colocalized Raf-RBD polonies | Mean of colocalization ratio (%) | Lower 95% CI of mean* | Upper 95% CI of mean* |
|---|---|---|---|---|---|---|---|
| WT | 20 | 2489 | 3276 | 89 | 3.532 | 2.696 | 4.368 |
| R59A | | 2859 | | 9 | 0.292 | 0.087 | 0.496 |
| N64A | | 2277 | | 21 | 0.920 | 0.478 | 1.361 |
| Q66A | | 2504 | | 7 | 0.281 | 0.073 | 0.489 |
| R67A | | 2239 | | 10 | 0.443 | 0.132 | 0.754 |
| T68A | | 1885 | | 10 | 0.463 | 0.183 | 0.744 |
| V69A | | 2835 | | 23 | 0.860 | 0.480 | 1.240 |
| K84A | | 2582 | | 7 | 0.246 | 0.066 | 0.427 |
| A85K | | 2600 | | 148 | 5.687 | 4.778 | 6.596 |
| WT | 200 | 2721 | 4556 | 465 | 17.080 | 15.420 | 18.750 |
| R59A | | 2795 | | 39 | 1.399 | 0.976 | 1.821 |
| N64A | | 2849 | | 150 | 5.316 | 4.490 | 6.141 |
| Q66A | | 3092 | | 24 | 0.759 | 0.411 | 1.107 |
| R67A | | 2420 | | 58 | 2.352 | 1.704 | 3.000 |
| T68A | | 1935 | | 69 | 3.565 | 2.743 | 4.388 |
| V69A | | 2356 | | 111 | 4.693 | 3.782 | 5.605 |
| K84A | | 2020 | | 9 | 0.414 | 0.091 | 0.737 |
| A85K | | 2614 | | 509 | 19.440 | 17.530 | 21.350 |
| WT | 2000 | 2211 | 6408 | 610 | 27.900 | 25.770 | 30.040 |
| R59A | | 2536 | | 245 | 9.732 | 8.457 | 11.010 |
| N64A | | 1915 | | 441 | 23.310 | 20.970 | 25.640 |
| Q66A | | 2677 | | 176 | 6.558 | 5.658 | 7.458 |
| R67A | | 2112 | | 274 | 12.730 | 11.310 | 14.150 |
| T68A | | 2296 | | 377 | 16.490 | 14.730 | 18.250 |
| V69A | | 2525 | | 475 | 18.440 | 16.860 | 20.030 |
| K84A | | 2566 | | 127 | 4.900 | 3.980 | 5.819 |
| A85K | | 2564 | | 673 | 26.180 | 24.260 | 28.100 |

Note:
* N=100

| Assay conditions | -arr2 (nM) | Total -arr2 polonies | Total ADRB2 polonies | Colocalized ADRB2 polonies | Mean of colocalization ratio (%) | Lower 95% CI of mean* | Upper 95% CI of mean* |
|---|---|---|---|---|---|---|---|
| GRK2 phosphorylated | 0.5 | 390 | 16841 | 33 | 0.195 | 0.131 | 0.259 |
| | 1 | 648 | | 73 | 0.439 | 0.333 | 0.545 |
| | 2.5 | 1186 | | 179 | 1.071 | 0.884 | 1.257 |
| | 5 | 1306 | | 207 | 1.238 | 1.080 | 1.396 |
| | 10 | 1425 | | 219 | 1.298 | 1.149 | 1.446 |
| | 15 | 1467 | | 248 | 1.485 | 1.320 | 1.649 |
| Non-phosphorylated | 0.5 | 574 | 17386 | 11 | 0.063 | 0.018 | 0.108 |
| | 1 | 733 | | 14 | 0.079 | 0.023 | 0.136 |
| | 2.5 | 1259 | | 28 | 0.160 | 0.106 | 0.214 |
| | 5 | 1583 | | 20 | 0.113 | 0.07 | 0.156 |
| | 10 | 1521 | | 37 | 0.214 | 0.155 | 0.274 |
| | 15 | 1446 | | 47 | 0.273 | 0.192 | 0.353 |

| Ligands | GPCR | Total -arr2 polonies | Total GPCR polonies | Colocalized GPCR polonies | Mean of colocalization ratio (%) | Lower 95% CI of mean* | Upper 95% CI of mean* |
|---|---|---|---|---|---|---|---|
| alprenolol | ADRB2 | 1356 | 16783 | 37 | 0.221 | 0.152 | 0.289 |
| pindolol | | 1626 | | 131 | 0.778 | 0.642 | 0.914 |
| isoproterenol | | 1513 | | 178 | 1.060 | 0.898 | 1.222 |
| atropine | | 1778 | | 41 | 0.248 | 0.181 | 0.315 |
| xanomeline | | 1787 | | 51 | 0.307 | 0.219 | 0.395 |
| carbachol | | 1530 | | 51 | 0.305 | 0.224 | 0.385 |
| alprenolol | CHRM1 | 1356 | 13077 | 76 | 0.590 | 0.446 | 0.734 |
| pindolol | | 1626 | | 61 | 0.465 | 0.349 | 0.581 |
| isoproterenol | | 1513 | | 72 | 0.552 | 0.437 | 0.667 |
| atropine | | 1778 | | 79 | 0.604 | 0.487 | 0.722 |
| xanomeline | | 1787 | | 128 | 0.974 | 0.819 | 1.129 |
| carbachol | | 1530 | | 225 | 1.729 | 1.477 | 1.981 |
| alprenolol | CHRM2 | 1356 | 16291 | 99 | 0.614 | 0.500 | 0.728 |
| pindolol | | 1626 | | 117 | 0.723 | 0.602 | 0.844 |
| isoproterenol | | 1513 | | 108 | 0.670 | 0.551 | 0.790 |
| atropine | | 1778 | | 137 | 0.849 | 0.691 | 1.008 |
| xanomeline | | 1787 | | 110 | 0.675 | 0.559 | 0.791 |
| carbachol | | 1530 | | 455 | 2.804 | 2.543 | 3.065 |

Note:
* N=50

| Expression vector | Protein name | DNA source | Construction method |
|---|---|---|---|
| pRD-NHA-SecM | Scfv | Gene synthesis | NdeI/HindIII |
| pRD-NHA-SecM | Nanobody | Gene synthesis | NdeI/HindIII |
| pRD-NHA-SecM | Adnectin | Gene synthesis | NdeI/HindIII |
| pRD-NHA-SecM | Affibody | Gene synthesis | NdeI/HindIII |
| pRD-NHA-SecM | DARPin | Gene synthesis | NdeI/HindIII |
| pRD-NHA-SecM | Anticalin | Gene synthesis | NdeI/HindIII |
| pRD-NHA-SecM | Knottin | Gene synthesis | NdeI/HindIII |
| pRD-NHA-SecM | TUBEs | Gene synthesis | NdeI/HindIII |
| pRD-NHA-SecM | HB36 | Gene synthesis | NdeI/HindIII |
| pRD-NHA-SecM | GP120 | Gene synthesis | NdeI/HindIII |
| pRD-NHA-SecM | IFNB1 | Gene synthesis | NdeI/HindIII |
| pRD-NHA-SecM | Toxin A | Clostridium difficile gDNA (ATCC) | NdeI/HindIII |
| pRD-NHA-SecM | DsRed | pDsRed2 (Clontech) | NdeI/SacI |
| pEco-NHalo-Chis | DsRed | pDsRed2 (Clontech) | NdeI/SacI |
| pEco-CHaloFlagHis | Ras | Gene synthesis | NdeI/SacI |
| pRD-NHA-SecM | Raf-RBD | Gene synthesis | NdeI/SacI |
| pRD-NHA-SecM | Raf-RBD_R59A | Gene synthesis | NdeI/SacI |
| pRD-NHA-SecM | Raf-RBD_N64A | Gene synthesis | NdeI/SacI |
| pRD-NHA-SecM | Raf-RBD_Q66A | Gene synthesis | NdeI/SacI |
| pRD-NHA-SecM | Raf-RBD_R67A | Gene synthesis | NdeI/SacI |
| pRD-NHA-SecM | Raf-RBD_T68A | Gene synthesis | NdeI/SacI |
| pRD-NHA-SecM | Raf-RBD_V69A | Gene synthesis | NdeI/SacI |
| pRD-NHA-SecM | Raf-RBD_K84A | Gene synthesis | NdeI/SacI |
| pRD-NHA-SecM | Raf-RBD_A85K | Gene synthesis | NdeI/SacI |
| pBac-NFlagHA | ADRB2 | Gene synthesis | NcoI/EcoRI |
| pBac-NFlagHA | CHRM1 | Gene synthesis | NcoI/EcoRI |
| pBac-NFlagHA | CHRM2 | Gene synthesis | NcoI/EcoRI |
| pEco-CHaloFlagHis | ARRB2 | Gene synthesis | NdeI/HindIII |
| pRD-NHA-SecM | ScFv_Anrukinzumab | Gene synthesis | NdeI/SacI |
| pRD-NHA-SecM | ScFv_Ustekinumab | Gene synthesis | NdeI/SacI |
| pRD-NHA-SecM | ScFv_Canakinumab | Gene synthesis | NdeI/SacI |
| pRD-NHA-SecM | ScFv_Conatumumab | Gene synthesis | NdeI/SacI |
| pRD-NHA-SecM | ScFv_Ibalizumab | Gene synthesis | NdeI/SacI |
| pRD-NHA-SecM | ScFv_Oportuzumab | Gene synthesis | NdeI/SacI |
| pRD-NHA-SecM | ScFv_Otelixizumab | Gene synthesis | NdeI/SacI |
| pRD-NHA-SecM | ScFv_Ranibizumab | Gene synthesis | NdeI/SacI |
| pRD-NHA-SecM | ScFv_Siltuximab | Gene synthesis | NdeI/SacI |
| pRD-NHA-SecM | ScFv_Tanezumab | Gene synthesis | NdeI/SacI |
| pEco-CSBPHis | ScFvs & mutants | Synthetic & random | NdeI/SacI |

FIG. 15 (Cont.)

| | | mutagenesis | |
|---|---|---|---|
| pIRES-CHaloFlagHis | IL1B | Gene synthesis | NdeI/XhoI |
| pIRES-CHaloFlagHis-Gateway | IL2 | hORFeome v8.1 | Gateway |
| pIRES-CHaloFlagHis-Gateway | IL3 | hORFeome v8.1 | Gateway |
| pIRES-CHaloFlagHis-Gateway | IL4 | hORFeome v8.1 | Gateway |
| pIRES-CHaloFlagHis | IL6 | Gene synthesis | NdeI/XhoI |
| pIRES-CHaloFlagHis-Gateway | IL7 | hORFeome v8.1 | Gateway |
| pIRES-CHaloFlagHis-Gateway | IL8 | hORFeome v8.1 | Gateway |
| pIRES-CHaloFlagHis-Gateway | IL9 | hORFeome v8.1 | Gateway |
| pIRES-CHaloFlagHis-Gateway | IL10 | hORFeome v8.1 | Gateway |
| pIRES-CHaloFlagHis | IL12B | Gene synthesis | NdeI/XhoI |
| pIRES-CHaloFlagHis | IL13 | Gene synthesis | NdeI/XhoI |
| pIRES-CHaloFlagHis-Gateway | IL15 | hORFeome v8.1 | Gateway |
| pIRES-CHaloFlagHis-Gateway | IL17A | hORFeome v8.1 | Gateway |
| pIRES-CHaloFlagHis-Gateway | IL17B | hORFeome v8.1 | Gateway |
| pIRES-CHaloFlagHis-Gateway | IL17F | hORFeome v8.1 | Gateway |
| pIRES-CHaloFlagHis-Gateway | IL18 | hORFeome v8.1 | Gateway |
| pIRES-CHaloFlagHis-Gateway | IL20 | hORFeome v8.1 | Gateway |
| pIRES-CHaloFlagHis-Gateway | IL25 | hORFeome v8.1 | Gateway |
| pIRES-CHaloFlagHis-Gateway | IL26 | hORFeome v8.1 | Gateway |
| pIRES-CHaloFlagHis-Gateway | IL28A | hORFeome v8.1 | Gateway |
| pIRES-CHaloFlagHis-Gateway | IL29 | hORFeome v8.1 | Gateway |
| pIRES-CHaloFlagHis-Gateway | IL31 | hORFeome v8.1 | Gateway |
| pIRES-CHaloFlagHis-Gateway | CD1A | hORFeome v8.1 | Gateway |
| pIRES-CHaloFlagHis-Gateway | CD1E | hORFeome v8.1 | Gateway |
| pIRES-CHaloFlagHis | CD3E | Gene synthesis | NdeI/XhoI |
| pIRES-CHaloFlagHis | CD4 | Gene synthesis | NdeI/XhoI |

FIG. 15 (Cont.)

| | | | |
|---|---|---|---|
| pIRES-CHaloFlagHis-Gateway | CD7 | hORFeome v8.1 | Gateway |
| pIRES-CHaloFlagHis-Gateway | CD27 | hORFeome v8.1 | Gateway |
| pIRES-CHaloFlagHis-Gateway | CD38 | hORFeome v8.1 | Gateway |
| pIRES-CHaloFlagHis-Gateway | CD40 | hORFeome v8.1 | Gateway |
| pIRES-CHaloFlagHis-Gateway | CD52 | hORFeome v8.1 | Gateway |
| pIRES-CHaloFlagHis-Gateway | CD58 | hORFeome v8.1 | Gateway |
| pIRES-CHaloFlagHis-Gateway | CD59 | hORFeome v8.1 | Gateway |
| pIRES-CHaloFlagHis-Gateway | CD79B | hORFeome v8.1 | Gateway |
| pIRES-CHaloFlagHis-Gateway | CD74 | hORFeome v8.1 | Gateway |
| pIRES-CHaloFlagHis-Gateway | CD80 | hORFeome v8.1 | Gateway |
| pIRES-CHaloFlagHis-Gateway | CD207 | hORFeome v8.1 | Gateway |
| pIRES-CHaloFlagHis-Gateway | CD247 | hORFeome v8.1 | Gateway |
| pIRES-CHaloFlagHis-Gateway | CD274 | hORFeome v8.1 | Gateway |
| pIRES-CHaloFlagHis-Gateway | CD302 | hORFeome v8.1 | Gateway |
| pIRES-CHaloFlagHis-Gateway | CD320 | hORFeome v8.1 | Gateway |
| pIRES-CHaloFlagHis | CD326 | Gene synthesis | NdeI/XhoI |
| pIRES-CHaloFlagHis-Gateway | CNTF | hORFeome v8.1 | Gateway |
| pIRES-CHaloFlagHis-Gateway | CSF2 | hORFeome v8.1 | Gateway |
| pIRES-CHaloFlagHis-Gateway | CSF3 | hORFeome v8.1 | Gateway |
| pIRES-CHaloFlagHis | NGF | Gene synthesis | NdeI/XhoI |
| pIRES-CHaloFlagHis-Gateway | NODAL | hORFeome v8.1 | Gateway |
| pIRES-CHaloFlagHis-Gateway | OSM | hORFeome v8.1 | Gateway |
| pIRES-CHaloFlagHis-Gateway | THPO | hORFeome v8.1 | Gateway |
| pIRES-CHaloFlagHis | VEGFA | Gene synthesis | NdeI/XhoI |
| pIRES-CHaloFlagHis-Gateway | FASLG | hORFeome v8.1 | Gateway |

FIG. 15 (Cont.)

| | | | |
|---|---|---|---|
| pIRES-CHaloFlagHis-Gateway | LTA | hORFeome v8.1 | Gateway |
| pIRES-CHaloFlagHis-Gateway | TNF | hORFeome v8.1 | Gateway |
| pIRES-CHaloFlagHis | TNFRSF10B | Gene synthesis | NdeI/XhoI |
| pIRES-CHaloFlagHis-Gateway | TNFRSF13B | hORFeome v8.1 | Gateway |

SEQUENCES OF EXPRESSION VECTORS:
pRD-NHA-SecM:
GGATCTCGATCCCGCGAAATTAATACGACTCACTATAGGGAATGATACGGCGACCACCGAGGGGGGGG
AGAGAATGAGGAACCCGGGAACAATGATGGAATCCCTAGGTTGGCTTACCAAAAATGAAGCTGATGAA
TACTCCCTCAAAGACAATTGTCAACCTTACTTGTCCATTCCTGAAGAAATATTATATTTATACAACTTACCC
ATAGAATCCTATTTACTAGGAAAGGAAAAGCCTCCTATTTATAAAAATTGGATAGAGCTTTCTCAACAAC
AGTGGAATATCAATGATAGAACAATTGCCGATTTATTAGATGGGGTCTTAATAATACCATCGTATGCCGT
CTTCTGCTTGTTCCCCTCTAGAAATAATTTTGTTTAACTTTAAGAAGGAGATATATCGATGGCCTACCCCT
ACGACGTGCCCGACTACGCCCTGGCCACCACCGCGATCGCCATGGAACATATGGCTAGCGAATTCGAGC
TCAAGCTTGGCGGCAGCGGCGGCGGCAGCGGCGGCGGCAGCGGCGATTATAAAGATGATGATGATAA
AGGCGGCGCGGGCAGCGGCGCGGGCAGCGGCAGCAGCACTAGTCAGAAGCAAGCTGAAGAGGCGGC
AGCGAAAGCGGCGGCAGATGCTAAAGCGAAGGCCGAAGCAGATGCTAAAGCTGCGGAAGAAGCAGCG
AAGAAAGCGGCTGCAGACGCAAAGAAAAAAGCAGAAGCAGAAGCCGCCAAAGCCGCAGCCGAAGCGC
AGAAAAAAGCCGAGGCAGCCGCTGCGGCACTGAAGAAGAAAGCGGAAGCGGCAGAAGCAGCTGCAG
CTGAAGCAAGAAAGAAAGCGGCAACTGAAGCTGCTGAAAAAGCCAAAGCAGAAGCTGAGAAGAAAGC
GGCTGCTGAAAAGGCTGCAGCTGATAAGAAAGCGGCAGCAGAGAAAGCTGCAGCCGACAAAAAAGCA
GCAGAAAAAGCGGCTGCTGAAAAGGCAGCAGCTGATAAGAAAGCAGCGGCAGAAAAAGCCGCCGCAG
ACAAAAAAGCGGCAGCGGCAAAAGCTGCAGCTGAAAAAGCCGCTGCAGCAAAAGCGGCCGCAGAGGC
AGATGATATTTTCGGTGAGCTGGCAAAATTCAGCACGCCCGTCTGGATAAGCCAGGCGCAAGGCATCCG
TGCTGGCCCTACCGCACACCTTACTGGTGTGCGGGAGCAACTAGCATAACCCCTTGGGGCCTCTAAACG
GGTCTTGAGGGGTTTTTTGGGATCCTCTAGAGTCGACCTGCAGGCATGCAAGCTGATCCGGCTGCTAAC
AAAGCCCGAAAGGAAGCTGAGTTGGCTGCTGCCACCGCTGAGCAATAACTAGCATAACCCCTTGGGGC
CTCTAAACGGGTCTTGAGGGGTTTTTTGCTGAAAGGAGGAACTATATCCGGTTCGCTTGCTGTCCATAAA
ACCGCCCAGTCTAGCTATCGCCATGTAAGCCCACTGCAAGCTACCTGCTTTCTCTTTGCGCTTGCGTTTTC
CCTTGTCCAGATAGCCCAGTAGCTGACATTCATCCGGGGTCAGCACCGTTTCTGCGGACTGGCTTTCTAC
GTGTTCCGCTTCCTTTAGCAGCCCTTGCGCCCTGAGTGCTTGCGGCAGCGTGAGCTTCAAAAGAATTGCC
AGCTGGGGCGCCCTCTGGTAAGGTTGGGAAGCCCTGCAAAGTAAACTGGATGGCTTTCTTGCCGCCAAG
GATCTGATGGCGCAGGGGATCAAGATCTGATCAAGAGACAGGATGACGGTCGTTTCGCATGCTTGAAC
AAGATGGATTGCACGCAGGTTCTCCGGCCGCTTGGGTGGAGAGGCTATTCGGCTATGACTGGGCACAA
CAGACAATCGGCTGCTCTGATGCCGCCGTGTTCCGGCTGTCAGCGCAGGGGCGCCCGGTTCTTTTTGTC
AAGACCGACCTGTCCGGTGCCCTGAATGAACTGCAGGACGAGGCAGCGCGGCTATCGTGGCTGGCCAC
GACGGGCGTTCCTTGCGCAGCTGTGCTCGACGTTGTCACTGAAGCGGGAAGGGACTGGCTGCTATTGG
GCGAAGTGCCGGGGCAGGATCTCCTGTCATCTCACCTTGCTCCTGCCGAGAAAGTATCCATCATGGCTG
ATGCAATGCGGCGGCTGCATACGCTTGATCCGGCTACCTGCCCATTCGACCACCAAGCGAAACATCGCA
TCGAGCGAGCACGCACTCGGATGGAAGCCGGTCTTGTCGATCAGGATGATCTGGACGAAGAGCATCAG
GGGCTCGCGCCAGCCGAACTGTTCGCCAGGCTCAAGGCGCGTATGCCGGATGGTGAGGATCTCGTCGT
GACTCATGGCGATGCCTGCTTGCCGAATATCATGGTGGAAAATGGCCGCTTTTCTGGATTCATCGACTGT
GGCCGGCTGGGTGTGGCGGACCGCTATCAGGACATAGCGTTGGCTACCCGTGATATTGCTGAAGAGCT
TGGCGGCGAATGGGCTGACCGCTTCCTCGTGCTTTACGGTATCGCCGCTCCCGATTCGCAGCGCATCGC
CTTCTATCGCCTTCTTGACGAGTTCTTCTGAGCGGGACTCTGGGGTTCGAAATGACCGACCAAGCGACGC

FIG. 16

```
CCAACCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCGTTCAGCCCGACCGCT
GCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGC
AGATTACGCGCAGAAAAAAAGGATTTCAAGAAGATCCTTTGATCTTTTCTACGGGGTCTGACGCTCAGT
GGAACGAAAACTCACGTTAAGGGATTTTGGTCATGAGATTATCAAAAAGGATCTTCACCTAGATCCTTTT
ATAGTCCGGAAATACAGGAACGCACGCTGGATGGCCCTTCGCTGGGATGGTGAAACCATGAAAAATGG
CAGCTTCAGTGGATTAAGTGGGGGTAATGTGGCCTGTACCCTCTGGTTGCATAGGTATTCATACGGTTA
AAATTTATCAGGCGCGATTGCGGCAGTTTTTCGGGTGGTTTGTTGCCATTTTTACCTGTCTGCTGCCGTG
ATCGCGCTGAACGCGTTTTAGCGGTGCGTACAATTAAGGGATTATGGTAAATCCACTTACTGTCTGCCCT
CGTAGCCATCGAGATAAACCGCAGTACTCCGGCCACGATGCGTCCGGCGTAGAGGATCGAGATCTTTTC
AGCCTGATACAGATTAAATCAGAACGCAGAAGCGGTCTGATAAAACAGAATTTGCCTGGCGGCAGTAG
CGCGGTGGTCCCACCTGACCCCATGCCGAACTCAGAAGTGAAACGCCGTAGCGCCGATGGTAGTGTGG
GGTCTCCCCATGCGAGAGTAGGGAACTGCCAGGCATCAAATAAAACGAAAGGCTCAGTCGAAAGACTG
GGCCTTTCGTTTTATCTGTTGTTTGTCGGTGAACGCTCTCCTGAGTAGGACAAATCCGCCGGGAGCGGAT
TTGAACGTTGCGAAGCAACGGCCCGGAGGGTGGCGGGCAGGACGCCCGCCATAAACTGCCAGGCATCA
AATTAAGCAGAAGGCCATCCTGACGGATGGCCTTTTTGCGTTTCTACAAACTCTTTTGTTTATTTTTCTAA
ATACATTCAAATATGTATCCGCTCAT (SEQ ID NO:1)
```
Note: A pFN18K (Promega) derivative containing a kanamycin resistance gene for ribosome display.

pEco-CSBP
```
AGATCTCGATCCCGCGAAATTAATACGACTCACTATAGGGGAATTGTGAGCGGATAACAATTCCCCTCTA
GAAATAATTTTGTTTAACTTTAAGAAGGAGATATACATATGGAATTCTTAATTAAGCTGCAGGAGCTCGT
CGACGCGGCCGCACTCGAGAAGCTTGGCGGCAGCGGCATGGACGAGAAGACCACCGGCTGGCGGGGC
GGCCACGTGGTGGAGGGCCTGGCCGGCGAGCTGGAGCAGCTGCGGGCCAGGCTGGAGCACCACCCTC
AGGGCCAGCGGGAGCCCGGCGGCAGCGGCCACCACCACCACCACCACTGAGCTGAGCAATAACTAGCA
TAACCCCTTGGGGCCTCTAAACGGGTCTTGAGGGGTTTTTTGCTGAAAGGAGGAACTATATCCGGATTG
GCGAATGGGACGCGCCCTGTAGCGGCGCATTAAGCGCGGCGGGTGTGGTGGTTACGCGCAGCGTGAC
CGCTACACTTGCCAGCGCCCTAGCGCCCGCTCCTTTCGCTTTCTTCCCTTCCTTTCTCGCCACGTTCGCCGG
CTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTT
GACGTTGGAGTCCACGTTCTTTAATAGTGGACTCTTGTTCCAAACTGGAACAACACTCAACCCTATCTCG
GTCTATTCTTTTGATTTATAAGGGATTTTGCCGATTTCGGCCTATTGGTTAAAAAATGAGCTGATTTAACA
AAAATTTAACGCGAATTTTAACAAAATATTAACGTTTACAATTTCAGGTGGCACTTTTCGGGGAAATGTG
```

FIG. 16 (Cont.)

```
CGCGGAACCCCTATTTGTTTATTTTTCTAAATACATTCAAATATGTATCCGCTCATGAATTAATTCTTAGAA
AAACTCATCGAGCATCAAATGAAACTGCAATTTATTCATATCAGGATTATCAATACCATATTTTGAAAAA
GCCGTTTCTGTAATGAAGGAGAAAACTCACCGAGGCAGTTCCATAGGATGGCAAGATCCTGGTATCGGT
CTGCGATTCCGACTCGTCCAACATCAATACAACCTATTAATTTCCCCTCGTCAAAAATAAGGTTATCAAGT
GAGAAATCACCATGAGTGACGACTGAATCCGGTGAGAATGGCAAAAGTTTATGCATTTCTTTCCAGACT
TGTTCAACAGGCCAGCCATTACGCTCGTCATCAAAATCACTCGCATCAACCAAACCGTTATTCATTCGTGA
TTGCGCCTGAGCGAGACGAAATACGCGATCGCTGTTAAAAGGACAATTACAAACAGGAATCGAATGCA
ACCGGCGCAGGAACACTGCCAGCGCATCAACAATATTTTCACCTGAATCAGGATATTCTTCTAATACCTG
GAATGCTGTTTTCCCGGGGATCGCAGTGGTGAGTAACCATGCATCATCAGGAGTACGGATAAAATGCTT
GATGGTCGGAAGAGGCATAAATTCCGTCAGCCAGTTTAGTCTGACCATCTCATCTGTAACATCATTGGCA
ACGCTACCTTTGCCATGTTTCAGAAACAACTCTGGCGCATCGGGCTTCCCATACAATCGATAGATTGTCG
CACCTGATTGCCCGACATTATCGCGAGCCCATTTATACCCATATAAATCAGCATCCATGTTGGAATTTAAT
CGCGGCCTAGAGCAAGACGTTTCCCGTTGAATATGGCTCATAACACCCCTTGTATTACTGTTTATGTAAG
CAGACAGTTTTATTGTTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCAAACAAAAAAA
CCACCGCTACCAGCGGTGGTTTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGGGTTTCGCCA
CCTCTGACTTGAGCGTCGATTTTTGTGATGCTCGTCAGGGGGCGGAGCCTATGGAAAAACGCCAGCAA
CGCGGCCTTTTTACGGTTCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAGCCGAACGACCGAGCG
CAGCGAGTCAGTGAGCGAGGAAGCGGAAGAGCGCCTGATGCGGTATTTTCTCCTTACGCATCTGTGCG
GTATTTCACACCGCATATATGGTGCACTCTCAGTACAATCTGCTCTGATGCCGCATAGTTAAGCCAGTAT
ACACTCCGCTATCGCTACGTGACTGGGTCATGGCTGCGCCCCGACACCCGCCAACACCCGCTGACGCGC
CCTGACGGGCTTGTCTGCTCCCGGCATCCGCTTACAGACAAGCTGTGACCGTCTCCGGGAGCTGCATGT
GTCAGAGGTTTTCACCGTCATCACCGAAACGCGCGAGGCAGCTGCGGTAAAGCTCATCAGCGTGGTCGT
GAAGCGATTCACAGATGTCTGCCTGTTCATCCGCGTCCAGCTCGTTGAGTTTCTCCAGAAGCGTTAATGT
CTGGCTTCTGATAAAGCGGGCCATGTTAAGGGCGGTTTTTTCCTGTTTGGTCACTGATGCCTCCGTGTAA
GGGGGATTTCTGTTCATGGGGGTAATGATACCGATGAAACGAGAGAGGATGCTCACGATACGGGTTAC
TGATGATGAACATGCCCGGTTACTGGAACGTTGTGAGGGTAAACAACTGGCGGTATGGATGCGGCGGG
ACCAGAGAAAAATCACTCAGGGTCAATGCCAGCGCTTCGTTAATACAGATGTAGGTGTTCCACAGGGTA
GCCAGCAGCATCCTGCGATGCAGATCCGGAACATAATGGTGCAGGGCGCTGACTTCCGCGTTTCCAGAC
TTTACGAAACACGGAAACCGAAGACCATTCATGTTGTTGCTCAGGTCGCAGACGTTTTGCAGCAGCAGT
CGCTTCACGTTCGCTCGCGTATCGGTGATTCATTCTGCTAACCAGTAAGGCAACCCCGCCAGCCTAGCCG
GGTCCTCAACGACAGGAGCACGATCATGCGCACCCGTGGGGCCGCCATGCCGGCGATAATGGCCTGCT
TCTCGCCGAAACGTTTGGTGGCGGGACCAGTGACGAAGGCTTGAGCGAGGGCGTGCAAGATTCCGAAT
```

FIG. 16 (Cont.)

ACCGCAAGCGACAGGCCGATCATCGTCGCGCTCCAGCGAAAGCGGTCCTCGCCGAAAATGACCCAGAG
CGCTGCCGGCACCTGTCCTACGAGTTGCATGATAAAGAAGACAGTCATAAGTGCGGCGACGATAGTCAT
GCCCCGCGCCCACCGGAAGGAGCTGACTGGGTTGAAGGCTCTCAAGGGCATCGGTCGAGATCCCGGTG
CCTAATGAGTGAGCTAACTTACATTAATTGCGTTGCGCTCACTGCCCGCTTTCCAGTCGGGAAACCTGTC
GTGCCAGCTGCATTAATGAATCGGCCAACGCGCGGGGAGAGGCGGTTTGCGTATTGGGCGCCAGGGTG
GTTTTTCTTTTCACCAGTGAGACGGGCAACAGCTGATTGCCCTTCACCGCCTGGCCCTGAGAGAGTTGCA
GCAAGCGGTCCACGCTGGTTTGCCCCAGCAGGCGAAAATCCTGTTTGATGGTGGTTAACGGCGGGATAT
AACATGAGCTGTCTTCGGTATCGTCGTATCCCACTACCGAGATATCCGCACCAACGCGCAGCCCGGACTC
GGTAATGGCGCGCATTGCGCCCAGCGCCATCTGATCGTTGGCAACCAGCATCGCAGTGGGAACGATGC
CCTCATTCAGCATTTGCATGGTTTGTTGAAAACCGGACATGGCACTCCAGTCGCCTTCCCGTTCCGCTATC
GGCTGAATTTGATTGCGAGTGAGATATTTATGCCAGCCAGCCAGACGCAGACGCGCCGAGACAGAACTT
AATGGGCCCGCTAACAGCGCGATTTGCTGGTGACCCAATGCGACCAGATGCTCCACGCCCAGTCGCGTA
CCGTCTTCATGGAGAAAATAATACTGTTGATGGGTGTCTGGTCAGAGACATCAAGAAATAACGCCGGA
ACATTAGTGCAGGCAGCTTCCACAGCAATGGCATCCTGGTCATCCAGCGGATAGTTAATGATCAGCCCA
CTGACGCGTTGCGCGAGAAGATTGTGCACCGCCGCTTTACAGGCTTCGACGCCGCTTCGTTCTACCATCG
ACACCACCACGCTGGCACCCAGTTGATCGGCGCGAGATTTAATCGCCGCGACAATTTGCGACGGCGCGT
GCAGGGCCAGACTGGAGGTGGCAACGCCAATCAGCAACGACTGTTTGCCCGCCAGTTGTTGTGCCACG
CGGTTGGGAATGTAATTCAGCTCCGCCATCGCCGCTTCCACTTTTTCCCGCGTTTTCGCAGAAACGTGGC
TGGCCTGGTTCACCACGCGGGAAACGGTCTGATAAGAGACACCGGCATACTCTGCGACATCGTATAACG
TTACTGGTTTCACATTCACCACCCTGAATTGACTCTCTTCCGGGCGCTATCATGCCATACCGCGAAAGGTT
TTGCGCCATTCGATGGTGTCCGGGATCTCGACGCTCTCCCTTATGCGACTCCTGCATTAGGAAGCAGCCC
AGTAGTAGGTTGAGGCCGTTGAGCACCGCCGCCGCAAGGAATGGTGCATGCAAGGAGATGGCGCCCA
ACAGTCCCCCGGCCACGGGGCCTGCCACCATACCCACGCCGAAACAAGCGCTCATGAGCCCGAAGTGGC
GAGCCCGATCTTCCCCATCGGTGATGTCGGCGATATAGGCGCCAGCAACCGCACCTGTGGCGCCGGTGA
TGCCGGCCACGATGCGTCCGGCGTAGAGGATCG (SEQ ID NO:2)

Note: A pET24b (Novagen) derivative containing a kanamycin resistance gene for E. coli expression of fusion proteins bearing a C-terminal SBP tag and His-tag.

pEco-CHaloFlagHis
AGATCTCGATCCCGCGAAATTAATACGACTCACTATAGGGGAATTGTGAGCGGATAACAATTCCCCTCTA
GAAATAATTTTGTTTAACTTTAAGAAGGAGATATACATATGGAATTCTTAATTAAGCTGCAGGAGCTCGT
CGACGCGGCCGCACTCGAGAAGCTTGGCGGCAGCGGCCAGAAGCAAGCTGAAGAGGCGGCAGCGAAA
GCGGCGGCAGATGCTAAAGCGAAGGCCGAAGCAGATGCTAAAGCTGCGGAAGAAGCAGCGAAGAAA
GCGGCTGCCGACGCAAAGAAAAAGCAGAAGCAGAAGCCGCCAAAGCCGCAGCCGAAGCGCAGAAAA
AAGCCGAGGCAGCCGCTGCGGCACTGAAGAAGAAAGCGGAAGCGGCAGAAGCAGCTGCCGCTGAAGC
AAGAAAGAAAGCGGCAACTGAAGGCGGCAGCGGCATGGCTGAGATCGGCACCGGTTTCCCCTTCGACC
CCCACTACGTGGAGGTGCTGGGTGAGCGTATGCACTACGTGGACGTGGGTCCCGTGACGGCACCCCC
GTGCTGTTCCTGCACGGTAACCCCACCTCCTCCTACGTGTGGCGTAACATCATCCCCACGTGGCTCCCAC
CCACCGTTGCATCGCTCCCGACCTGATCGGTATGGGTAAGTCCGACAAGCCCGACCTGGGTTACTTCTTC
GACGACCACGTGCGTTTCATGGACGCTTTCATCGAGGCTCTGGGTCTGGAGGAGGTGGTGCTGGTGATC
CACGACTGGGGTTCCGCTCTGGGTTTCCACTGGGCTAAGCGTAACCCCGAGCGTGTGAAGGGTATCGCT

FIG. 16 (Cont.)

```
TTCATGGAGTTCATCCGTCCCATCCCCACCTGGGACGAGTGGCCCGAGTTCGCTCGTGAGACCTTCCAGG
CTTTCCGTACCACCGACGTGGGTCGTAAGCTGATCATCGACCAGAACGTGTTCATCGAGGGCACCCTGC
CTATGGGTGTGGTGCGTCCCCTGACCGAGGTGGAGATGGACCACTACCGTGAGCCCTTCCTGAACCCCG
TGGACCGTGAGCCCCTGTGGCGTTTCCCCAACGAGCTGCCCATCGCTGGTGAGCCCGCTAACATCGTGG
CTCTGGTGGAGGAGTACATGGACTGGCTGCACCAGTCCCCCGTGCCCAAGCTGCTGTTCTGGGGCACCC
CCGGTGTGCTGATCCCCCCGCTGAGGCTGCTCGTCTGGCTAAGTCCCTGCCCAACTGCAAGGCTGTGG
ACATCGGTCCCGGTCTGAACCTGCTCCAGGAGGACAACCCCGACCTGATCGGTTCCGAGATCGCTCGTT
GGCTGTCCACCCTGGAGATTTCCGGTGGTGGTTCCGGTGATTATAAAGATGATGATGATAAAGGCGGCG
CGGGCCACCACCACCACCACCACTGAGCTGAGCAATAACTAGCATAACCCCTTGGGGCCTCTAAACGGG
TCTTGAGGGGTTTTTTGCTGAAAGGAGGAACTATATCCGGATTGGCGAATGGGACGCGCCTGTAGCG
GCGCATTAAGCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAGCTCTAAATCGG
GGGCTCCCTTTAGGGTTCCGATTTAGTGCTTTACGGCACCTCGACCCCAAAAAACTTGATTAGGGTGATG
GTTCACGTAGTGGGCCATCGCCCTGATAGACGGTTTTTCGCCCTTTGACGTTGGAGTCCACGTTCTTTAA
TAGTGGACTCTTGTTCCAAACTGGAACAACACTCAACCCTATCTCGGTCTATTCTTTTGATTTATAAGGGA
TTTTGCCGATTTCGGCCTATTGGTTAAAAAATGAGCTGATTTAACAAAAATTTAACGCGAATTTTAACAA
AATATTAACGTTTACAATTTCAGGTGGCACTTTTCGGGGAAATGTGCGCGGAACCCCTATTTGTTTATTTT
TCTAAATACATTCAAATATGTATCCGCTCATGAATTAATTCTTAGAAAAACTCATCGAGCATCAAATGAAA
CTGCAATTTATTCATATCAGGATTATCAATACCATATTTTGAAAAAGCCGTTTCTGTAATGAAGGAGAA
AACTCACCGAGGCAGTTCCATAGGATGGCAAGATCCTGGTATCGGTCTGCGATTCCGACTCGTCCAACA
TCAATACAACCTATTAATTTCCCCTCGTCAAAAATAAGGTTATCAAGTGAGAAATCACCATGAGTGACGA
CTGAATCCGGTGAGAATGGCAAAAGTTTATGCATTTCTTTCCAGACTTGTTCAACAGGCCAGCCATTACG
CTCGTCATCAAAATCACTCGCATCAACCAAACCGTTATTCATTCGTGATTGCGCCTGAGCGAGACGAAAT
ACGCGATCGCTGTTAAAAGGACAATTACAAACAGGAATCGAATGCAACCGGCGCAGGAACACTGCCAG
CGCATCAACAATATTTTCACCTGAATCAGGATATTCTTCTAATACCTGGAATGCTGTTTTCCCGGGGATCG
CAGTGGTGAGTAACCATGCATCATCAGGAGTACGGATAAAATGCTTGATGGTCGGAAGAGGCATAAAT
TCCGTCAGCCAGTTTAGTCTGACCATCTCATCTGTAACATCATTGGCAACGCTACCTTTGCCATGTTTCAG
AAACAACTCTGGCGCATCGGGCTTCCCATACAATCGATAGATTGTCGCACCTGATTGCCCGACATTATCG
CGAGCCCATTTATACCCATATAAATCAGCATCCATGTTGGAATTTAATCGCGGCCTAGAGCAAGACGTTT
CCCGTTGAATATGGCTCATAACACCCCTTGTATTACTGTTTATGTAAGCAGACAGTTTTATTGTTCATGAC
CAAAATCCCTTAACGTGAGTTTTCGTTCCACTGAGCGTCAGACCCCGTAGAAAAGATCAAAGGATCTTCT
TGAGATCCTTTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCAGATACCAA
ATACTGTCCTTCTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGTGCACACAGCCCAGCTTG
GAGCGAACGACCTACACCGAACTGAGATACCTACAGCGTGAGCTATGAGAAAGCGCCACGCTTCCCGA
AGGGAGAAAGGCGGACAGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACCTCTGACTTGAGCGTCGATTT
TTGTGATGCTCGTCAGGGGGCGGAGCCTATGGAAAAACGCCAGCAACGCGGCCTTTTTACGGTTCCT
G
```

FIG. 16 (Cont.)

```
GCCTTTTGCTGGCCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGTGAGCGAGGA
AGCGGAAGAGCGCCTGATGCGGTATTTTCTCCTTACGCATCTGTGCGGTATTTCACACCGCATATATGGT
GCACTCTCAGTACAATCTGCTCTGATGCCGCATAGTTAAGCCAGTATACACTCCGCTATCGCTACGTGAC
TGGGTCATGGCTGCGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTTTCACCGTCATCAC
CGAAACGCGCGAGGCAGCTGCGGTAAAGCTCATCAGCGTGGTCGTGAAGCGATTCACAGATGTCTGCC
TGTTCATCCGCGTCCAGCTCGTTGAGTTTCTCCAGAAGCGTTAATGTCTGGCTTCTGATAAAGCGGGCCA
TGTTAAGGGCGGTTTTTTCCTGTTTGGTCACTGATGCCTCCGTGTAAGGGGATTTCTGTTCATGGGGGT
AATGATACCGATGAAACGAGAGAGGATGCTCACGATACGGGTTACTGATGATGAACATGCCCGGTTACT
GGAACGTTGTGAGGGTAAACAACTGGCGGTATGGATGCGGCGGGACCAGAGAAAAATCACTCAGGGT
CAATGCCAGCGCTTCGTTAATACAGATGTAGGTGTTCCACAGGGTAGCCAGCAGCATCCTGCGATGCAG
ATCCGGAACATAATGGTGCAGGGCGCTGACTTCCGCGTTTCCAGACTTTACGAAACACGGAAACCGAAG
ACCATTCATGTTGTTGCTCAGGTCGCAGACGTTTTGCAGCAGCAGTCGCTTCACGTTCGCTCGCGTATCG
GTGATTCATTCTGCTAACCAGTAAGGCAACCCCGCCAGCCTAGCCGGGTCCTCAACGACAGGAGCACGA
TCATGCGCACCCGTGGGGCCGCCATGCCGGCGATAATGGCCTGCTTCTCGCCGAAACGTTGGTGGCGG
GACCAGTGACGAAGGCTTGAGCGAGGGCGTGCAAGATTCCGAATACCGCAAGCGACAGGCCGATCATC
GTCGCGCTCCAGCGAAAGCGGTCCTCGCCGAAAATGACCCAGAGCGCTGCCGGCACCTGTCCTACGAGT
TGCATGATAAAGAAGACAGTCATAAGTGCGGCGACGATAGTCATGCCCCGCGCCCACCGGAAGGAGCT
GACTGGGTTGAAGGCTCTCAAGGGCATCGGTCGAGATCCCGGTGCCTAATGAGTGAGCTAACTTACATT
AATTGCGTTGCGCTCACTGCCCGCTTTCCAGTCGGGAAACCTGTCGTGCCAGCTGCATTAATGAATCGGC
CAACGCGCGGGGAGAGGCGGTTTGCGTATTGGGCGCCAGGGTGGTTTTCTTTTCACCAGTGAGACGG
GCAACAGCTGATTGCCCTTCACCGCCTGGCCCTGAGAGAGTTGCAGCAAGCGGTCCACGCTGGTTTGCC
CCAGCAGGCGAAAATCCTGTTTGATGGTGGTTAACGGCGGGATATAACATGAGCTGTCTTCGGTATCGT
CGTATCCCACTACCGAGATATCCGCACCAACGCGCAGCCCGGACTCGGTAATGGCGCGCATTGCGCCCA
GCGCCATCTGATCGTTGGCAACCAGCATCGCAGTGGGAACGATGCCCTCATTCAGCATTTGCATGGTTTG
TTGAAAACCGGACATGGCACTCCAGTCGCCTTCCCGTTCCGCTATCGGCTGAATTTGATTGCGAGTGAGA
TATTTATGCCAGCCAGCCAGACGCAGACGCGCCGAGACAGAACTTAATGGGCCCGCTAACAGCGCGATT
TGCTGGTGACCCAATGCGACCAGATGCTCCACGCCCAGTCGCGTACCGTCTTCATGGGAGAAAATAATA
CTGTTGATGGGTGTCTGGTCAGAGACATCAAGAAATAACGCCGGAACATTAGTGCAGGCAGCTTCCACA
GCAATGGCATCCTGGTCATCCAGCGGATAGTTAATGATCAGCCCACTGACGCGTTGCGCGAGAAGATTG
TGCACCGCCGCTTTACAGGCTTCGACGCCGCTTCGTTCTACCATCGACACCACCACGCTGGCACCCAGTT
GATCGGCGCGAGATTTAATCGCCGCGACAATTTGCGACGGCGCGTGCAGGGCCAGACTGGAGGTGGCA
ACGCCAATCAGCAACGACTGTTTGCCCGCCAGTTGTTGTGCCACGCGGTTGGGAATGTAATTCAGCTCC
GCCATCGCCGCTTCCACTTTTTCCCGCGTTTTCGCAGAAACGTGGCTGGCCTGGTTCACCACGCGGGAAA
CGGTCTGATAAGAGACACCGGCATACTCTGCGACATCGTATAACGTTACTGGTTTCACATTCACCACCCT
GAATTGACTCTCTTCCGGGCGCTATCATGCCATACCGCGAAAGGTTTTGCGCCATTCGATGGTGTCCGGG
ATCTCGACGCTCTCCCTTATGCGACTCCTGCATTAGGAAGCAGCCCAGTAGTAGGTTGAGGCCGTTGAG
CACCGCCGCCGCAAGGAATGGTGCATGCAAGGAGATGGCGCCCAACAGTCCCCGGCCACGGGGCCTG
CCACCATACCCACGCCGAAACAAGCGCTCATGAGCCCGAAGTGGCGAGCCCGATCTTCCCCATCGGTGA
```

FIG. 16 (Cont.)

TGTCGGCGATATAGGCGCCAGCAACCGCACCTGTGGCGCCGGTGATGCCGGCCACGATGCGTCCGGCG
TAGAGGATCG (SEQ ID NO:3)
Note: A pET24b derivative containing a kanamycin resistance gene for E. coli expression of fusion proteins bearing a C-terminal TolA spacer, HaloTag, Flag and His-tag.
pEco-NHalo-CHis
GGATCTCGATCCCGCGAAATTAATACGACTCACTATAGGGAGACCACAACGGTTTCCCGAATTGTGAGC
GGATAACAATAGAAATAATTTTGTTTAACTTTAAGAAGGAGATATATCGATGGCAGAAATCGGTACTGG
CTTTCCATTCGACCCCCATTATGTGGAAGTCCTGGGCGAGCGCATGCACTACGTCGATGTTGGTCCGCG
CGATGGCACCCCTGTGCTGTTCCTGCACGGTAACCCGACCTCCTCCTACGTGTGGCGCAACATCATCCCGC
ATGTTGCACCGACCCATCGCTGCATTGCTCCAGACCTGATCGGTATGGGCAAATCCGACAAACCAGACCT
GGGTTATTTCTTCGACGACCACGTCCGCTTCATGGATGCCTTCATCGAAGCCCTGGGTCTGGAAGAGGTC
GTCCTGGTCATTCACGACTGGGGCTCCGCTCTGGGTTTCCACTGGGCCAAGCGCAATCCAGAGCGCGTC
AAAGGTATTGCATTTATGGAGTTCATCCGCCCTATCCCGACCTGGGACGAATGGCCAGAATTTGCCCGC
GAGACCTTCCAGGCCTTCCGCACCACCGACGTCGGCCGCAAGCTGATCATCGATCAGAACGTTTTTATCG
AGGGTACGCTGCCGATGGGTGTCGTCCGCCCGCTGACTGAAGTCGAGATGGACCATTACCGCGAGCCG
TTCCTGAATCCTGTTGACCGCGAGCCACTGTGGCGCTTCCCAAACGAGCTGCCAATCGCCGGTGAGCCA
GCGAACATCGTCGCGCTGGTCGAAGAATACATGGACTGGCTGCACCAGTCCCCTGTCCCGAAGCTGCTG
TTCTGGGGCACCCCAGGCGTTCTGATCCCACCGGCCGAAGCCGCTCGCCTGGCCAAAAGCCTGCCTAAC
TGCAAGGCTGTGGACATCGGCCCGGGTCTGAATCTGCTGCAAGAAGACAACCCGGACCTGATCGGCAG
CGAGATCGCGCGCTGGCTGTCGACGCTCGAGATTTCCGGCGAGCCAACCACTGAGGATCTGTACTTTCA
GAGCGATAACGCGATCGCCATGGAACATATGGCTAGCGAATTCGAGCTCAAGCTTCAGAAGCAAGCTG
AAGAGGCGGCAGCGAAAGCGGCGGCAGATGCTAAAGCGAAGGCCGAAGCAGATGCTAAAGCTGCGG
AAGAAGCAGCGAAGAAAGCGGCTGCAGACGCAAAGAAAAAAGCAGAAGCAGAAGCCGCCAAAGCCGC
AGCCGAAGCGCAGAAAAAAGCCGAGGCAGCCGCTGCGGCACTGAAGAAGAAAGCGGAAGCGGCAGA
AGCAGCTGCAGCTGAAGCAAGAAAGAAAGCGGCAACTGAAGCTGCTGAAAAAGCCAAAGCAGAAGCT
GAGAAGAAAGCGGCTGCTGAAAAGGCTGCAGCTGATAAGAAAGCGGCAGCAGAGAAAGCTGCAGCCG
ACAAAAAAGCAGCAGAAAAAGCGGCTGCTGAAAAGGCAGCAGCTGATAAGAAAGCAGCGGCAGAAAA
AGCCGCCGCAGACAAAAAAGCGGCAGCGGCAAAAGCTGCAGCTGAAAAAGCCGCTGCAGCAAAAGCG
GCCGCAGAGGCAGATGATATTTTCGGTGAGCTACACCACCACCACCACCACTGAGGATCCTCTAGAGTC
GACCTGCAGGCATGCAAGCTGATCCGGCTGCTAACAAAGCCCGAAAGGAAGCTGAGTTGGCTGCTGCC
ACCGCTGAGCAATAACTAGCATAACCCCTTGGGGCCTCTAAACGGGTCTTGAGGGGTTTTTTGCTGAAA
GGAGGAACTATATCCGGTTCGCTTGCTGTCCATAAAACCGCCCAGTCTAGCTATCGCCATGTAAGCCCAC
TGCAAGCTACCTGCTTTCTCTTTGCGCTTGCGTTTTCCCTTGTCCAGATAGCCCAGTAGCTGACATTCATC
CGGGGTCAGCACCGTTTCTGCGGACTGGCTTTCTACGTGTTCCGCTTCCTTTAGCAGCCCTTGCGCCCTG
AGTGCTTGCGGCAGCGTGAGCTTCAAAAGAATTGCCAGCTGGGGCGCCCTCTGGTAAGGTTGGGAAGC
CCTGCAAAGTAAACTGGATGGCTTTCTTGCCGCCAAGGATCTGATGGCGCAGGGGATCAAGATCTGATC
AAGAGACAGGATGACGGTCGTTTCGCATGCTTGAACAAGATGGATTGCACGCAGGTTCTCCGGCCGCTT
GGGTGGAGAGGCTATTCGGCTATGACTGGGCACAACAGACAATCGGCTGCTCTGATGCCGCCGTGTTCC
GGCTGTCAGCGCAGGGGCGCCCGGTTCTTTTTGTCAAGACCGACCTGTCCGGTGCCCTGAATGAACTGC
AGGACGAGGCAGCGCGGCTATCGTGGCTGGCCACGACGGGCGTTCCTTGCGCAGCTGTGCTCGACGTT

```
GTCACTGAAGCGGGAAGGGACTGGCTGCTATTGGGCGAAGTGCCGGGGCAGGATCTCCTGTCATCTCA
CCTTGCTCCTGCCGAGAAAGTATCCATCATGGCTGATGCAATGCGGCGGCTGCATACGCTTGATCCGGCT
ACCTGCCCATTCGACCACCAAGCGAAACATCGCATCGAGCGAGCACGCACTCGGATGGAAGCCGGTCTT
GTCGATCAGGATGATCTGGACGAAGAGCATCAGGGGCTCGCGCCAGCCGAACTGTTCGCCAGGCTCAA
GGCGCGTATGCCGGATGGTGAGGATCTCGTCGTGACTCATGGCGATGCCTGCTTGCCGAATATCATGGT
GGAAAATGGCCGCTTTTCTGGATTCATCGACTGTGGCCGGCTGGGTGTGGCGGACCGCTATCAGGACAT
AGCGTTGGCTACCCGTGATATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTGACGAGTTCTTCTGAGCGGGA
CTCTGGGGTTCGAAATGACCGACCAAGCGACGCCCAACCGGTATCAGCTCACTCAAAGGCGGTAATACG
GTTATCCACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCATCACAAAAATC
GACGCTCAAGTCAGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAGGATTTCAAGAAGAT
CCTTTGATCTTTTCTACGGGGTCTGACGCTCAGTGGAACGAAAACTCACGTTAAGGGATTTTGGTCATGA
GATTATCAAAAAGGATCTTCACCTAGATCCTTTTATAGTCCGGAAATACAGGAACGCACGCTGGATGGC
CCTTCGCTGGGATGGTGAAACCATGAAAAATGGCAGCTTCAGTGGATTAAGTGGGGTAATGTGGCCT
GTACCCTCTGGTTGCATAGGTATTCATACGGTTAAAATTTATCAGGCGCGATTGCGGCAGTTTTTCGGGT
GGTTTGTTGCCATTTTTACCTGTCTGCTGCCGTGATCGCGCTGAACGCGTTTTAGCGGTGCGTACAATTA
AGGGATTATGGTAAATCCACTTACTGTCTGCCCTCGTAGCCATCGAGATAAACCGCAGTACTCCGGCCAC
GATGCGTCCGGCGTAGAGGATCGAGATCTTTTCAGCCTGATACAGATTAAATCAGAACGCAGAAGCGGT
CTGATAAAACAGAATTTGCCTGGCGGCAGTAGCGCGGTGGTCCCACCTGACCCCATGCCGAACTCAGAA
GTGAAACGCCGTAGCGCCGATGGTAGTGTGGGGTCTCCCCATGCGAGAGTAGGGAACTGCCAGGCATC
AAATAAAACGAAAGGCTCAGTCGAAAGACTGGGCCTTTCGTTTATCTGTTGTTTGTCGGTGAACGCTCT
CCTGAGTAGGACAAATCCGCCGGGAGCGGATTTGAACGTTGCGAAGCAACGGCCCGGAGGGTGGCGG
GCAGGACGCCCGCCATAAACTGCCAGGCATCAAATTAAGCAGAAGGCCATCCTGACGGATGGCCTTTT
GCGTTTCTACAAACTCTTTTGTTTATTTTTCTAAATACATTCAAATATGTATCCGCTCAT (SEQ ID NO:4)
```

Note: A pFN18K derivative containing a kanamycin resistance gene for E. coli expression of fusion proteins bearing an N-terminal HaloTag and a C-terminal Histag.

pBac-NFlagHA
```
GACGCGCCCTGTAGCGGCGCATTAAGCGCGGCGGGTGTGGTGGTTACGCGCAGCGTGACCGCTACACT
TGCCAGCGCCCTAGCGCCCGCTCCTTTCGCTTTCTTCCCTTCCTTTCTCGCCACGTTCGCCGGCTTTCCCCG
TCAAGCTCTAAATCGGGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTCGCCCTTTGACGTTGG
AGTCCACGTTCTTTAATAGTGGACTCTTGTTCCAAACTGGAACAACACTCAACCCTATCTCGGTCTATTCT
```

```
TTTGATTTATAAGGGATTTTGCCGATTTCGGCCTATTGGTTAAAAAATGAGCTGATTTAACAAAAATTTAA
CGCGAATTTTAACAAAATATTAACGTTTACAATTTCAGGTGGCACTTTTCGGGGAAATGTGCGCGGAACC
CCTATTTGTTTATTTTTCTAAATACATTCAAATATGTATCCGCTCATGAGACAATAACCCTGATAAATGCTT
CAATAATATTGAAAAAGGAAGAGTATGAGTATTCAACATTTCCGTGTCGCCCTTATTCCCTTTTTTGCGGC
ATTTTGCCTTCCTGTTTTTGCTCACCCAGAAACGCTGGTGAAAGTAAAAGATGCTGAAGATCAGTTGGGT
GCACGAGTGGGTTACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTATTGACGCCGGGC
AAGAGCAACTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGATAACACTG
CGGCCAACTTACTTCTGACAACGATCGGAGGACCGAAGGAGCTAACCGCTTTTTTGCACAACATGGGGG
ATCATGTAACTCGCCTTGATCGTTGGGAACCGGAGCTGAATGAAGCCATACCAAACGACGAGCGTGACA
CCACGATGCCTGTAGCAATGGCAACAACGTTGCGCAAACTATTAACTGGCGAACTACTTACTCTAGCTTC
CCGGCAACAATTAATAGACTGGATGGAGGCGGATAAAGTTGCAGGACCACTTCTGCGCTCGGCCCTTCC
GGCTGGCTGGTTTATTGCTGATAAATCGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGCAAACAAAAAAACCACCGCTAC
CAGCGGTGGTTTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTCTGTAGCACCG
CCTACATACCTCGCTCTGCTAATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGAACGGGGGGTTCGTGCAC
ACAGCCCAGCTTGGAGCGAACGACCTACACCGAACTGAGATACCTACAGCGTGAGCATTGAGAAAGCG
CCACGCTTCCCGAAGGGAGAAAGGCGGACAGGTATCCGGTAAGCGGCAGGGTCGGAACAGGAGAGCG
CACGAGGGAGCTTCCAGGGGGAAACGCCTGGTATCTTTATAGTCCTGTCGGGTTTCGCCACCTCTGACTT
GAGCGTCGATTTTTGTGATGCTCGTCAGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCCTGATTCTGTGGA
TAACCGTATTACCGCCTTTGAGTGAGCTGATACCGCTCGCCGCAGCCGAACGACCGAGCGCAGCGAGTC
AGTGAGCGAGGAAGCGGAAGAGCGCCTGATGCGGTATTTTCTCCTTACGCATCTGTGCGGTATTTCACA
CCGCAGACCAGCCGCGTAACCTGGCAAAATCGGTTACGGTTGAGTAATAAATGGATGCCCTGCGTAAGC
GGGTGTGGCGGACAATAAAGTCTTAAACTGAACAAAATAGATCTAAACTATGACAATAAAGTCTTAAA
CTAGACAGAATAGTTGTAAACTGAAATCAGTCCAGTTATGCTGTGAAAAAGCATACTGGACTTTTGTTAT
GGCTAAAGCAAACTCTTCATTTTCTGAAGTGCAAATTGCCCGTCGTATTAAAGAGGGGCGTGGCCAAGG
GCATGGTAAAGACTATATTCGCGGCGTTGTGACAATTTACCGAACAACTCCGCGGCCGGGAAGCCGATC
TCGGCTTGAACGAATTGTTAGGTGGCGGTACTTGGGTCGATATCAAAGTGCATCACTTCTTCCCGTATGC
CCAACTTTGTATAGAGAGCCACTGCGGGATCGTCACCGTAATCTGCTTGCACGTAGATCACATAAGCACC
AAGCGCGTTGGCCTCATGCTTGAGGAGATTGATGAGCGCGGTGGCAATGCCCTGCCTCCGGTGCTCGCC
GGAGACTGCGAGATCATAGATATAGATCTCACTACGCGGCTGCTCAAACCTGGGCAGAACGTAAGCCG
CGAGAGCGCCAACAACCGCTTCTTGGTCGAAGGCAGCAAGCGCGATGAATGTCTTACTACGGAGCAAG
```

FIG. 16 (Cont.)

TTCCCGAGGTAATCGGAGTCCGGCTGATGTTGGGAGTAGGTGGCTACGTCTCCGAACTCACGACCGAAA
AGATCAAGAGCAGCCCGCATGGATTTGACTTGGTCAGGGCCGAGCCTACATGTGCGAATGATGCCCATA
CTTGAGCCACCTAACTTTGTTTTAGGGCGACTGCCCTGCTGCGTAACATCGTTGCTGCTGCGTAACATCG
TTGCTGCTCCATAACATCAAACATCGACCCACGGCGTAACGCGCTTGCTGCTTGGATGCCCGAGGCATA
GACTGTACAAAAAAACAGTCATAACAAGCCATGAAAACCGCCACTGCGCCGTTACCACCGCTGCGTTCG
GTCAAGGTTCTGGACCAGTTGCGTGAGCGCATACGCTACTTGCATTACAGTTTACGAACCGAACAGGCT
TATGTCAACTGGGTTCGTGCCTTCATCCGTTTCCACGGTGTGCGTCACCCGGCAACCTTGGGCAGCAGCG
AAGTCGAGGCATTTCTGTCCTGGCTGGCGAACGAGCGCAAGGTTTCGGTCTCCACGCATCGTCAGGCAT
GGCGGCCTTGCTGTTCTTCTACGGCAAGGTGCTGTGCACGGATCTGCCCTGGCTTCAGGAGATCGGAA
GACCTCGGCCGTCGCGGCGCTTGCCGGTGGTGCTGACCCCGGATGAAGTGGTTCGCATCCTCGGTTTTC
TGGAAGGCGAGCATCGTTTGTTCGCCCAGGACTCTAGCTATAGTTCTAGTGGTTGGCTACGTATACTCCG
GAATATTAATAGATCATGGAGATAATTAAAATGATAACCATCTCGCAAATAAATAAGTATTTTACTGTTTT
CGTAACAGTTTTGTAATAAAAAAACCTATAAATATTCCGGATTATTCATACCGTCCCACCATCGGGCGCG
GATCCTCGATGAAGACCATCATCGCTCTGTCCTACATCTTCTGCCTGGTGTTCGCTGACTACAAGGACGA
CGACGACGCTTCCTCCTACCCCTACGACGTGCCCGACTACGCTATGGCTGAGATCGGCACCGGTTTCCCC
TTCGACCCCCACTACGTGGAGGTGCTGGGTGAGCGTATGCACTACGTGGACGTGGGTCCCCGTGACGG
CACCCCCGTGCTGTTCCTGCACGGTAACCCCACCTCCTCCTACGTGTGGCGTAACATCATCCCCCACGTG
GCTCCCACCCACCGTTGCATCGCTCCCGACCTGATCGGTATGGGTAAGTCCGACAAGCCCGACCTGGGTT
ACTTCTTCGACGACCACGTGCGTTTCATGGACGCTTTCATCGAGGCTCTGGGTCTGGAGGAGGTGGTGC
TGGTGATCCACGACTGGGGTTCCGCTCTGGGTTTCCACTGGGCTAAGCGTAACCCCGAGCGTGTGAAGG
GTATCGCTTTCATGGAGTTCATCCGTCCCATCCCCACCTGGGACGAGTGGCCCGAGTTCGCTCGTGAGAC
CTTCCAGGCTTTCCGTACCACCGACGTGGGTCGTAAGCTGATCATCGACCAGAACGTGTTCATCGAGGG
CACCCTGCCTATGGGTGTGGTGCGTCCCCTGACCGAGGTGGAGATGGACCACTACCGTGAGCCCTTCCT
GAACCCCGTGGACCGTGAGCCCCTGTGGCGTTTCCCCAACGAGCTGCCCATCGCTGGTGAGCCCGCTAA
CATCGTGGCTCTGGTGGAGGAGTACATGGACTGGCTGCACCAGTCCCCCGTGCCCAAGCTGCTGTTCTG
GGGCACCCCCGGTGTGCTGATCCCCCCCGCTGAGGCTGCTCGTCTGGCTAAGTCCCTGCCCAACTGCAA
GGCTGTGGACATCGGTCCCGGTCTGAACCTGCTCCAGGAGGACAACCCCGACCTGATCGGTTCCGAGAT
CGCTCGTTGGCTGTCCACCCTGGAGATCTCCGGTGGTGGTTCCGGTGCCATGGAACATATGGCTAGCGA
ATTCAAAGGCCTACGTCGACGAGCTCACTAGTCGCGGCCGCTTTCGAATCTAGAGCCTGCAGTCTCGAG
GCATGCGGTACCAAGCTTGTCGAGAAGTACTAGAGGATCATAATCAGCCATACCACATTTGTAGAGGTT
TTACTTGCTTTAAAAAACCTCCCACACCTCCCCCTGAACCTGAAACATAAAATGAATGCAATTGTTGTTGT
TAACTTGTTTATTGCAGCTTATAATGGTTACAAATAAAGCAATAGCATCACAAATTTCACAAATAAAGCAT
TTTTTTCACTGCATTCTAGTTGTGGTTTGTCCAAACTCATCAATGTATCTTATCATGTCTGGATCTGATCAC
TGCTTGAGCCTAGGAGATCCGAACCAGATAAGTGAAATCTAGTTCCAAACTATTTTGTCATTTTTAATTTT
CGTATTAGCTTACGACGCTACACCCAGTTCCCATCTATTTTGTCACTCTTCCCTAAATAATCCTTAAAAACT
CCATTTCCACCCCTCCCAGTTCCCAACTATTTTGTCCGCCCACAGCGGGGCATTTTTCTTCCTGTTATGTTT
TTAATCAAACATCCTGCCAACTCCATGTGACAAACCGTCATCTTCGGCTACTTTTTCTCTGTCACAGAATG
AAAATTTTTCTGTCATCTCTTCGTTATTAATGTTTGTAATTGACTGAATATCAACGCTTATTTGCAGCCTGA
ATGGCGAATGG (SEQ ID NO:5)
Note: A pFastBac1 derivative containing ampicillin and gentamicin resistance genes for

FIG. 16 (Cont.)

Baculovirus expression of fusion proteins bearing an N-terminal signal peptide, Flag and HA tags, and HaloTag.
pIRES-CHaloFlagHis
TAATACGACTCACTATAGGGCGAATTAATTCCGGTTATTTTCCACCATATTGCCGTCTTTTGGCAATGTGA
GGGCCCGGAAACCTGGCCCTGTCTTCTTGACGAGCATTCCTAGGGGTCTTTCCCCTCTCGCCAAAGGAAT
GCAAGGTCTGTTGAATGTCGTGAAGGAAGCAGTTCCTCTGGAAGCTTCTTGAAGACAAACAACGTCTGT
AGCGACCCTTTGCAGGCAGCGGAACCCCCCACCTGGCGACAGGTGCCTCTGCGGCCAAAAGCCACGTGT
ATAAGATACACCTGCAAAGGCGGCACAACCCCAGTGCCACGTTGTGAGTTGGATAGTTGTGGAAAGAG
TCAAATGGCTCACCTCAAGCGTATTCAACAAGGGGCTGAAGGATGCCCAGAAGGTACCCCATTGTATGG
GATCTGATCTGGGGCCTCGGTGCACATGCTTTACATGTGTTTAGTCGAGGTTAAAAAACGTCTAGGCCCC
CCGAACCACGGGGACGTGGTTTTCCTTTGAAAAACACGATGATAATATGGCCACCACCCATATGGGATC
CGAATTCGATATCTTAATTAAGCTGCAGGAGCTCGTCGACGCGGCCGCACTCGAGCAGAAGCAAGCTGA
AGAGGCGGCAGCGAAAGCGGCGGCAGATGCTAAAGCGAAGGCCGAAGCAGATGCTAAAGCTGCGGA
AGAAGCAGCGAAGAAAGCGGCTGCCGACGCAAAGAAAAAAGCAGAAGCAGAAGCCGCCAAAGCCGCA
GCCGAAGCGCAGAAAAAAGCCGAGGCAGCCGCTGCGGCACTGAAGAAGAAAGCGGAAGCGGCAGAA
GCAGCTGCCGCTGAAGCAAGAAAGAAAGCGGCAACTGAAGGCGGCAGCGGCATGGCTGAGATCGGCA
CCGGTTTCCCCTTCGACCCCCACTACGTGGAGGTGCTGGGTGAGCGTATGCACTACGTGGACGTGGGTC
CCCGTGACGGCACCCCCGTGCTGTTCCTGCACGGTAACCCCACCTCCTCCTACGTGTGGCGTAACATCAT
CCCCCACGTGGCTCCCACCCACCGTTGCATCGCTCCCGACCTGATCGGTATGGGTAAGTCCGACAAGCCC
GACCTGGGTTACTTCTTCGACGACCACGTGCGTTTCATGGACGCTTTCATCGAGGCTCTGGGTCTGGAG
GAGGTGGTGCTGGTGATCCACGACTGGGGTTCCGCTCTGGGTTTCCACTGGGCTAAGCGTAACCCCGAG
CGTGTGAAGGGTATCGCTTTCATGGAGTTCATCCGTCCCATCCCCACCTGGGACGAGTGGCCCGAGTTC
GCTCGTGAGACCTTCCAGGCTTTCCGTACCACCGACGTGGGTCGTAAGCTGATCATCGACCAGAACGTG
TTCATCGAGGGCACCCTGCCTATGGGTGTGGTGCGTCCCCTGACCGAGGTGGAGATGGACCACTACCGT
GAGCCCTTCCTGAACCCCGTGGACCGTGAGCCCCTGTGGCGTTTCCCCAACGAGCTGCCCATCGCTGGT
GAGCCCGCTAACATCGTGGCTCTGGTGGAGGAGTACATGGACTGGCTGCACCAGTCCCCCGTGCCCAAG
CTGCTGTTCTGGGGCACCCCCGGTGTGCTGATCCCCCCGCTGAGGCTGCTCGTCTGGCTAAGTCCCTGC
CCAACTGCAAGGCTGTGGACATCGGTCCCGGTCTGAACCTGCTCCAGGAGGACAACCCCGACCTGATCG
GTTCCGAGATCGCTCGTTGGCTGTCCACCCTGGAGATTTCCGGTGGTGGTTCCGGTGATTATAAAGATG
ATGATGATAAAGGCGGCGCGGGCCACCACCACCACCACCACTGAGATCTGACTGAAAAAAAAAAAAAA
AAAAAAAAAAAAAAAGTTTAAACACTAGTCCGCTGAGCAATAACTAGCATAACCCCTTGGGGCCTCTA
AACGGGTCTTGAGGGGTTTTTTGCTGAAAGGAGGAACTATATCCGGGCTTCCTCGCTCACTGACTCGCT
GCGCTCGGTCGTTCGGCTGCGGCGAGCGGTATCAGCTCACTCAAAGGCGGTAATACGGTTATCCACAGA
ATCAGGGGATAACGCAGGAAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACA

FIG. 16 (Cont.)

```
GAGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGTTGCCGGGAAGCTAGA
GTAAGTAGTTCGCCAGTTAATAGTTTGCGCAACGTTGTTGCCATTGCTACAGGCATCGTGGTGTCACGCT
CGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATGCTTTTCTGTGACTG
GTGAGTACTCAACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGTTCTTCGGGGC
GAAAACTCTCAAGGATCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATTGAAGCATTTAT
CAGGGTTATTGTCTCATGAGCGGATACATATTTGAATGTATTTAGAAAAATAAACAAATAGGGGTTCCG
CGCACATTTCCCCGAAAAGTGCCACCTGACGTCTAAGAAACCATTATTATCATGACATTAACCTATAAAA
ATAGGCGTATCACGAGGCCCTTTCGTCTCGCGCGTTTCGGTGATGACGGTGAAAACCTCTGACACATGC
AGCTCCCGGAGACGGTCACAGCTTGTCTGTAAGCGGATGCCGGGAGCAGACAAGCCCGTCAGGGCGCG
TCAGCGGGTGTTGGCGGGTGTCGGGCTGGCTTAACTATGCGGCATCAGAGCAGATTGTACTGAGAGT
GCACCATATATGCGGTGTGAAATACCGCACAGATGCGTAAGGAGAAAATACCGCATCAGGAAATTGTA
AACGTTAATATTTTGTTAAAATTCGCGTTAAATTTTTGTTAAATCAGCTCATTTTTTAACCAATAGGCCGA
AATCGGCAAAATCCCTTATAAATCAAAAGAATAGACCGAGATAGGGTTGAGTGTTGTTCCAGTTTGGAA
CAAGAGTCCACTATTAAAGAACGTGGACTCCAACGTCAAAGGGCGAAAAACCGTCTATCAGGGCGATG
GCCCACTACGTGAACCATCACCCTAATCAAGTTTTTTGGGGTCGAGGTGCCGTAAAGCACTAAATCGGA
ACCCTAAAGGGAGCCCCCGATTTAGAGCTTGACGGGGAAAGCCGGCGAACGTGGCGAGAAAGGAAGG
GAAGAAAGCGAAAGGAGCGGGCGCTAGGGCGCTGGCAAGTGTAGCGGTCACGCTGCGCGTAACCACC
ACACCCGCCGCGCTTAATGCGCCGCTACAGGGCGCGTCGCGCCATTCGCCATTCAGGCTGCGCAACTGT
TGGGAAGGGCGATCGGTGCGGGCCTCTTCGCTATTACGCCAGCTGGCGAAAGGGGGATGTGCTGCAAG
GCGATTAAGTTGGGTAACGCCAGGGTTTTCCCAGTCACGACGTTGTAAAACGACGGCCAGTGAATTG
(SEQ ID NO:6)
```

Note: A pT7CFE1 (Thermo Scientific) derivative containing a multiple cloning site, an ampicillin resistance gene for human IVT expression of fusion proteins bearing a C-terminal TolA spacer, HaloTag, Flag and His-tags.

pIRES-CHaloFlagHis-Gateway

```
TAATACGACTCACTATAGGGCGAATTAATTCCGGTTATTTTCCACCATATTGCCGTCTTTTGGCAATGTGA
GGGCCCGGAAACCTGGCCCTGTCTTCTTGACGAGCATTCCTAGGGGTCTTTCCCCTCTCGCCAAAGGAAT
```

FIG. 16 (Cont.)

```
GCAAGGTCTGTTGAATGTCGTGAAGGAAGCAGTTCCTCTGGAAGCTTCTTGAAGACAAACAACGTCTGT
AGCGACCCTTTGCAGGCAGCGGAACCCCCCACCTGGCGACAGGTGCCTCTGCGGCCAAAAGCCACGTGT
ATAAGATACACCTGCAAAGGCGGCACAACCCCAGTGCCACGTTGTGAGTTGGATAGTTGTGGAAAGAG
TCAAATGGCTCACCTCAAGCGTATTCAACAAGGGGCTGAAGGATGCCCAGAAGGTACCCCATTGTATGG
GATCTGATCTGGGGCCTCGGTGCACATGCTTTACATGTGTTTAGTCGAGGTTAAAAAACGTCTAGGCCCC
CCGAACCACGGGGACGTGGTTTTCCTTTGAAAAACACGATGATAATATGGCCACCACCCATATGGGAAC
AAGTTTGTACAAAAAAGCTGAACGAGAAACGTAAAATGATATAAATATCAATATATTAAATTAGATTTTG
CATAAAAAACAGACTACATAATACTGTAAAACACAACATATCCAGTCACTATGGCGGCCGCATTAGGCA
CCCCAGGCTTTACACTTTATGCTTCCGGCTCGTATAATGTGTGGATTTTGAGTTAGGATCCGTCGAGATTT
TCAGGAGCTAAGGAAGCTAAAATGGAGAAAAAAATCACTGGATATACCACCGTTGATATATCCCAATGG
CATCGTAAAGAACATTTTGAGGCATTTCAGTCAGTTGCTCAATGTACCTATAACCAGACCGTTCAGCTGG
ATATTACGGCCTTTTTAAAGACCGTAAAGAAAAATAAGCACAAGTTTTATCCGGCCTTTATTCACATTCTT
GCCCGCCTGATGAATGCTCATCCGGAATTCCGTATGGCAATGAAAGACGGTGAGCTGGTGATATGGGAT
AGTGTTCACCCTTGTTACACCGTTTTCCATGAGCAAACTGAAACGTTTTCATCGCTCTGGAGTGAATACCA
CGACGATTTCCGGCAGTTTCTACACATATATTCGCAAGATGTGGCGTGTTACGGTGAAAACCTGGCCTAT
TTCCCTAAAGGGTTTATTGAGAATATGTTTTTCGTCTCAGCCAATCCCTGGGTGAGTTTCACCAGTTTTGA
TTTAAACGTGGCCAATATGGACAACTTCTTCGCCCCCGTTTTCACCATGGGCAAATATTATACGCAAGGC
GACAAGGTGCTGATGCCGCTGGCGATTCAGGTTCATCATGCCGTTTGTGATGGCTTCCATGTCGGCAGA
ATGCTTAATGAATTACAACAGTACTGCGATGAGTGGCAGGGCGGGGCGTAAACGCGTGGATCCGGCTT
ACTAAAAGCCAGATAACAGTATGCGTATTTGCGCGCTGATTTTTGCGGTATAAGAATATATACTGATATG
TATACCCGAAGTATGTCAAAAAGAGGTATGCTATGAAGCAGCGTATTACAGTGACAGTTGACAGCGACA
GCTATCAGTTGCTCAAGGCATATATGATGTCAATATCTCCGGTCTGGTAAGCACAACCATGCAGAATGAA
GCCCGTCGTCTGCGTGCCGAACGCTGGAAAGCGGAAAATCAGGAAGGGATGGCTGAGGTCGCCCGGTT
TATTGAAATGAACGGCTCTTTTGCTGACGAGAACAGGGGCTGGTGAAATGCAGTTTAAGGTTTACACCT
ATAAAAGAGAGAGCCGTTATCGTCTGTTTGTGGATGTACAGAGTGATATTATTGACACGCCCGGGCGAC
GGATGGTGATCCCCCTGGCCAGTGCACGTCTGCTGTCAGATAAAGTCTCCCGTGAACTTTACCCGGTGGT
GCATATCGGGGATGAAAGCTGGCGCATGATGACCACCGATATGGCCAGTGTGCCGGTCTCCGTTATCGG
GGAAGAAGTGGCTGATCTCAGCCACCGCGAAAATGACATCAAAAACGCCATTAACCTGATGTTCTGGGG
AATATAAATGTCAGGCTCCCTTATACACAGCCAGTCTGCAGGTCGACCATAGTGACTGGATATGTTGTGT
TTTACAGTATTATGTAGTCTGTTTTTTATGCAAAATCTAATTTAATATATTGATATTTATATCATTTTACGTT
TCTCGTTCAGCTTTCTTGTACAAAGTGGTGCTCGAGCAGAAGCAAGCTGAAGAGGCGGCAGCGAAAGC
GGCGGCAGATGCTAAAGCGAAGGCCGAAGCAGATGCTAAAGCTGCGGAAGAAGCAGCGAAGAAAGC
GGCTGCCGACGCAAAGAAAAAGCAGAAGCAGAAGCCGCCAAAGCCGCAGCCGAAGCGCAGAAAAAA
GCCGAGGCAGCCGCTGCGGCACTGAAGAAGAAAGCGGAAGCGGCAGAAGCAGCTGCCGCTGAAGCAA
GAAAGAAAGCGGCAACTGAAGGCGGCAGCGGCATGGCTGAGATCGGCACCGGTTTCCCCTTCGACCCC
CACTACGTGGAGGTGCTGGGTGAGCGTATGCACTACGTGGACGTGGGTCCCGTGACGGCACCCCGT
GCTGTTCCTGCACGGTAACCCCACCTCCTCCTACGTGTGGCGTAACATCATCCCCACGTGGCTCCCACCC
ACCGTTGCATCGCTCCCGACCTGATCGGTATGGGTAAGTCCGACAAGCCCGACCTGGGTTACTTCTTCGA
CGACCACGTGCGTTTCATGGACGCTTTCATCGAGGCTCTGGGTCTGGAGGAGGTGGTGCTGGTGATCCA
CGACTGGGGTTCCGCTCTGGGTTTCCACTGGGCTAAGCGTAACCCCGAGCGTGTGAAGGGTATCGCTTT
```

FIG. 16 (Cont.)

```
CATGGAGTTCATCCGTCCCATCCCCACCTGGGACGAGTGGCCCGAGTTCGCTCGTGAGACCTTCCAGGCT
TTCCGTACCACCGACGTGGGTCGTAAGCTGATCATCGACCAGAACGTGTTCATCGAGGGCACCCTGCCT
ATGGGTGTGGTGCGTCCCCTGACCGAGGTGGAGATGGACCACTACCGTGAGCCCTTCCTGAACCCCGTG
GACCGTGAGCCCCTGTGGCGTTTCCCCAACGAGCTGCCCATCGCTGGTGAGCCCGCTAACATCGTGGCT
CTGGTGGAGGAGTACATGGACTGGCTGCACCAGTCCCCCGTGCCCAAGCTGCTGTTCTGGGGCACCCCC
GGTGTGCTGATCCCCCCCGCTGAGGCTGCTCGTCTGGCTAAGTCCCTGCCCAACTGCAAGGCTGTGGAC
ATCGGTCCCGGTCTGAACCTGCTCCAGGAGGACAACCCCGACCTGATCGGTTCCGAGATCGCTCGTTGG
CTGTCCACCCTGGAGATTTCCGGTGGTGGTTCCGGTGATTATAAAGATGATGATGATAAAGGCGGCGCG
GGCCACCACCACCACCACCACTGAGATCTGACTGAAAAAAAAAAAAAAAAAAAAAAAAAAAAAAAGTTTA
AACACTAGTCCGCTGAGCAATAACTAGCATAACCCCTTGGGGCCTCTAAACGGGTCTTGAGGGGTTTTT
GCTGAAAGGAGGAACTATATCCGGGCTTCCTCGCTCACTGACTCGCTGCGCTCGGTCGTTCGGCTGCGG
CGAGCGGTATCAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTGGCGTTTTTCC
ATAGGCTCCGCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGACGCTCAGT
GGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGC
TTAATCAGTGAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGAGACCCACG
CTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTATGGCTTCA
TTCAGCTCCGGTTCCCAACGATCAAGGCGAGTTACATGATCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACT
GCATAATTCTCTTACTGTCATGCCATCCGTAAGATGCTTTTCTGTGACTGGTGAGTACTCAACCAAGTCAT
TCTGAGAATAGTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACCA
GCGTTTCTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCCGAAAAGTGCC
ACCTGACGTCTAAGAAACCATTATTATCATGACATTAACCTATAAAAATAGGCGTATCACGAGGCCCTTT
```

FIG. 16 (Cont.)

CGTCTCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTGTC
GGGGCTGGCTTAACTATGCGGCATCAGAGCAGATTGTACTGAGAGTGCACCATATATGCGGTGTGAAAT
ACCGCACAGATGCGTAAGGAGAAAATACCGCATCAGGAAATTGTAAACGTTAATATTTTGTTAAAATTC
GCGTTAAATTTTTGTTAAATCAGCTCATTTTTTAACCAATAGGCCGAAATCGGCAAAATCCCTTATAAATC
AAAAGAATAGACCGAGATAGGGTTGAGTGTTGTTCCAGTTTGGAACAAGAGTCCACTATTAAAGAACGT
GGACTCCAACGTCAAAGGGCGAAAAACCGTCTATCAGGGCGATGGCCCACTACGTGAACCATCACCCTA
ATCAAGTTTTTTGGGGTCGAGGTGCCGTAAAGCACTAAATCGGAACCCTAAAGGGAGCCCCCGATTTAG
AGCTTGACGGGGAAAGCCGGCGAACGTGGCGAGAAAGGAAGGGAAGAAAGCGAAAGGAGCGGGCGC
TAGGGCGCTGGCAAGTGTAGCGGTCACGCTGCGCGTAACCACCACACCCGCCGCGCTTAATGCGCCGCT
ACAGGGCGCGTCGCGCCATTCGCCATTCAGGCTGCGCAACTGTTGGGAAGGGCGATCGGTGCGGGCCT
CTTCGCTATTACGCCAGCTGGCGAAAGGGGGATGTGCTGCAAGGCGATTAAGTTGGGTAACGCCAGGG
TTTTCCCAGTCACGACGTTGTAAAACGACGGCCAGTGAATTG (SEQ ID NO:7)

Note: A pT7CFE1 derivative containing a Gateway cloning site, an ampicillin resistance gene for human IVT expression of fusion proteins bearing a C-terminal TolA spacer, HaloTag, Flag and His-tags

SEQUENCES OF PRIMERS:

Ribosome display-based barcoding:

Template barcoded (F):
CGAAATTAATACGACTCACTATAGGGAATGATACGGCGACCACCGAGGG*****AGA
GAATGAGGA (Note: Multiple oligos, and asterisks denote a barcoding sequence composed of A/T/C) (SEQ ID NO:8)

Template (R): TGCTAGTTGCTCCCGCAC   (SEQ ID NO:9)

RT primer: /5Acryd/T/ideSBioTEG/TTTTTTTTTCAAGCAGAAGACGGCATACGA   (SEQ ID NO:10)

HaloTag-based barcoding:

Universal template of barcoding DNA:
ACTTCAGTACGTCACTACCAACAATGATGGAATCCCTAGGTTGGCTTACCAAAAATG
AAGCTGATGAATACTCCCTCAAAGACAATTGTCAACCTT ACTTGTCCATTCCTGAAG
AAATATTATATTTATACAACTTACCCATAGAATCCTATCGTATGCCGTCTTCTGCTTG
(SEQ ID NO:11)

Barcoding DNA (F):
AATGATACGGCGACCACCGAGGGG****ACTTCAGTACGTCACTACCAAC   (SEQ ID NO:12) (Note: Multiple oligos, and asterisks denote a barcoding sequence composed of A/T/C)

Barcoding DNA (R): CAAGCAGAAGACGGCATACGA   (SEQ ID NO:13)

Barcoding DNA modification (F):
/5Acryd/T/iUniAmM/TTTTTTTTTAATGATACGGCGACCACCGA   (SEQ ID NO:14)

Barcoding DNA modification (R):
/5Acryd/T/ideSBioTEG/TTTTTTTTTCAAGCAGAAGACGGCATACGA   (SEQ ID NO:15)

FIG. 16 (Cont.)

Polony amplification:
Bridge amplification (F): /5Acryd/TTTTTTTTTAATGATACGGCGACCACCGA   (SEQ ID NO:16)
Bridge amplification (R): /5Acryd/TTTTTTTTTCAAGCAGAAGACGGCA/ideoxyU/ACGA (SEQ ID NO:17)
Fluorescence hybridization:
Sequencing 1_Cy3: CCCGGGTTCCTCATTCTCT/Cy3/   (SEQ ID NO:18)
Sequencing 2_Cy5: GGTAGTGACGTACTGAAGT/Cy5/   (SEQ ID NO:19)
Sequencing:
Sequencing 1: CCCGGGTTCCTCATTCTCT   (SEQ ID NO:20)
Sequencing 2: GGTAGTGACGTACTGAAGT   (SEQ ID NO:21)

BARCODED PROTEIN ARRAY FOR MULTIPLEX SINGLE-MOLECULE INTERACTION PROFILING

RELATED APPLICATIONS

This application is a continuation application which claims priority to U.S. application Ser. No. 17/671,931, filed on Feb. 15, 2022, which is a continuation application which claims priority to U.S. application Ser. No. 17/361,508, filed on Jun. 29, 2021, which is a continuation application which claims priority to U.S. application Ser. No. 17/073,509, filed on Oct. 19, 2020, which is a continuation application which claims priority to U.S. patent application Ser. No. 15/128,145, filed on Sep. 22, 2016, which application is a National Stage Application under 35 U.S.C. 371 of co-pending PCT application PCT/US2015/022388 designating the United States and filed Mar. 25, 2015; which claims the benefit of U.S. provisional application No. 61/969,997 and filed Mar. 25, 2014 each of which are hereby incorporated by reference in their entireties.

STATEMENT OF GOVERNMENT INTERESTS

This invention was made with government support under DE-FG02-02ER63445 awarded by the U.S. Department of Energy. The government has certain rights in this invention.

SEQUENCE LISTING

The instant application contains a Sequence Listing which has been submitted electronically in XML format and is hereby incorporated by reference in its entirety. Said XML copy, created on Aug. 29, 2022, is named "Sequence_Listing_010498_01382_ST26" and is 84 KB in size.

FIELD

The present invention relates to methods and compositions for massively parallel quantitative analyses of molecular interactions at a single-molecule level.

BACKGROUND

Compared with recent advances in massively parallel DNA sequencing (Shendure, J. & Ji, H. Next-generation DNA sequencing. Nat. Biotechnol. 26, 1135-1145 (2008)), high-throughput protein analyses, such as yeast-two-hybrid screening (Dreze, M. et al. High-quality binary interactome mapping. Methods Enzymol. 470, 281-315 (2010)), protein microsrray (MacBeath, G. & Schreiber, S. L. Printing proteins as microarrays for high-throughput function determination. Science 289, 1760-1763 (2000)), and affinity purification-mass spectrometry (Gavin, A. C. et al. Functional organization of the yeast proteome by systematic analysis of protein complexes. Nature 415, 141-147 (2002)), are impeded by ensemble measurements, which necessitate individual analyte separation or enrichment and, therefore, compromise throughput and cost-effectiveness. Single molecule protein detection has been achieved using optical methods (Weiss, S. Fluorescence spectroscopy of single biomolecules. Science 283, 1676-1683 (1999)), but the multiplexity is limited to the number of spectrally non-overlapping chromophores.

SUMMARY

Embodiments of the invention are directed to a DNA barcoded protein array technology for parallel protein interaction profiling on a single molecule basis. DNA barcodes are attached to proteins collectively via ribosome display (Hanes, J. & Pluckthun, A. In vitro selection and evolution of functional proteins by using ribosome display. Proc. Natl. Acad. Sci. U.S.A. 94, 4937-4942 (1997)) or individually via enzymatic conjugation. Barcoded proteins are assayed en masse in aqueous solution and subsequently immobilized in a polyacrylamide (PAA) thin film to construct a random SM array, where barcoding DNAs are amplified into in situ polymerase colonies (polonies) (Mitra, R. D. & Church, G. M. In situ localized amplification and contact replication of many individual DNA molecules. Nucleic Acids Res. 27, e34 (1999)) and analyzed by DNA sequencing. This method allows precise quantification of various proteins with a throughput of over one billion molecules per array. Novel methods are described herein that measure protein interactions based on the statistical analysis of co-localized polonies arising from barcoding DNAs of interacting proteins. Two highly demanding applications, G-protein coupled receptor (GPCR) and antibody screening and binding profiling, were demonstrated. The methods described herein for the first time enable library vs. library screening in a single assay, which can simultaneously interrogate molecular binding affinity and specificity.

In certain exemplary embodiments, a method for attaching a plurality of barcodes to a plurality of polypeptides. The method includes the steps of attaching a barcode to a plurality of DNA template sequences to produce a plurality of barcoded templates comprising a barcode sequence and a protein coding sequence, performing in vitro transcription to synthesized barcoded mRNA templates and then reverse transcription of the barcoded mRNA templates to produce a plurality of mRNA-cDNA hybrid sequences, and performing in vitro translation of the mRNA-cDNA hybrid sequences to generate a plurality of protein-ribosome-mRNA-cDNA complexes.

In certain aspects, the step of attaching is performed using PCR and in vitro transcription. In other aspects, the plurality of protein-ribosome-mRNA-cDNA complexes are formed by ribosome stalling. In other aspects, the plurality of barcoded sequences are synthesized in parallel on an immobilized support or individually synthesized as a mixture of random sequences on a support. In still other aspects, each of the steps is performed in a single container, and a correlation between a barcoding sequence and a protein sequence is determined using massively parallel DNA sequencing.

In certain aspects, the barcoded templates contain a polymerase (e.g., T7 polymerase) promoter, and mRNAs are synthesized from the barcoded DNA templates by in vitro transcription in a single container.

In other aspects, reverse transcription is performed using universal primers, and the cDNA sequences are complementary upstream to a ribosome binding site of the barcoded template. In certain aspects, ribosomes stall at the 3' end of the mRNA-cDNA hybrid sequences during in vitro translation due to one or both of a lack of stop codons or the presence of ribosome stalling peptide sequences. In other aspects, primers for cDNA synthesis contain one or both of 5' desthiobiotin modifications and 5' acrydite modifications. In yet other aspects, the protein coding sequence encodes one or more affinity tags (e.g., FLAG tags and the like), e.g., at the C-terminal of a protein of interest. In other aspects, the protein-ribosome-mRNA-cDNA complexes, which contain the full-length protein of interest, are purified using a protein affinity tag and a cDNA desthiobiotin tag In certain exemplary embodiments, a method for attaching a barcode to a polypeptide is provided, comprising the steps of providing a DNA template comprising an enzyme ligand at its 5' end, providing a fusion protein comprising an enzyme tag specific for the ligand, and allowing the enzyme to covalently bind the ligand to produce a polypeptide comprising a barcode.

In certain aspects, the method is performed using an automated high-throughput platform. In other aspects, at least 1000, 10,000, 1,000,000 or more polypeptides comprising a barcode sequence are prepared in parallel. In certain aspects, an enzyme tag is selected from the group consisting of one or more of HaloTag, CLIP tag, SNAP tag and the like. In other aspects, both the DNA template and the polypeptide comprise an affinity tag (e.g., the DNA template comprises a desthiobiotin tag and the polypeptide comprises a His tag), e.g., performing affinity purification using two steps.

In certain exemplary embodiments, a method of detecting and quantifying a plurality of polypeptides in situ is provided. The method includes the steps of providing in an aqueous medium a plurality of polypeptides comprising a barcode, immobilizing the plurality of polypeptides on a substrate, performing in situ amplification of the barcodes bound to the immobilized plurality of polypeptides, and identifying and quantifying amplified barcode sequences and recording their locations by in situ DNA sequencing.

In certain aspects, the polypeptides comprising barcodes are made according to one of the methods described above. In certain aspects, the plurality of polypeptides are randomly immobilized in a crosslinked polyacrylamide gel layer having a thickness of about a few microns. In other aspects, the nucleic acid sequences have a 5' end modification (e.g., an acrydite modification) and are copolymerized into the gel matrix to avoid template drifting. In yet other aspects, the nucleic acid sequences are amplified into polonies using solid-phase PCR. In still other aspects, the polonies are approximately 1-2 microns in diameter, and/or greater than about 1,000,000 polonies are analyzed on 1 mm2 array area. In certain aspects, the polonies are analyzed using sequencing-by-synthesis or sequencing-by-ligation to identify barcode sequences and location coordinates.

In certain exemplary embodiments, a method of detecting a protein-protein interaction between two or more polypeptides is provided. The method includes the steps of providing in an aqueous medium a plurality of polypeptides comprising a barcode under defined conditions (e.g., selected from the group consisting of one or any combination of ligands, cofactors, buffers and temperature) to allow formation of protein-protein interactions, stabilizing the protein-protein interactions by chemical crosslinking, immobilizing the plurality of polypeptides on a substrate, performing in situ amplification of the barcodes bound to the immobilized plurality of polypeptides, and detecting amplified barcode sequences, wherein co-localized amplified barcode sequences are detected when a protein-protein interaction has occurred between two or more polypeptides.

In certain aspects, the polypeptides comprising barcodes are made according to one of the methods described above. In certain aspects, co-localized barcodes are deconvoluted by DNA sequencing using different sequencing primers. In other aspects, the degree of co-localization of polonies is quantitatively analyzed by co-localization statistics using polony colocalization ratios and pair cross-correlation function (PCCF). In still other aspects, protein binding affinity can be quantitatively correlated with polony co-localization ratios. In still other aspects, the polypeptide is selected from the group consisting of a natural polypeptide, a recombinant polypeptide, and a de novo synthesized polypeptide. In other aspects, about 1,000,000,000 polypeptides are immobilized on half the area of a standard microscopic slide (e.g., a 25×75 mm2 slide). In certain aspects, a first library of at least 100,000 or more different polypeptides can be screened against a second other library of at least 100,000 or more different polypeptides or other barcoded molecules in a single assay. In certain aspects, both molecular binding affinity and specificity can analyzed in a single assay.

In certain exemplary embodiments, a method of detecting an interaction between polypeptides and nucleic acid sequences is provided. The method includes the steps of providing in an aqueous medium a plurality of polypeptides and nucleic acid sequences comprising a barcode under defined conditions to allow formation of polypeptide-nucleic acid interactions, stabilizing polypeptide-nucleic acid interactions by chemical crosslinking, immobilizing nucleic acid sequences on a substrate, performing in situ amplification of the barcodes bound to the immobilized polypeptide-nucleic acids, and detecting amplified barcode sequences, wherein co-localized amplified barcode sequences are detected when polypeptide-nucleic acid interactions have occurred between polypeptides and nucleic acid sequences.

In certain exemplary embodiments, a method of detecting an interaction between polypeptides and small molecules is provided. The method includes the steps of providing in an aqueous medium a plurality of polypeptides and small molecules comprising a barcode under defined conditions to allow formation of polypeptide-small molecule interactions, stabilizing polypeptide-small molecules interactions by chemical crosslinking, immobilizing polypeptides and small molecules on a substrate, performing in situ amplification of the barcodes bound to the immobilized polypeptides and small molecules, and detecting amplified barcode sequences, wherein co-localized amplified barcode sequences are detected when polypeptides and small molecule interactions have occurred between polypeptides and small molecules.

In certain exemplary embodiments, a method of detecting binding affinity of a plurality of polypeptides to an unlabeled ligand in a solution is provided. The method includes the steps of providing in an aqueous medium a plurality of polypeptides comprising a barcode, providing in the aqueous medium one or more substrates, wherein the substrates exhibits altered binding affinity to the polypeptides when bound by a ligand, introducing a barcode which is associated with a compound assayed in a well, and quantifying the co-localization of barcodes determine protein and ligand interactions.

In certain aspects, the polypeptides comprising a barcode are made according to one of the methods described above. In certain aspects, the substrates are proteins. In certain aspects, the ligand increases or decreases binding affinity of a polypeptide to one or more substrates. In certain aspects, a barcode associated with a compound assayed in a well can be introduced by linking the barcode to the substrate assayed in the well according to one of the methods described above. In certain aspects, a barcode is added to the original barcoding DNAs of the polypeptides using PCR, which is compatible with standard sample barcoding protocols used in next-generation sequencing methods. In other aspects, the ligand is selected from the group consisting of unlabelled small molecules and polypeptide. In yet other aspects, the polypeptide is an antibody or a binder protein, e.g., a nanobody, adnectin, an affibody, DARPin, or the like. In still other aspects, upon polypeptide binding to a ligand, the polypeptide participates in a protein-substrate interaction. In other aspects, a library of unlabelled ligands is assayed with a polypeptide library in multi-well plate for automatic high-through screening, and wherein, in each well, one ligand is profiled using a polypeptide library. In other aspects, both the polypeptide screening and compound profiling are performed at the same time to minimize assay time. In still other aspects, mixed proteins at approximately a zeptomole amount can be analyzed in a picoliter reactor to minimize reagent costs.

In certain exemplary embodiments, a method of detecting binding affinities of polypeptide library to ligand library is provided. The method includes the steps of providing a plurality of polypeptides having a barcode bound thereto, contacting the plurality of polypeptides with one or more test ligands, performing in situ amplification of the barcodes bound to the plurality of polypeptides and the plurality of substrates pooled from multiple wells, and detecting amplified barcode sequences, wherein co-localized amplified barcode sequences of polypeptides and substrates are detected when polypeptides have bound to ligands, and wherein the number of co-localized amplified barcode sequences relative to all amplified barcode sequences correlates with binding affinity to the substrate and thus the ligand efficacy to activate polypeptides.

In certain aspects, the ligand increases or decreases binding affinity of a polypeptide to a substrate. In other aspects, the ligand modulates one or more activities of the polypeptide. In other aspects, the ligand is a small molecule or a polypeptide. In other aspects, upon polypeptide binding to a ligand, the polypeptide participates in a protein-protein interaction.

In certain exemplary embodiments, a method of detecting binding affinity of a polypeptide to a compound is provided. The method includes the steps of providing in an aqueous medium a plurality of polypeptides having a barcode bound thereto, contacting the medium with one or more test compounds, immobilizing the plurality of polypeptides on a substrate, performing in situ amplification of the barcodes bound to the immobilized plurality of polypeptides, and detecting amplified barcodes, wherein co-localized amplified barcodes are detected when a polypeptide has bound to a compound, and wherein the number of co-localized amplified barcodes relative to non-co-localized amplified barcodes correlates with binding affinity to the compound.

In certain exemplary embodiments, a method of screening for a test compound that modulates an activity of a polypeptide is provided. The method includes the steps of providing a plurality of polypeptides having a barcode bound thereto, contacting the plurality of polypeptides with one or more test compounds, wherein polypeptide binding to a test compound alters the ability of the polypeptide to participate in a protein-protein interaction, performing in situ amplification of the barcode sequences bound to the plurality of polypeptides, and detecting amplified barcode sequences, wherein altered co-localization of amplified barcode sequences in the presence of the test compound is observed when the test compound modulates an activity of the polypeptide.

In certain aspects, test compound binding to a polypeptide modulates the ability of the polypeptide to participate in a protein-protein interaction.

In certain exemplary embodiments, a method of screening for a test compound that modulates an activity of a polypeptide is provided. The method includes the steps of providing in an aqueous medium a plurality of polypeptides having a barcode sequence bound thereto, contacting the medium with one or more test compounds, wherein polypeptide binding to a test compound alters the ability of the polypeptide to participate in a protein-protein interaction, immobilizing the plurality of polypeptides on a substrate, performing in situ amplification of the barcode sequences bound to the immobilized plurality of polypeptides, and detecting amplified barcode sequences, wherein altered co-localization of amplified barcode sequences in the presence of the test compound is observed when the test compound modulates an activity of the polypeptide

BRIEF DESCRIPTION OF THE DRAWINGS

FIGS. 1A-1B schematically depict protein barcoding methods according to certain aspects of the invention. (A) Collective barcoding via ribosome display. A short synthetic barcoding sequence can be introduced into DNA templates via PCR. PRMC complexes are formed via ribosome stalling induced by a C-terminal E. coli SecM peptide. Displayed proteins bearing a C-terminal Flag tag are separated from the ribosomes by an E. coli TolA spacer domain. (B) Individual barcoding via a HaloTag-mediated conjugation. A 220-base pair (bp) double-stranded barcoding DNA is modified with a HaloTag ligand (black triangle).

FIG. 11 depicts polony quantification of mixed binder proteins and antigens.

FIG. 12 depicts scFvs and human proteins used in the screening methods described further herein.

FIG. 13 depicts polony quantification for Ras-Raf-RBD binding assays used in methods described further herein.

FIGS. 14A-14B depict polony quantification for GPCR-p-arrestin binding assays.

FIG. 15 depicts proteins screened using methods described herein. The protein sequences are publically available.

FIG. 16 depicts vector and primer sequences according to certain aspects of the invention.

DETAILED DESCRIPTION OF CERTAIN EMBODIMENTS

Figure 2A:
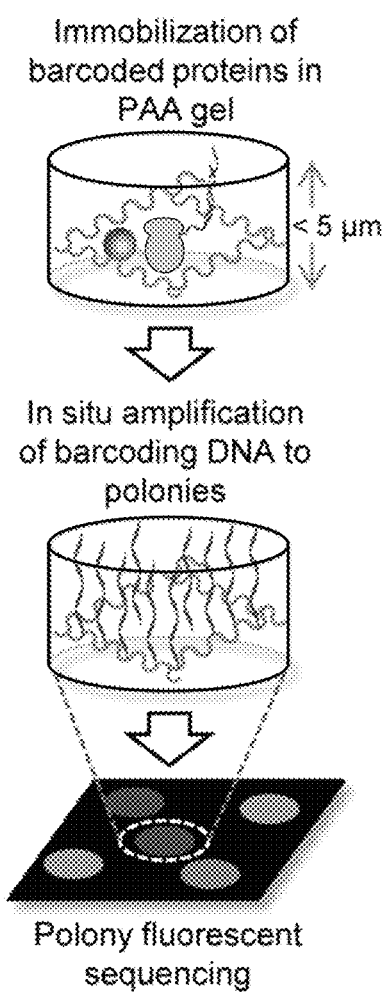
FIGS. 2A-2C depict amplification and quantification of barcoding DNAs. (A) Schematic of in situ polony amplification and sequencing. Barcoded proteins were immobilized in a PAA gel matrix attached to a Bind-Silane treated glass slide. The slide was assembled into a flow cell, where barcoding DNAs could be amplified into polonies for fluorescence imaging-based sequencing. (B) Representative merged images of polonies hybridized with Cy5 (red), Cy3 (green) and fluorescein (blue)-labelled oligos (20× objective). (C) Polony quantification of mixed protein binders and antigens. Pearson correlation coefficient R was calculated for different coverages grouped by dotted lines.

Embodiments of the present invention are directed to novel methods for attaching barcodes to polypeptides. Embodiments of the present invention are directed to novel methods for detecting interactions, e.g., protein-protein interactions, protein-nucleic acid interactions, protein-mall molecules interaction, binding affinities and the like. In certain aspects, the methods described herein are performed using massively parallel techniques.

In various embodiments, the methods disclosed herein comprise amplification of nucleic acids including, for example, polynucleotides, oligonucleotides and/or oligonucleotide fragments. Amplification methods may comprise contacting a nucleic acid sequence with one or more primers (e.g., primers that are complementary to barcode sequences) that specifically hybridize to the nucleic acid under conditions that facilitate hybridization and chain extension. Exemplary methods for amplifying nucleic acids include the polymerase chain reaction (PCR) (see, e.g., Mullis et al. (1986) Cold Spring Harb. Symp. Quant. Biol. 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) Science 241:1077-1080; and Nakazawa et al. (1994) Proc. Natl. Acad. Sci. U.S.A. 91:360-364), self-sustained sequence replication (Guatelli et al. (1990) Proc. Natl. Acad. Sci. U.S.A. 87:1874), transcriptional amplification system (Kwoh et al. (1989) Proc. Natl. Acad. Sci. U.S.A. 86:1173), Q-Beta Replicase (Lizardi et al. (1988) BioTechnology 6:1197), recursive PCR (Jaffe et al. (2000) J. Biol. Chem. 275:2619; and Williams et al. (2002) J. Biol. Chem. 277: 7790), the amplification methods described in U.S. Pat. Nos. 6,391,544, 6,365,375, 6,294,323, 6,261,797, 6,124,090 and 5,612,199, isothermal amplification (e.g., isothermal bridge amplification (IBA), rolling circle amplification (RCA), hyperbranched rolling circle amplification (HRCA), strand displacement amplification (SDA), helicase-dependent amplification (HDA), PWGA or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C. In certain aspects, a double stranded target nucleic acid may be denatured at a temperature greater than 90° C. in a conventional PCR using Taq DNA polymerase, or by adding formamide at 60° C. in isothermal bridge amplification using Bst polymerase.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., Nucleic Acids Research, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) Anal. Biochem., 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., Biotechniques, 26:112-126 (1999); Becker-Andre et al., Nucleic Acids Research, 17:9437-9447 (1989); Zimmerman et al., Biotechniques, 21:268-279 (1996); Diviacco et al., Gene, 122:3013-3020 (1992); Becker-Andre et al., Nucleic Acids Research, 17:9437-9446 (1989); and the like.

In certain embodiments, methods of determining the sequence of one or more nucleic acid sequences of interest, e.g., polynucleotides, oligonucleotides and/or oligonucleotide fragments, are provided. Determination of the sequence of a nucleic acid sequence of interest can be performed using variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) Nat. Methods 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) Genome Res. 8:769-76; Kwok (2000) Pharmocogenomics 1:95-100; and Shi (2001) Clin. Chem. 47:164-172).

Embodiments of the present invention are directed to polynucleotides, oligonucleotides, small molecules, substrates, test compounds and the like having one or two or more labels (e.g., barcode sequences) attached thereto. As used herein, the term "barcode" refers to a unique oligonucleotide sequence that allows a corresponding nucleic acid sequence (e.g., an oligonucleotide fragment) to be identified, retrieved and/or amplified. In certain embodiments, barcodes can each have a length within a range of from 4 to 36 nucleotides, or from 6 to 30 nucleotides, or from 8 to 20 nucleotides. In certain exemplary embodiments, a barcode has a length of 4 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

In certain embodiments, one or more markers are used to detect and/or retrieve (i.e. purify) polynucleotides, oligonucleotides, small molecules, substrates, test compounds and the like described herein. Examples of detectable and/or retrievable markers include various radioactive moieties, enzymes, prosthetic groups, fluorescent markers, luminescent markers, bioluminescent markers, metal particles, protein-protein binding pairs, protein-antibody binding pairs and the like. Detectable markers are commercially available from a variety of sources.

In certain aspects of the invention, detectable and/or retrievable proteins and/or protein tags are provided. Examples of detectable fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of detectable bioluminescent proteins include, but are not limited to, luciferase (e.g., bacterial, firefly, click beetle and the like), luciferin, aequorin and the like. Examples of detectable and/or retrievable enzyme systems include, but are not limited to, galactosidases, glucorinidases, phosphatases, peroxidases, cholinesterases and the like.

Biotin, or a derivative thereof, may also be used as a detectable and/or retrievable label, and subsequently bound by a detectably labeled avidin/streptavidin derivative (e.g. phycoerythrin-conjugated streptavidin), or a labeled anti-biotin antibody. Digoxigenin may be expressed subsequently bound by a labeled anti-digoxigenin antibody (e.g. fluoresceinated anti-digoxigenin). In general, any member of a conjugate pair may be incorporated into a detection oligonucleotide provided that a detectably labeled conjugate partner can be bound to permit detection. As used herein, the term antibody refers to an antibody molecule of any class, or any sub-fragment thereof, such as an Fab.

Other suitable labels for detection and/or retrieval include one or more protein tags. As used herein, the term "protein tag" refers to a heterologous polypeptide sequence linked to a polymerase of the invention. Protein tags include, but are not limited to, Avi tag (GLNDIFEAQKIEWHE) (SEQ ID NO:22), calmodulin tag (KRRWKKNFIAVSAANRFK-KISSSGAL) (SEQ ID NO:23), FLAG tag (DYKDDDDK) (SEQ ID NO:24), HA tag (YPYDVPDYA) (SEQ ID NO:25), His tag (HHHHHH) (SEQ ID NO:26), Myc tag (EQKLISEEDL) (SEQ ID NO:27), S tag (KETAAAKFER-QHMDS) (SEQ ID NO:28, SBP tag (MDEKTTGWRGGHVVEGLAGELEQLRARLEHHPQ GQREP) (SEQ ID NO:29), Softag 1 (SLAELLNAGLGGS) (SEQ ID NO:30), Softag 3 (TQDPSRVG) (SEQ ID NO:31), V5 tag (GKPIPNPLLGLDST) (SEQ ID NO:32), Xpress tag (DLYDDDDK) (SEQ ID NO:33), Isopeptag (TDKDM-TITFTNKKDAE) (SEQ ID NO:34), SpyTag (AHIVMV-DAYKPTK) (SEQ ID NO:35), streptactin tag (Strep-tag II: WSHPQFEK) (SEQ ID NO:36) and the like.

Detection and/or retrieval method(s) used will depend on the particular detectable labels used in the microorganism. In certain exemplary embodiments, microorganisms may be selected for, screened for and/or retrieved using a microscope, a spectrophotometer, a tube luminometer or plate luminometer, x-ray film, magnetic fields, a scintillator, a fluorescence activated cell sorting (FACS) apparatus, a chromatography apparatus, a microfluidics apparatus, a bead-based apparatus or the like.

Terms and symbols of nucleic acid chemistry, biochemistry, genetics, and molecular biology used herein follow those of standard treatises and texts in the field, e.g., Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) Nucl. Acids Res. 12:203.

"Complex" refers to an assemblage or aggregate of molecules in direct or indirect contact with one another. In one aspect, "contact," or more particularly, "direct contact," in reference to a complex of molecules or in reference to specificity or specific binding, means two or more molecules are close enough so that attractive noncovalent interactions, such as van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" refers to a duplex or triplex of polynucleotides or a stable aggregate of two or more proteins. In regard to the latter, a complex is formed by an antibody specifically binding to its corresponding antigen.

"Duplex" refers to at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the Tm of a strand of the duplex and low monovalent salt concentration, e.g., less than 0.2 M, or less than 0.1 M. "Perfectly matched" in reference to a duplex means that the polynucleotide or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" refers to a contiguous sub-region or segment of a genome. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the Tm for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, Molecular Cloning A Laboratory Manual, 2nd Ed. Cold Spring Harbor Press (1989) and Anderson Nucleic Acid Hybridization, 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Kit" refers to any delivery system for delivering materials or reagents for carrying out a method of the invention. In the context of assays, such delivery systems include systems that allow for the storage, transport, or delivery of reaction reagents (e.g., primers, enzymes, microarrays, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. Such contents may be delivered to the intended recipient together or separately. For example, a first container may contain an enzyme for use in an assay, while a second container contains primers.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) Nucl. Acids Res. 27:875; Higgins et al., Meth. in Enzymol. (1979) 68:50; Engler et al. (1982) The Enzymes, 15:3 (1982); and Namsaraev, U.S. Patent Pub. 2004/0110213.

"Amplifying" includes the production of copies of a nucleic acid molecule of the array or a nucleic acid molecule bound to a bead via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

"Support" can refer to a matrix upon which nucleic acid molecules of a nucleic acid array are placed. The support can be solid or semi-solid or a gel. "Semi-solid" refers to a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

"Randomly-patterned" or "random" refers to non-ordered, non-Cartesian distribution (in other words, not arranged at pre-determined points along the x- or y-axes of a grid or at defined "clock positions," degrees or radii from the center of a radial pattern) of nucleic acid molecules over a support, that is not achieved through an intentional design (or program by which such design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon. Arrays of the invention can be randomly patterned or random.

"Heterogeneous" refers to a population or collection of nucleic acid molecules that comprises a plurality of different sequences. According to one aspect, a heterogeneous pool of oligonucleotide sequences is provided with an article of manufacture (e.g., a microarray).

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g., described by Scheit, Nucleotide Analogs (John Wiley, New York, 1980); Uhlman and Peyman, Chemical Reviews, 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., Exp. Opin. Ther. Patents, 6: 855-870 (1996); Mesmaeker et al., Current Opinion in Structural Biology, 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

As used herein, the terms "nucleic acid molecule," "nucleic acid sequence," "nucleic acid fragment," "oligonucleotide," "oligonucleotide fragment" and "polynucleotide" are used interchangeably and are intended to include, but are not limited to, a polymeric form of nucleotides that may have various lengths, either deoxyribonucleotides or ribonucleotides, or analogs thereof. Nucleic acid molecules include single stranded DNA (ssDNA), double stranded DNA (dsDNA), single stranded RNA (ssRNA) and double stranded RNA (dsRNA). Different nucleic acid molecules may have different three-dimensional structures, and may perform various functions, known or unknown. Non-limiting examples of nucleic acid molecules include a gene, a gene fragment, a genomic gap, an exon, an intron, intergenic DNA (including, without limitation, heterochromatic DNA), messenger RNA (mRNA), transfer RNA, ribosomal RNA, ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers. Nucleic acid molecules useful in the methods described herein may comprise natural nucleic acid sequences and variants thereof, artificial nucleic acid sequences, or a combination of such sequences.

An oligonucleotide sequence refers to a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more An "oligonucleotide fragment" refers to an oligonucleotide sequence that has been cleaved into two or more smaller oligonucleotide sequences. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., Molecular Cloning, Second Edition (Cold Spring Harbor Laboratory, New York, 1989), and like references. Oligonucleotides and polynucleotides may be single stranded or double stranded.

Nucleic acid molecules may optionally include one or more non-standard nucleotide(s), nucleotide analog(s) and/or modified nucleotides. Examples of modified nucleotides include, but are not limited to diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

In certain exemplary embodiments, large polynucleotides are provided. In certain aspects, isolation techniques that maximize the lengths of polynucleotides (e.g., DNA molecules) obtained are used. For example, in situ lysis or deproteinization (e.g., with EDTA, detergent, protease, any combinations thereof and the like) after agarose embedding (as routinely performed for pulsed field gel electrophoresis) can be used to obtain polynucleotides.

Nucleic acid molecules may be isolated from natural sources or purchased from commercial sources. Oligonucleotide sequences (e.g., barcodes) may also be prepared by any suitable method, e.g., standard phosphoramidite methods such as those described by Beaucage and Carruthers ((1981) Tetrahedron Lett. 22: 1859) or the triester method according to Matteucci et al. (1981) J. Am. Chem. Soc. 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

Nucleic acid molecules may be obtained from one or more biological samples. As used herein, a "biological sample" may be a single cell or many cells. A biological sample may comprise a single cell type or a combination of two or more cell types. A biological sample further includes a collection of cells that perform a similar function such as those found, for example, in a tissue. Accordingly, certain aspects of the invention are directed to biological samples containing one or more tissues. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples.

In certain aspects, nucleic acid sequences derived or obtained from one or more organisms are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. The term "organism" further includes, but is not limited to, a yeast (e.g., *S. cerevisiae*) cell, a yeast tetrad, a yeast colony, a bacterium, a bacterial colony, a virion, virosome, virus-like particle and/or cultures thereof, and the like.

Isolation, extraction or derivation of nucleic acid sequences may be carried out by any suitable method. Isolating nucleic acid sequences from a biological sample generally includes treating a biological sample in such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, CA): Epicentre Technologies (Madison, WI); Gentra Systems, Inc. (Minneapolis, MN); MicroProbe Corp. (Bothell, WA); Organon Teknika (Durham, NC); and Qiagen Inc. (Valencia, CA)).

Methods of RNA extraction are also well known in the art (see, for example, J. Sambrook et al., "Molecular Cloning: A Laboratory Manual" 1989, 2nd Ed., Cold Spring Harbour Laboratory Press: New York) and several kits for RNA extraction from bodily fluids are commercially available (e.g., Ambion, Inc. (Austin, TX); Amersham Biosciences (Piscataway, NJ); BD Biosciences Clontech (Palo Alto, CA); BioRad Laboratories (Hercules, CA); Dynal Biotech Inc. (Lake Success, NY); Epicentre Technologies (Madison, WI); Gentra Systems, Inc. (Minneapolis, MN); GIBCO BRL (Gaithersburg, MD); Invitrogen Life Technologies (Carlsbad, CA); MicroProbe Corp. (Bothell, WA); Organon Teknika (Durham, NC); Promega, Inc. (Madison, WI); and Qiagen Inc. (Valencia, CA)).

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g., an allele present in a population at a frequency of fifty percent or greater.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence (e.g., an oligonucleotide fragment, a barcode sequence or the like).

"Specific" or "specificity" in reference to the binding of one molecule to another molecule, such as an amplification or sequencing primer to a barcode sequence, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In certain aspects, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as van der Waal forces, hydrogen bonding, base-stacking interactions, ionic and hydrophobic interactions, and the like, dominate the interaction of the molecules.

"Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in Flow Cytometry: Instrumentation and Data Analysis (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

"Tm" is used in reference to "melting temperature." Melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, "Quantitative Filter Hybridization," in Nucleic Acid Hybridization (1985). Other references (e.g., Allawi, H. T. & Santa Lucia, J., Jr., Biochemistry 36, 10581-94 (1997)) include alternative methods of computation which take structural and environmental, as well as sequence characteristics into account for the calculation of Tm.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables and accompanying claims.

EXAMPLE I

Barcoded Protein Array Construction

Figure 5A:
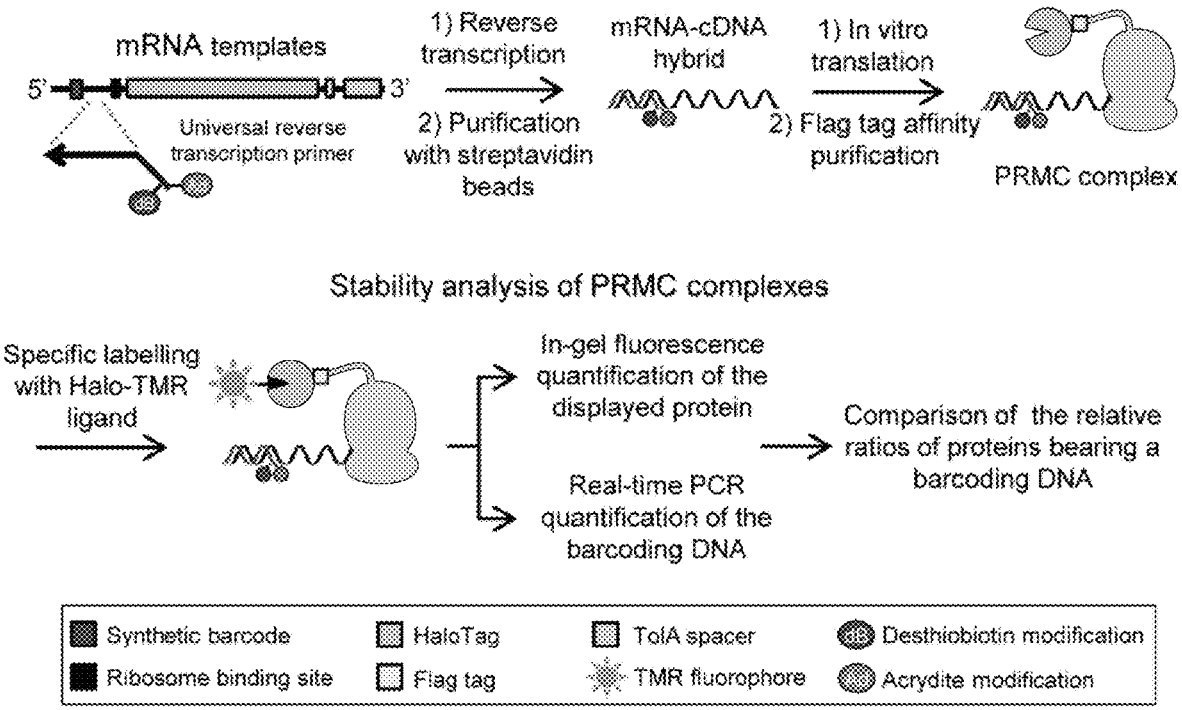
FIGS. 5A-5B depict the improved stability of PRMC complexes generated in a reconstituted E. coli IVT (PURE) system. (A) HaloTag or HaloTagged proteins were applied to measure the PRMC complex stability. The 5'-acrydite modification of cDNAs is required for the array analysis of PRMC complexes, but not relevant to this stability assay. (B) Comparison of the PRMC complex stability in the PURE and an E. coli crude extract (S30) IVT system. Nucleic acid degradation or ribosome dissociation results in the loss of barcoding DNAs. IVT reactions were performed at 37° C. for 30 min and PRMC complexes were further incubated at room temperature for indicated periods of time before the stability analysis. Means of three independent experiments±standard deviations.
Figure 5B:
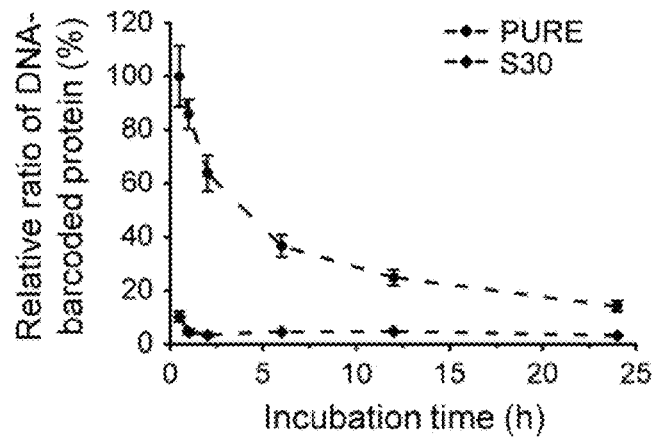
Figure 6A:
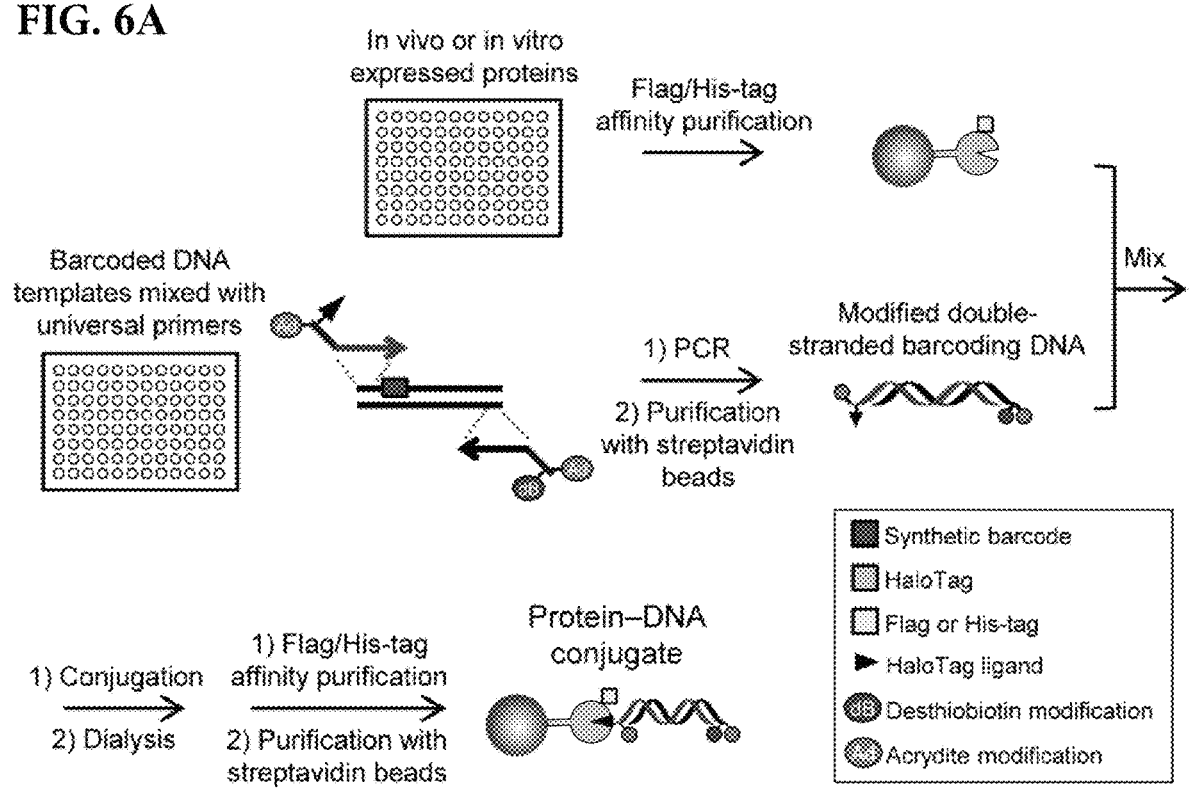
FIGS. 6A-6B depict HaloTag-based protein-DNA conjugation method. (A) A general barcoding protocol adaptable to an automatic platform. Fusion proteins carrying an N or C-terminal HaloTag and an affinity tag were conjugated to a 220 bp barcoding DNA bearing the 5' and 3' modifications. (B) Agarose gel electrophoresis of selected barcoding DNA and protein-DNA conjugate.
Figure 6B:
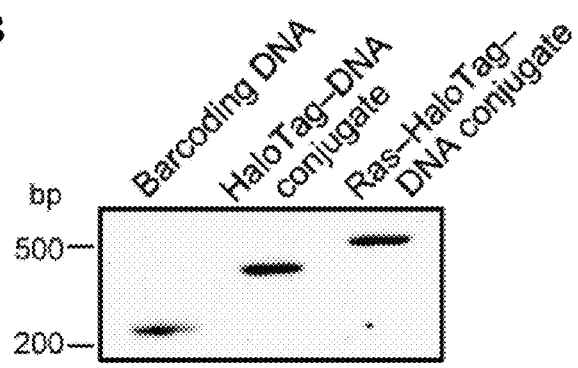

To analyze proteins in a massively parallel SM format proteins that were molecularly coupled to a DNA bearing a barcoding sequence were generated. One barcoding approach was to in vitro translate and display proteins on protein-ribosome-mRNA-cDNA (PRMC) complexes, in which the cDNA contains a synthetic barcode (FIG. 1A). Specifically, the ribosome display was performed by using mRNA-cDNA hybrids as templates and an in vitro translation (IVT) system reconstituted with purified components8 that was shown to stabilize PRMC complexes (FIG. 5). PRMC complexes bearing full-length proteins of interest were enriched by Flag-tag affinity purification. This approach was applicable to proteins of various sizes and size-related biases during barcode detection can be avoided by using uniformly sized barcoding DNAs. To barcode a large protein library, millions of chip-synthesized9,10 or random barcoding sequences could be introduced to the 5' end of protein open reading frames (ORFs) by polymerase chain reaction (PCR) and later matched to the ORF sequences by high-throughput DNA sequencing. Alternatively, some proteins that could only be functionally expressed in vivo were required to be individually barcoded. Thus, fusion proteins were constructed with an engineered enzyme tag, HaloTag11, which mediates an efficient covalent conjugation to a HaloTag ligand-modified double stranded DNA (FIG. 1B). This method could be readily adapted to a microtiter plate format for automated parallel protein production (FIG. 6).

Figure 2B:
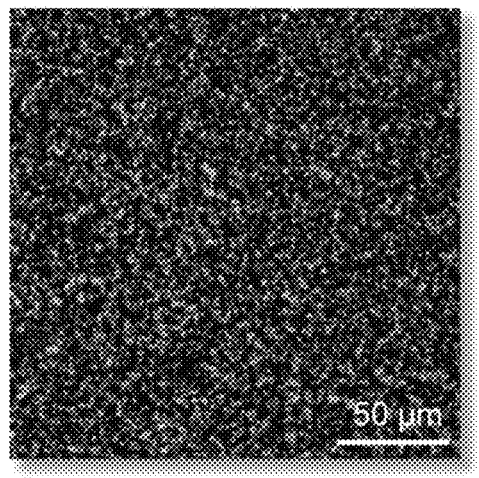
Figure 7A:
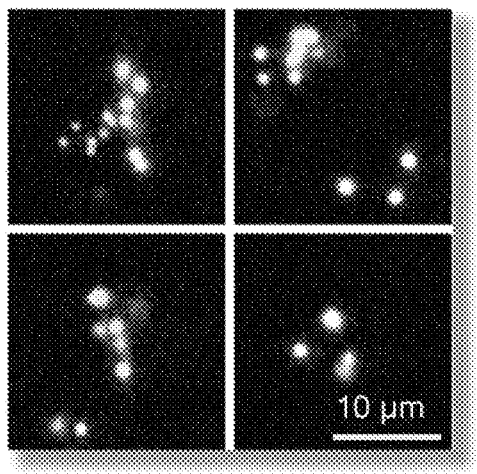
FIGS. 7A-7B depict that covalent immobilization of barcoding DNAs is required for in situ polony amplification. Representative images of polonies amplified from barcoding DNA templates without (A) or with (B) a 5'-acrydite modification (refer to FIGS. 5A and 6A). Oversized polonies or tiny adjacent polonies depicted in (A) can be resulted from template-drifting-induced multiple seeding events during the amplification.
Figure 7B:
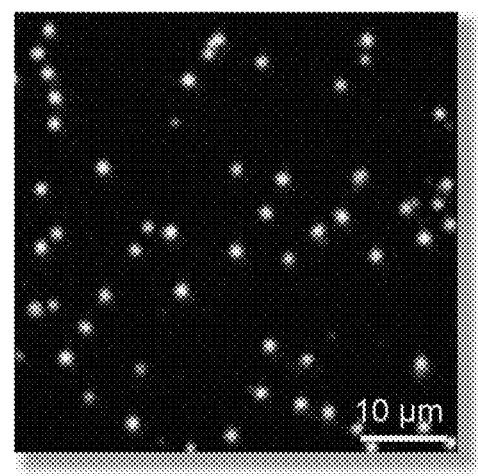
Figure 8A:
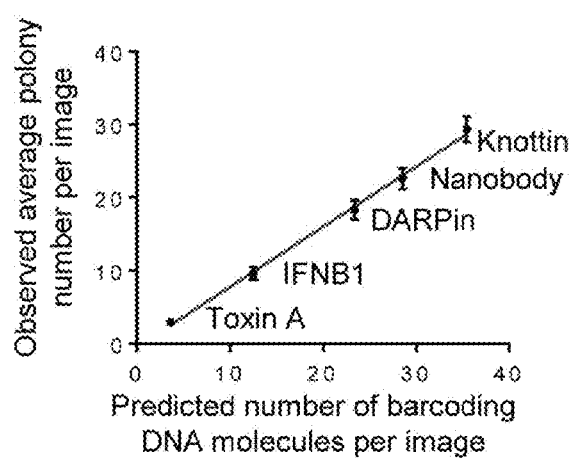
FIGS. 8A-8B graphically depict polony quantification of various barcoded proteins. (A) Plot showing the average number of polonies detected at a single imaging position vs. the average number of barcoding DNA templates predicted by real-time PCR quantification. Data represent mean values of 100 measurements; error bars, 95% CL. (B) Log-log plot of total numbers of polonies detected vs. dilution factors. Data represent mean values of two technical replicates.

A complex mixture of barcoded proteins could be identified and quantified by in situ sequencing their barcodes (FIG. 2A). They were immobilized into an ultrathin-layer crosslinked PAA gel attached to a microscopic slide, and their barcoding DNAs bearing a 5'-acrydite modification (FIGS. 5A and 6A) were covalently crosslinked to the gel matrix to prevent template drifting (FIG. 7). A solid-phase PCR, with two gel-anchored primers, was performed according to an adapted isothermal bridge amplification protocol12 in an assembled flow cell. This amplification showed a high efficiency of ~80% barcode detection (FIG. 8A), and resulted in polonies of 1-2 μm diameter (FIG. 2B) similar to the clusters generated on an Illumina platform12. Polonies were analyzed by hybridization with fluorescent probes7, single-base extension (SBE)13 or ligation-based sequencing14 in our work. As the polony density could reach over 1 million polonies per square millimeter, about one billion protein molecules can be measured in half the area of a 25×75 mm slide.

Figure 2C:
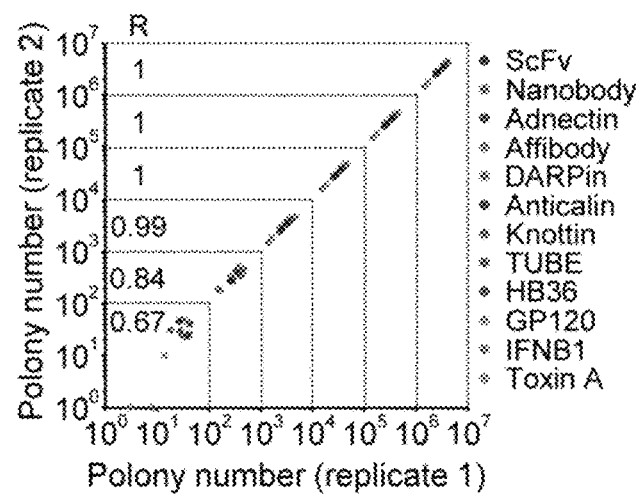
Figure 8B:
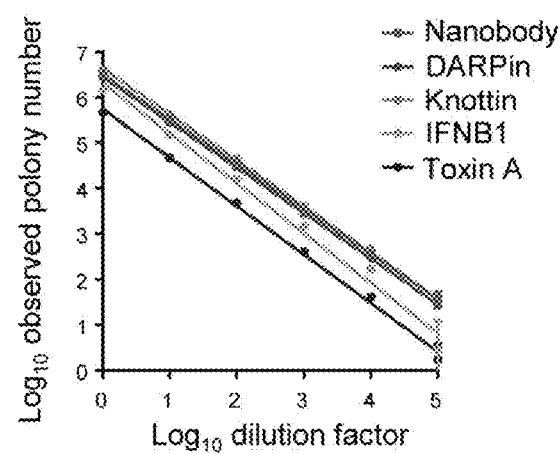

To test the accuracy of this method, nine immunoglobulin and non-immunoglobulin binding proteins and three antigens (e.g., human, bacterial and viral proteins) of a molecular weight range between 3.4 and 120 kDa (FIG. 11) were selected. Mixed PRMC complexes were prepared in six barcoded dilutions, with concentrations spanning six orders of magnitude, pooled together and subjected to the SM quantification. Barcode detection efficiencies of different proteins were found to be almost identical at various concentrations (FIG. 8). The quantification showed high reproducibility, e.g., the Pearson correlation coefficient R was above 0.99 when over 1,000 protein polonies were detected (FIG. 2C). Without intending to be bound by scientific theory, because the proteins were highly diluted (e.g., at less than picomolar concentrations) prior to array deposition, protein monomers should have been the predominant form.

EXAMPLE II

Detection of Protein-Protein Interactions

Figure 3A:
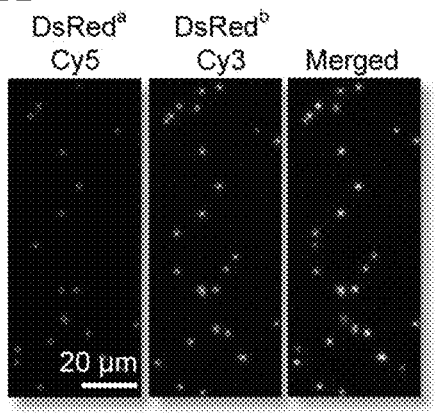
FIGS. 3A-3E depict analyses of protein interactions via polony co-localization. (A) Interaction of DsRed subunits resulted in co-localized polonies. DsRed polonies were identified by SBE with Cy5 (red) or Cy3 (green)-labelled ddNTPs. (B) The correlation between the polony co-localization ratios and KDs of Ras-Raf-RBD complexes. Means of measurements at 100 imaging positions ±95% confidence level (CL; refer to FIG. 13). Fitting equation, $R=R_{max} \times P/(K_D+P)$, where R is the predicted Raf-RBD polony co-localization ratio, $R_{max}$ is the maximum polony co-localization ratio when Raf-RBD is saturated by Ras, and P is the Ras concentration. (C) Schematic of multiplex GPCR screening and profiling by the binding assay of mixed barcoded GPCRs to barcoded β-arr2. (D) Comparison of β-arr2 binding to isoproterenol-activated β2-adrenergic receptor with or without GRK2-mediated phosphorylation. β-arr2 titration data were fitted by the one-site-specific model using GraphPad Prism 6. (E) Parallel compound profiling with three GPCRs. Data represent mean values of 50 measurements; error bars, 95% CL (refer to FIG. 14). P<0.01, *P<0.001, one-tailed paired Student's t test.
Figure 9B:
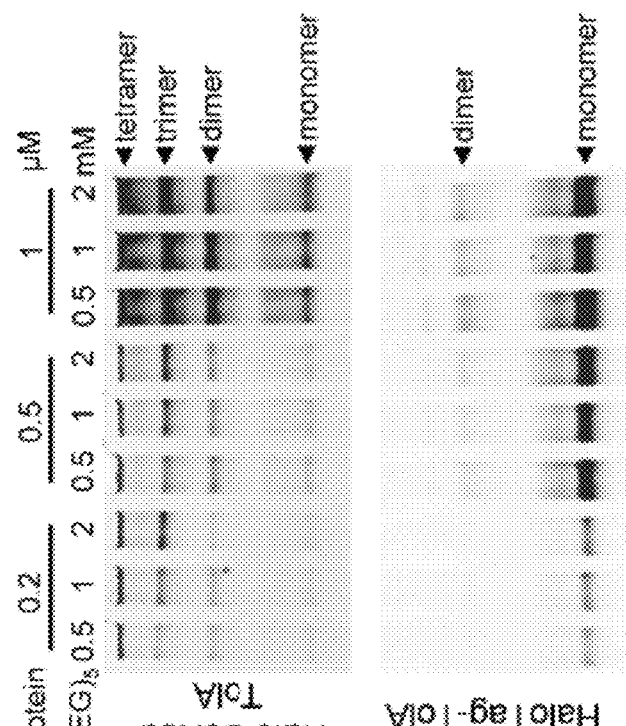
FIGS. 9A-9B depict that crosslinking efficiency of DsRed is improved by a lysine-rich TolA domain. (A) SDS-PAGE analysis of purified DsRed (Clontech) and HaloTag-DsRed-TolA proteins before (lanes 1 and 3) and after (lanes 2 and 4) the crosslinking. 10 µM purified proteins were crosslinked by 1 mM BS(PEG)5 in 20 mM HEPES buffer, pH 8.0, 150 mM KOAc at 4° C. for 1 h; Proteins were stained with Coomassie blue. Only a minor band of the crosslinked dimer was observed for DsRed (lane 2), and, in contrast, HaloTag-DsRed-TolA was all crosslinked as the tetramer or trimer (lane 4). Co-purified E. coli proteins (protein bands below the major band in the lane 3), which likely interact with the TolA, were efficiently crosslinked to HaloTag-DsRed-TolA. (B) Comparison of different crosslinking conditions. Proteins were labelled by Halo-TMR and analyze by fluorescent gel imaging. Only a minor fraction of HaloTag-TolA, a control to detect non-specific crosslinking, was crosslinked at increased protein concentrations.
Figure 9A:
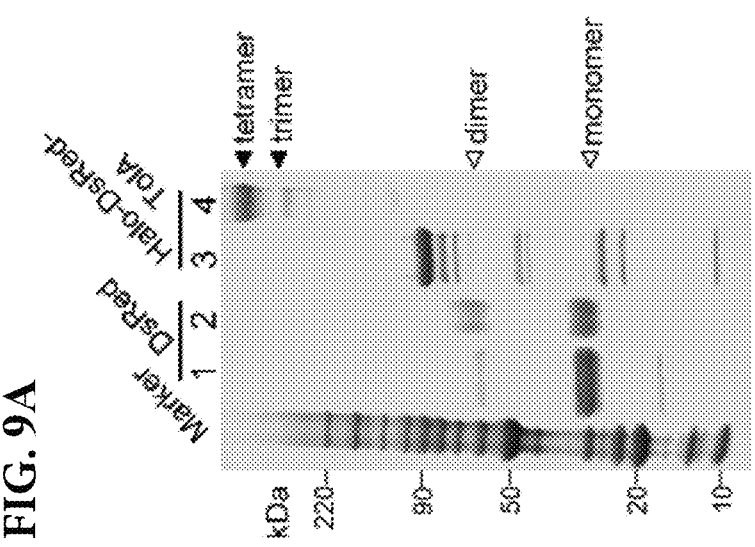

To detect protein-protein interactions, it was hypothesized that barcoding DNAs of proteins forming complexes would be amplified into co-localized polonies. To test this, DsRed, which naturally forms a tetramer15, was generated with monomers each bearing one of two different barcodes. To avoid dissociation of any complexes during the array analysis, they were crosslinked with an amine-reactive crosslinker, bis-N-succinimidyl-(pentaethylene glycol) ester (BS(PEG)5). The crosslinking was shown to be efficient due to the presence of a lysine-rich TolA spacer domain (FIG. 1A and FIG. 9). It was evident that barcoding DNAs of the co-localized monomers (DsReda and DsRedb) were co-amplified into overlapping polonies (FIG. 3A), providing a solid basis for further applications.

Figure 3B:
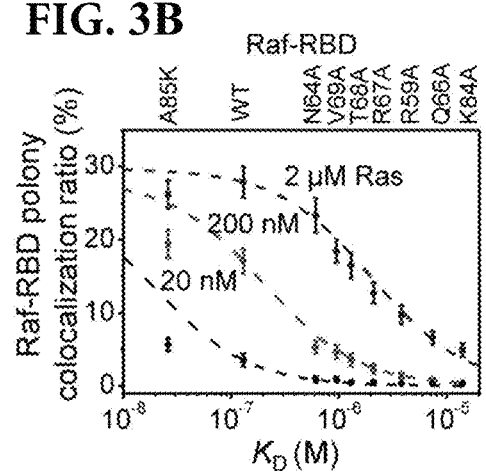

Because this approach detected polonies of both unbound and bound proteins in a single solution, it was queried whether it could provide a measure of protein binding affinities. A model system, the GTP-dependent binding of human H-Ras (Ras) to Ras-binding domain of c-Raf-1 (Raf-RBD)16, was chosen. A Raf-RBD polony co-localization ratio—the percentage of Raf-RBD polonies co-localized with Ras polonies—was measured for wild-type (WT) Ras and Raf-RBD and eight Raf-RBD mutants. The Ras protein concentration was titrated over three orders of magnitude (FIG. 3B). Although the co-localization ratio was sensitive to experimental variables (e.g., the crosslinking conditions, polony array density, etc.), all the proteins within a single assay were basically under the same reaction conditions. Given a similar proportion of active protein and crosslinking efficiency, polony co-localization ratios could be correlated with ratios of bound proteins at equilibrium and thus their binding affinities. To test this, the co-localization ratios were plotted against previously reported dissociation constants (KDs) ranging from nanomolar to micromolar17,18 (FIG. 3B and FIG. 11), and fitted by using a one-site-specific binding model (dashed curves). The fitted and observed average co-localization ratios show relatively high agreement ($R>0.96$), except for the A85K mutant of significantly lower experimental values than predicted by the model, likely due to the disruption of Lys85-mediated interactions by the crosslinking18. Therefore, this method could be useful for high-throughput screening of protein binding affinities.

EXAMPLE III

High-Throughput Screening

As a first high-throughput screening application, small molecule-mediated protein-protein interactions were studied. Importantly, a significant advantage of the novel method described herein over traditional solid-phase techniques such as protein microarrays3 is that proteins are both stored and assayed in aqueous solution. To exploit this, G-protein coupled receptors (GPCRs), the largest membrane protein family and premier drug targets19, were used to address challenges in screening. Current GPCR-ligand screening techniques mainly rely on cell-based assays20, which are subject to limitations such as the inhomogeneous nature of the samples, the presence of other cellular components that can cause false positives or negatives, and limited miniaturization and multiplexing capability (e.g., one receptor per assay). To prepare a homogenous SM GPCR sample compatible the methods described herein, receptors were stabilized in phospholipid bilayer nanodiscs21 by assembling detergent-solubilized GPCRs, phospholipids and a membrane scaffold protein, MSP1E3D1, into GPCR-nanodisc complexes22,23. GPCR activation upon ligand binding could be functionally assessed by β-arrestin binding to the active receptors, which is a G-protein independent assay applicable to almost all GPCRs including orphan receptors24.

Figure 3C:
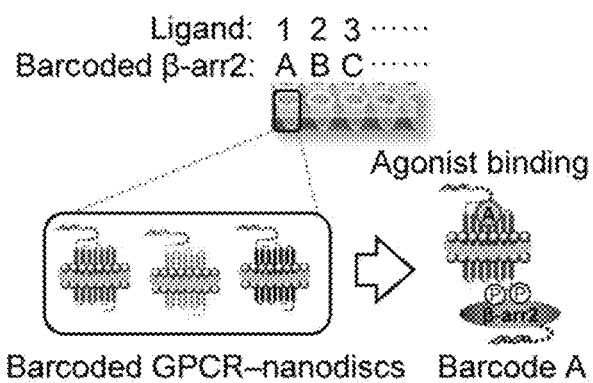
Figure 3D:
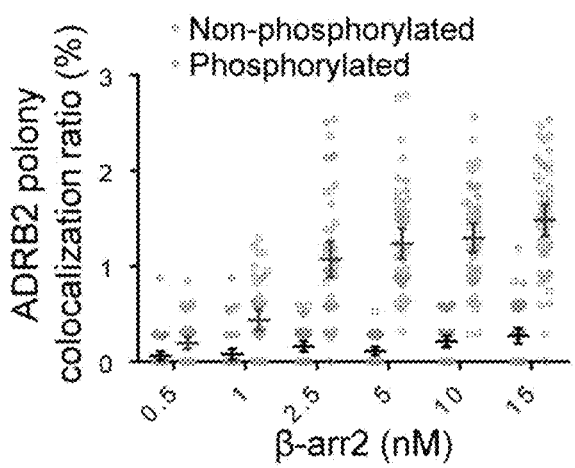

A compound library could be screened in multi-well plates, and in each well, one compound was assayed with many barcoded GPCRs and a β-arrestin-2 (β-arr2) protein bearing a well-position-associated barcode (FIG. 3C). All the samples were pooled and deposited on one slide, and the interaction of a GPCR with a compound was detected by the increased GPCR polony co-localization with the corresponding β-arr2 polonies. Efforts to obtain functional GPCRs using IVT systems were not successful, so they were instead expressed in baculovirus infected insect cells, purified using nanodiscs and individually barcoded (FIG. 1B). To establish assay conditions, β-arr2 binding to an agonist (isoproterenol) saturated β2-adrenergic receptor (ADRB2) was assessed, with and without GPCR kinase 2 (GRK2)-mediated receptor phosphorylation and under varied β-arr2 protein concentrations (FIG. 3D). The co-localization ratios were measured at 50 imaging positions on the array for statistical analysis. As expected, coupling the receptor phosphorylation to the assay improves the β-arr2 binding, e.g., a ~3 to 11-fold increase (largest P=0.002) of the average co-localization ratios after the phosphorylation. The fitting of β-arr2 titration data for the phosphorylated receptor yielded an apparent KD of 0.95 nM, which is close to the KD of 0.23 nM obtained from traditional binding assays using radiolabeled β-arr225.

Figure 3E:
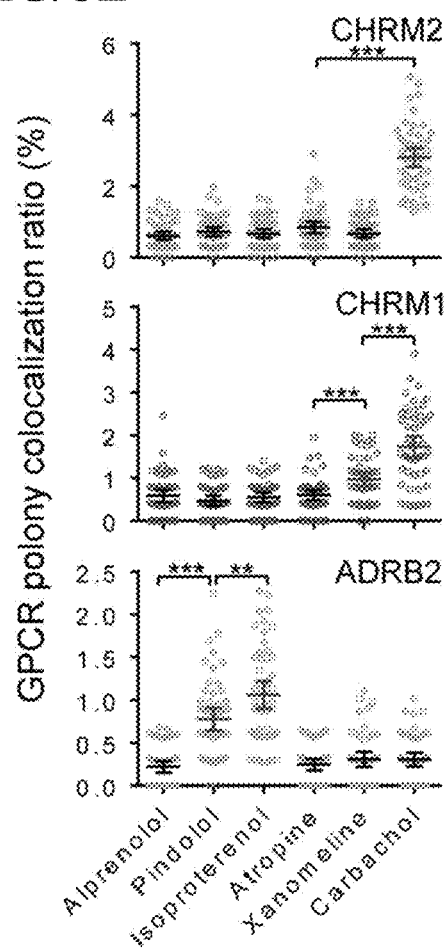

To test the screening performance, three GPCRs, ADRB2, M1 and M2 muscarinic acetylcholine receptors (CHRM1 and CHRM2), were assayed with six compounds including antagonists and full, partial, subtype selective and non-selective agonists (FIG. 3E and FIG. 12). The co-localization statistical analysis based on measurements of ~13,000-17,000 polonies for each receptor precisely identified the full agonists (isoproterenol and carbachol) from the antagonists and inactive compounds (largest $P<2.7\times10-10$).

Moreover, different types of agonists could be distinguished by comparing their polony co-localization ratios, e.g., the full and partial agonists for ADRB2 (isoproterenol and pindolol, respectively; $P<0.004$), and the orthosteric and allosteric agonists for CHRM1 (carbachol and xanomeline, respectively; $P<3\times10-6$). Thus, the methods described herein enabled both GPCR screening and compound profiling at the same time. Importantly, this method was capable of investigating a large number of GPCRs at the zeptomole level, which will drastically reduce the average screening time and reagent cost per receptor-ligand test.

EXAMPLE IV

Antibody Library Screening

A most remarkable feature of the methods described herein is their ability to screen two barcoded libraries in a single assay. Available techniques (e.g., yeast two-hybrid system2) for library vs. library screening are cell-based and require matching genes from two libraries in positive clones by performing individual PCR reactions26. To demonstrate this capability, a test of a demanding application, the binding profiling of antibody repertoire, was prototyped. The screening of natural or semisynthetic monoclonal antibody (mAb) libraries using methods known to others at the time of filing typically included binding affinity selection and specificity profiling which have to be conducted separately with current techniques. The traditional specificity profiling was costly, usually requiring at least one protein chip for a single antibody test27, and thus has only been commercially applied to therapeutic antibodies. However, both processes could be integrated using the methods described herein by screening an antibody library with a target protein library.

Figure 4A:
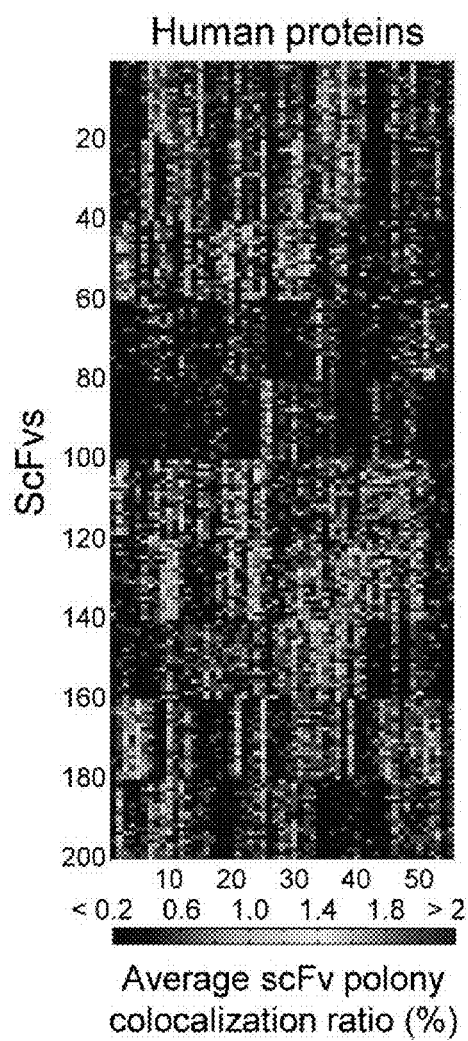
FIGS. 4A-4B depict parallel antibody binding profiling. (A) Heat map of the mean co-localization ratios measured at 100 imaging positions. ScFvs share the same origins were grouped by their numbers (FIG. 12). (B) The correlation between the co-localization statistics with the immunoprecipitation results. Selected scFvs were fused to a C-terminal streptavidin binding peptide (SBP) tag and captured by streptavidin-coated magnetic beads to pull down bound human protein fusions with a HaloTag, which could be labelled by Halo-TMR. Proteins were analyzed by fluorescent gel imaging. Error bars, 95% CL. ***P<0.001, one-tailed paired Student's t test.

Specifically, 200 antibodies, generated in single-chain variable fragment (scFv) form, were tested against 55 human cytokines, growth factors and receptors (FIG. 12). Twenty scFvs were derived by random mutagenesis from each of ten scFvs, the genes of which were previously synthesized from a programmable DNA microchip10. Barcoded scFv proteins were collectively generated in the reconstituted IVT system supplemented with disulfide bond enhancing factors (New England Biolabs). To set up a binding assay, the human proteins were assigned as probes, the concentrations of which are required to be adjustable to ensure formation of enough complexes with target scFvs. Although a human ORF library was recently synthesized using an *Escherichia coli* IVT system28, it was determined to be better for this application to individually synthesize the probes in a human IVT system (Thermo Scientific) and stabilize membrane proteins by adding assembled nanodiscs. Approximately 0.64 million polonies were sequenced and the co-localization ratios were measured for 11,000 scFv-probe pairs at 100 imaging positions (FIG. 4A and). 148 out of 200 scFvs were found with the highest co-localization ratios, and thus the highest specificity, to their predicted targets. Substantial cross-reactivity could be sensitively detected, e.g., 3474 scFv-probe pairs showed 10-fold higher polony co-localization than random distribution (P<0.01). ScFv mutants of a same scFv, grouped by their numbers, exhibited similar but not identical binding patterns to the probes.

Figure 4B:
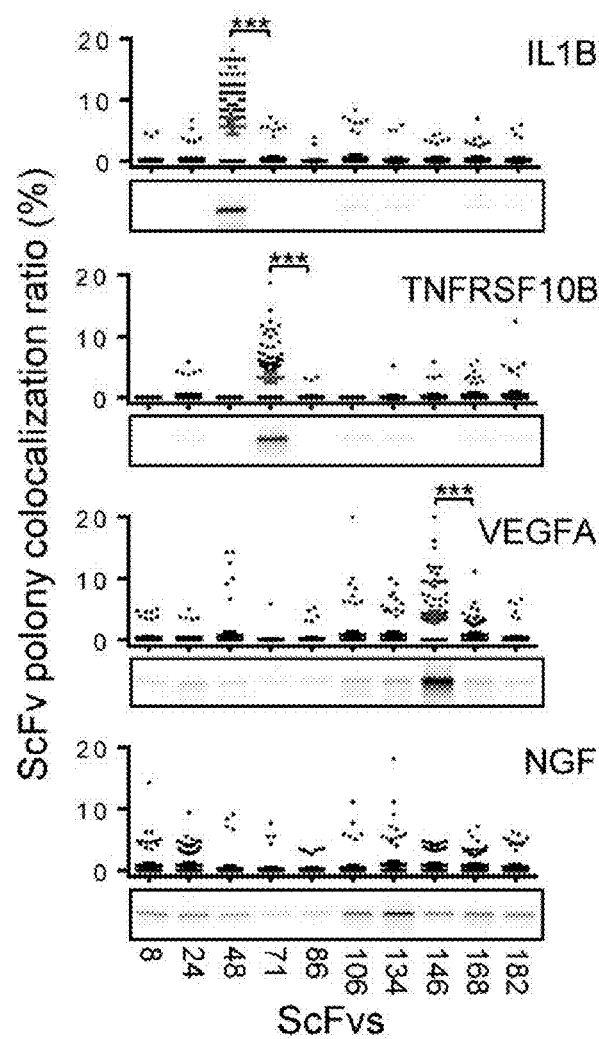

Next, the results of 40 scFv-probe pairs were confirmed by immunoprecipitation. The co-localization statistics were consistent with relative fluorescence intensities of the protein bands (FIG. 4B). Moreover, to further assess multiplexing potential, a mathematical model was developed (described further herein) that integrated parameters including KDs of protein-probe complexes to be detected and numbers of proteins and probes that can be assayed simultaneously. Notably, the model indicated that tens of thousands of proteins and probes can be quantitatively analyzed within a single assay.

EXAMPLE V

Discussion

Taken together, these data provide a next-generation method for protein-protein interaction profiling with fundamentally enhanced sensitivity, throughput and cost-effectiveness. Because the polony amplification and sequencing protocol is adaptable to industrial next-generation sequencing platforms, the methods described herein can be readily translated into many platforms and applications. The methods described herein are not limited to the studies of natural or recombinant proteins, and will be applicable to de novo proteins (e.g., with unnatural amino acids or modifications) which could be synthesized with IVT systems of high manipulability8, nucleic acids and barcoded small molecules29. Finally, the methods described herein, along with our ongoing research on single cell-based transcriptome sequencing30, profoundly extends imaging-based sequencing technology by demonstrating that new information can be derived from analyzing the spatial patterning as well as the sequence content and numbers of arrayed DNAs.

EXAMPLE VI

Mathematical Model

Co-Localization Statistics

To compare degrees of co-localization between different protein and probe pairs in an experiment, co-localization ratios, defined as the percentages of protein polonies co-localized with corresponding probe polonies, were measured and Student's t-tests were performed for the measurements at multiple imaging positions. The contribution from random co-localization can be estimated by calculating the mean value of pair cross-correlation function (PCCF) over the distance interval of zero to the co-localization threshold. In addition, the PCCF statistic (1) can be applied to characterize co-localization patterns of two polony species that were overlapped or partially overlapped. Below is how the PCCF values were calculated.

Let i and j be two types of objects for co-localization analysis and A be a sampled array area. A cross-correlation Ripley K-function $\hat{K}(r)$ can be estimated (2) as $$\hat{K}_{i,j}(r) = \frac{1}{A\hat{\lambda}_i\hat{\lambda}_j} \sum_k \sum_l \omega(i_k, j_l) I(d_{ik,jl} < r)$$

where $d_{ik,jl}$ is the distance between the centroids of k'th location of type i objects and the l'th location of type j objects, and $I(d_{ik,jl}<r)$ is the indicator function with the value 1 if $d_{ik,jl}<r$ is true and 0 otherwise. The density of type i objectives $\hat{\lambda}$ can be estimated as $$\hat{\lambda}_i = \frac{N_i}{A}$$

where $N_i$ is the total number of i objects. The weight function, $\omega(i_k, j_l)$ provides an edge correction but was here ignored ($\omega(i_k, j_l) \approx 1$). The function $\hat{K}_{i,j}(r)$ can be interpreted as the ratio of the number of i and j objects localized within radius r of each other, over the number that would be expected by chance. Following (1), a PCCF that considered co-localization was computed within a radial interval [r, r+Δr) via $$\frac{1}{A\hat{\lambda}_i\hat{\lambda}_j(2\pi r\Delta r + \pi\Delta r^2)} \sum_i \sum_j I(r \leq d_{ik,jl} < r + \Delta r)$$

where $\Sigma_i\Sigma_j I(r \leq d_{ik,jl}<r+\Delta r)$ and $A\hat{\lambda}_i\hat{\lambda}_j(2\pi r\Delta r+\pi\Delta r^2)$ are, respectively, an actual count of co-localized objects i and an average number of objects i that are co-localized with objects j by chance. The PCCF mean values were calculated over the interval of 0 to the co-localization threshold (r=0 and Δr=the co-localization threshold). In computing a PCCF value for an experiment in which Q images were analyzed, co-localization events were aggregated over all images and divided by Q times the expected number of random co-localization per image. By definition, randomly co-localized objects should have PCCF values of 1. However, to assess whether PCCFs derived in actual experiments were statistically significantly different from 1, following (1) 95% confidence intervals of the PCCFs of randomly co-localized objects were estimated using Monte-Carlo simulations. Specifically, each simulation assumed Q images, and within each image, Ni and Nj polony and probe objects, respectively, where Q was the number of images analyzed in the experiment whose PCCF was being evaluated, and Ni and Nj were the mean numbers of polony and probe objects observed in the actual experiment. Coordinates for the protein and probe polonies were randomly picked using uniform locations. All dimensions were scaled to actual image dimensions in pixels. For each simulation, a PCCF was computed in the same manner as in the actual experiment by aggregating co-localization events over Q random images. Finally, means and confidence intervals for these random PCCFs were obtained from 1000 simulations.

Initial Mathematical Model of SM-Based Protein Library Vs. Probe Library Binding Assay This describes a mathematical model whose aim is to assist understanding of the sensitivity and specificity of detection of protein-probe interactions in complex mixtures. The following items are assumed:

1) n species of barcoded proteins $P_1, P_2, \ldots, P_n$ are allowed to interact with m species of barcoded probes $R_1, R_2, \ldots, R_m$ in a one-pot assay. It is assumed that each protein is present in the same concentration and that the total protein concentration is $P_\#$. Similarly, it is assumed that the total concentration of probes is $R_\#$ and the concentration of each $R_j$ is $R_\#/m$. It is assumed that probe concentrations are titratable and that $R_\#/m >> P_\#/n$. For simplicity, it will be assumed here that m=n and that for each protein $P_i$ one probe $R_i$ (denoted with the same index) has been chosen or designed to specifically target the protein.

2) Due to folding and other issues relating to the efficiency of ribosome display, only a fraction $\alpha$ of each protein is in an active form that is capable of binding specifically to their targeting probes. The active and inactive forms of the protein $P_i$ will be denoted $P_i^+$ and $P_i^-$, with total concentrations $$\frac{\alpha P_\#}{n} \text{ and } \frac{(1-\alpha)P_\#}{n},$$

respectively. For similar reasons, only a fraction t of probes are active and can specifically bind to their targeted proteins, and their active and inactive forms will similarly be denoted $R_j^+$ and $R_j^-$, with concentrations $$\frac{\tau R_\#}{n} \text{ and } \frac{(1-\tau)R_\#}{n}.$$

These fractions are assumed to be stable throughout the assay, and active and inactive forms of the proteins and probes are assumed not to be able to interconvert. The fractions $\alpha$ and $\tau$ will be assumed to apply to all proteins and all probes, respectively.

3) For i=1, 2, . . . n, the active forms of protein $P_i$ and its specifically targeting probe $R_i$ will interact according to the reaction

(S1)

where $(P_i^+ R_i^+)_S$ denotes the complex formed from the specific interaction, and $K_D$ the dissociation constant of this complex, and where $K_D$ applies equally to each such protein-probe pair. All forms of protein $P_i$ will also interact non-specifically with all forms of all probes, including with specific probe $R_i$. This leads to four reactions between the active or inactive protein $P_i$ and each of the n probes $R_j$ (j=1, 2, . . . n), all of which are assumed to be characterized by the same non-specific dissociation constant U:

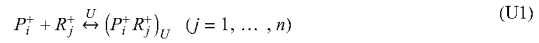 (U1)

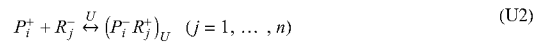 (U2)

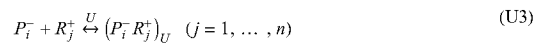 (U3)

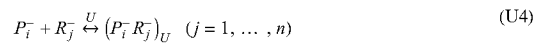 (U4)

It will also be assumed that (i) non-specific interactions between probes and proteins are always binary, and we can therefore neglect the possibility of ternary or higher complexes, and (ii) probes only non-specifically interact with proteins, and proteins only with probes, and thus that probes and probes, and proteins and proteins, will not interact.

4) After these reactions reach equilibrium, protein-probe complexes of all of these sorts are irreversibly captured by chemical crosslinking, and free probes are removed from the solution, leaving a residual concentration $R^0$. It is assumed that both free and complexed protein and probe molecules are then deposited on the surface of the array in proportion to their solution concentrations, and then immobilized on the array. Of these, it is assumed that only a fraction $\beta$ of protein and a fraction $\gamma$ of probe molecules bear barcoding DNAs that can be successfully amplified into polonies and detected on the array, and that the ability of protein and probe DNAs to be amplified is independent of whether the proteins and probes are free or in complex.

5) The following simplifications will be made regarding computation of PCCF statistics (see above): Instead of computing PCCFs by counting all pairs of $P_i$ and $R_i$ polonies within a specified distance threshold, PCCFs will be calculated from the numbers of $P_i$ polonies that are found co-localized with $R_i$ polonies in either of the following ways: (i) specific and non-specifically bound $P_i \cdot R_i$ complexes in which both components form polonies (as per the assumption 4) will be counted as intrinsically co-localized polonies; (ii) $P_i$ and $R_i$ polonies that are formed on the array by other means may be found to be randomly co-localized. A central value for random co-localization will be computed as the number of non-$P_i \cdot R_i$-derived $P_i$ polonies that are expected to be found by chance within the distance threshold from non-$P_i \cdot R_i$-derived $R_i$ polonies, given the numbers of these polonies obtained from 4 above. The sum of (i) and (ii) will be used to compute a central PCCF for $P_i$ and $R_i$ on the array, and variation from this central value will be estimated by random simulations described below. This calculation of PCCF differs from the formal definition given above and in (1) by being non-symmetrical in $P_i$ and $R_i$. Also, in counting $P_i$ polonies that are near $R_i$ polonies instead of counting all pairs of neighboring $P_i$ and $R_i$ polonies, it ignores the extra pairs that would be taken into account in the PCCF as formally defined should a $P_i$ polony be found near multiple $R_i$ polonies, and is thus conservative regarding co-localization counts compared to its formal definition.

The equilibriums of the five reactions in the assumption 3, and the assumption 1 that $R_\#/n >> P_\#$, yield 2n+1 equations involving the concentration $[P_i^+]$ of free $P_i^+$ and 2n equations involving the concentration $[P_i^-]$ of free $P_i^-$ $$[P_i^+]\frac{\tau R_\#}{nK_D} = [(P_i^+ R_i^+)_S] \quad (S1')$$

$$[P_i^+]\frac{\tau R_\#}{nU} = [(P_i^+ R_j^+)_U] \quad (j=1,\ldots,n) \quad (U1')$$

$$[P_i^+]\frac{(1-\tau)R_\#}{nU} = [(P_i^+ R_j^-)_U] \quad (j=1,\ldots,n) \quad (U2')$$

and $$[P_i^-]\frac{\tau R_\#}{nU} = [(P_i^- R_j^+)_U] \quad (j=1,\ldots,n) \quad (U3')$$

$$[P_i^-]\frac{(1-\tau)R_\#}{nU} = [(P_i^- R_j^-)_U] \quad (j=1,\ldots,n) \quad (U4')$$

Note that here there is a single (S1') equation involving the one specifically targeting probe $R_i$, but n instances each of (U1')-(U4'), one for each $R_j$ for j=1, . . . , n.

From the assumption 2 and the equations (S1'), (U1') and (U2'), we get $$[P_i^+] + [(P_i^+ R_i^+)_S] + \sum_{j=1}^n [(P_i^+ R_j^+)_U] + \sum_{j=1}^n [(P_i^+ R_j^-)_U] = \frac{\alpha P_\#}{n}$$

or $$[P_i^+]\left(1 + \frac{\tau R_\#}{nK_D} + \sum_{j=1}^n \frac{\tau R_\#}{nU} + \sum_{j=1}^n \frac{(1-\tau)R_\#}{nU}\right) = [P_i^+]\left(1 + \frac{\tau R_\#}{nK_D} + \frac{R_\#}{U}\right) = \frac{\alpha P_\#}{n}$$

which leads in turn to $$[P_i^+] = \frac{\alpha P_\#}{n + R_\#\left(\frac{\tau}{K_D} + \frac{n}{U}\right)} = \frac{\alpha P_\#}{n + \frac{R_\#}{\tilde{K}_D}} = \frac{\alpha P_\# \tilde{K}_D}{n\tilde{K}_D + R_\#}$$

where $\tilde{K}$ can be interpreted as an adjusted specific dissociation constant $$\tilde{K}_D = \frac{1}{\frac{\tau}{K_D} + \frac{n}{U}}$$

Similarly, from the assumption 2 and equations (U3') and (U4'), one gets $$[P_i^-] = \frac{(1-\alpha)P_\#}{n + \frac{nR_\#}{U}} = \frac{(1-\alpha)P_\# U}{n(U + R_\#)}$$

Using equations (S1') and (U1')-(U4'), the total concentration $[(P_i \cdot R_i)]$ of $(P_i \cdot R_i)$ complexes between the protein $P_i$ and its specifically targeting probe $R_i$ in any of their active and inactive forms is $$[(P_i \cdot R_i)] = \frac{\alpha P_\# \tilde{K}_D}{n\tilde{K}_D + R_\#}\left(\frac{\tau R_\#}{nK_D} + \frac{R_\#}{nU}\right) + \frac{(1-\alpha)P_\# U}{n(U+R_\#)}\left(\frac{R_\#}{nU}\right) =$$

$$\frac{P_\# R_\#}{n}\left(\frac{\alpha\left(1 - \frac{(n-1)\tilde{K}_D}{U}\right)}{n\tilde{K}_D + R_\#} + \frac{(1-\alpha)}{n(U+R_\#)}\right)$$

Total free protein concentration can also be computed as $$[P_i^+] + [P_i^-] = \frac{\alpha P_\# \tilde{K}_D}{n\tilde{K}_D + R_\#} + \frac{(1-\alpha)P_\# U}{n(U+R_\#)} = P_\#\left(\frac{\alpha \tilde{K}_D}{n\tilde{K}_D + R_\#} + \frac{(1-\alpha)U}{n(U+R_\#)}\right)$$

There is also a total concentration $[(P_i \cdot R_{j \neq i})]$ of $(P_i \cdot R_j)$ complexes between $P_i$ and $R_j$ probes (j≠i) that are not targeted to $P_i$, in any of their active and inactive forms. This is simplified as $$[(P_i \cdot R_{j \neq i})] = ([P_i^+] + [P_i^-])\frac{(n-1)R_\#}{nU}$$

Finally, it must also be considered that probe $R_i$ will be in non-specific complexes with other proteins $P_{j \neq i}$ than its specific target. By our assumptions above, since all proteins $P_j$ (j≠i) behave identically with respect to their targeting and non-targeting probes to $P_i$, we have $[P_j^+]+[P_j^-]=[P_i^+]+[P_i^-]$ for all j i, and therefore that $$[(P_{j \neq i} \cdot R_i)] = ([P_i^+] + [P_i^-])\frac{(n-1)R_\#}{nU}$$

Arraying, polony formation, and co-localization statistics

It is now assumed that the mixture is arrayed for SM assaying, and that polonies are formed on the array. Following assumption 4, the fractions of polonies relevant to evaluation of $P_i$ and $R_i$ co-localization can be computed as follows:

| | |
|---|---|
| $f_{(PR)} = \dfrac{\beta\gamma[(P_i \cdot R_i)]}{C}$ | Fraction of $(P_i \cdot R_i)$ complexes between $P_i$ and its specifically targeting probe $R_i$ that are detectable on the array as intrinsically co-localized polonies |
| $f_{(PX)} = \dfrac{\beta\gamma[(P_i \cdot R_{j \neq i})]}{C}$ | Fraction of $(P_i \cdot R_i)$ complexes between $P_i$ and other probes $R_j$ (j ≠ i) that are detectable on the array as polonies of $P_i$ that are intrinsically co-localized with those of other probes. |

$$f_P = \frac{\beta(1-\gamma)([(P_i \cdot R_i)] + [(P_i \cdot R_{j \neq i})]) + \beta([P_i^+] + [P_i^-])}{C}$$ Fraction of $P_i$ polonies that do not appear intrinsically co-localized wit probe polonies $$f_{(XR)} = \frac{\beta\gamma[(P_{j \neq i} \cdot R_i)]}{C}$$ Fraction of $(P_j \cdot R_i)$ complexes between probe $R_i$ and other proteins $P_j$ (j ≠ i) that are detectable on the array as polonies of $R_i$ that are intrinsically co-localized with the other proteins.

$$f_R = \frac{(1-\beta)\gamma([(P_i \cdot R_i)] + [(P_{j \neq i} \cdot R_i)]) + \gamma\frac{R^0}{n}}{C}$$ Fraction of $R_i$ polonies that do not appear intrinsically co-localized with protein polonies where $$c = (1 - (1-\beta)(1-\gamma))[(P_i \cdot R_i)] +$$

$$\beta[(P_i \cdot R_{j \neq i})] + \gamma[(P_{j \neq i} \cdot R_i)] + \beta([P_i^+] + [P_i^-]) + \gamma\frac{R^0}{n}$$

Note that as per the assumption 5, $f_{(PR)}$ determines the number of intrinsically co-localized $P_i$ and $R_i$ polonies found on the array. The other fractions will be used in calculation of the number of randomly co-localized polonies below. First the numbers of polonies of the various sorts is computed, and then random co-localization is calculated.

Let it now be assumed that $N_i$ polonies are detected for the protein $P_i$. These $N_i$ polonies may be apportioned as $$n_{(PR)} = \frac{N_i f_{(PR)}}{f_{(PR)} + f_{(PX)} + f_p}$$ Polonies of $P_i$ intrinsically co-localized with polonies of $R_i$ $$n_{(PX)} = \frac{N_i f_{(PX)}}{f_{(PR)} + f_{(PX)} + f_p}$$ Polonies of $P_i$ intrinsically co-localized with polonies of other probes $R_j$ (j ≠ i)

$$n_p = \frac{N_i f_p}{f_{(PR)} + f_{(PX)} + f_p}$$ Polonies of $P_i$ that are not intrinsically co-localized ith probe polonies.

It follows from the frequencies derived above that the following numbers of polonies are detected for the probe $R_i$ apart that are not counted with the $N_i$ $P_i$ protein polonies above (the only $R_i$ polonies considered with the $N_i$ polonies above are the $n_{(PR)}$ instances of $R_i$ polonies co-localized with $P_i$ polonies).

$$n_{(XR)} = \frac{N_i f_{(XR)}}{f_{(PR)} + f_{(PX)} + f_p}$$ Polonies of $R_i$ intrinsically co-localized with polonies of other proteins $P_j$ (j ≠ i)

$$n_R = \frac{N_i f_R}{f_{(PR)} + f_{(PX)} + f_p}$$ Polonies of $R_i$ that are not intrinsically co-localized with protein polonies.

In preparing to compute random co-localization and the final PCCF statistic, a question arises in the context of our highly multiplexed SM assay as to whether $P_i$ polonies from both uncomplexed $P_i^+$ and $P_i^-$ objects vs. $P_i$ polonies formed from $P_i \cdot R_{j \neq i}$ complexes should be treated equivalently regarding whether they can be randomly co-localized (and similarly for $R_i$ polonies). It could be the case that $P_i$ polonies formed within complexes cannot be co-localized with $R_i$ polonies to the degree that $P_i$ polonies formed from uncomplexed $P_i$ objects can due to steric constraints or other factors. In non-multiplexed assays, such as those considered in (1), this question never arises because the non-targeting partners in $P_i \cdot R_{j \neq i}$ and $P_{j \neq i} \cdot R_i$ complexes would never be surveyed for detection, and the resulting $P_i$ and $R_i$ polonies would all be considered isolated objects that could appear near each other by chance in the same way. A broader issue concerns the fact that the PCCF is specifically a Pair Cross-Correlation Function (1), and the question arises whether for multiplexed assays it might be better to develop and employ a higher-order multi-variate statistic that compares actual vs. expected random co-localization for many kinds of objects at once, somewhat like multi-variate ANOVAs analyze variances of many variables and interactions at once. However, in this initial model, we will in fact treat polonies derived from free probe and protein molecules vs. complexes equivalently in terms of their potential for random co-localization within the constraints indicated in the assumption 5. Notably, even when only considering pairwise co-localization, such as the application of PCCF in (1), where objects are labeled antibodies, the prima facie distinction between objects co-localized by virtue of targeting physical interactions and isolated objects that appear as random background is an idealization, since the apparently isolated objects are likely interacting non-specifically with many other kinds of unsurveyed molecules and complexes in the cell matrix, and PCCF remains a useful statistic even though these interactions are ignored.

Random Co-Localization

As noted in assumption 5 and discussed in the comment above, random co-localization will be considered between $P_i$ and $R_i$ polonies that do not arise from intrinsic co-localization from $P_i \cdot R_i$ complexes. The number of such polonies is known to be $n_{(PX)} + n_P$ for $P_i$, and $n_{(XR)} + n_R$ for $R_i$. Given imaged array area A and polony radius r, the density of these $R_i$ polonies that could appear anywhere on the array by chance can be estimated as $$\rho_R = \frac{n_R + n_{(XR)}}{A}$$

and the probability of a probe $R_i$ polony appearing in the vicinity of a $P_i$ protein polony by chance would then be $$\pi(2r)^2 \rho_R$$

Thus, the expected number of the $n_{(PX)} + n_P$ $P_i$ polonies that will have an $R_i$ polony localized nearby by chance will be $$n_{(PR)}^{rand} = \pi(2r)^2 \rho_R (n_{(PX)} + n_P)$$

Thus, the total number of $P_i$ polonies co-localized with $R_i$ complexes will be $$n_{(PR)}^{tot} = n_{(PR)} + n_{(PR)}^{rand}$$

PCCF Statistic

To complete the PCCF statistic as specified in assumption 5, $n_{(PR)}^{tot}$ must be divided by the expected number of $P_i$ polonies co-localized with $R_i$ polonies assuming that all of these individual polonies (including the ones in $P_i \cdot R_i$ complexes) could be co-localized by chance. Similar to the logic above, the total density of $R_i$ objects will now be $$\lambda_R = \frac{n_R + n_{(PR)} + n_{(XR)}}{A}$$

and the probability of a probe $R_i$ polony appearing in the vicinity of a $P_i$ protein polony will then be $$\pi(2r)^2 \lambda_R N_i$$

and, therefore $$PCCF = PCCF(P_\#, R_\#, R^0, n, \alpha, \tau, K_D, U, \beta, \gamma, N_i, A, r) = \frac{n_{(PR)}^{tot}}{\pi(2r)^2 \lambda_R N_i}$$

Random Simulations

To estimate the degree of variation to which the PCCF statistic may be subject under a given set parameters, distribution of PCCF values were computed using the formula above assuming that the six terms np, $n_{(PR)}$, $n_{(PX)}$, $n_{(XR)}$, $n_R$, and $n_{(PR)}^{rand}$ are all randomly drawn from Poisson distributions whose means are the values computed above within the model. Because these simulations do not take into account variation in actual samples or assay conditions, and because Poisson error may itself underrepresent the variability inherent in the underlying system vs. the model, these estimates must be considered lower bounds for the variance that will be encountered in actual assays.

Detection of Specific Vs. Non-Specific Binding as a Function of $K_D$ and n

As an application of the model, the PCCF values computed were compared for a mixture of n proteins and targeting probes that specifically interact with dissociation constant $K_D$, where n is allowed to vary over a large range, with the PCCF for mixtures of the same numbers of proteins and probes, in which all the proteins and probes interact only non-specifically with dissociation constant U. In particular, an array in which 5×108 protein polonies can be detected is assumed, and these are divided equally among the n proteins, where n is allowed to range between 500 and 500,000 (so that the number of detected polonies per protein species $N_i$ correspondingly varies between 1,000,000 and 1,000). Three specific dissociation constants are considered $K_D$, and non-specific PCCFs are computed by letting $K_D \to \infty$. All parameters other than $K_D$, n, and $N_i$ are assigned the following fixed values consistent with literature and experimental data.

| | |
|---|---|
| $P_\# = 20$ pmol/100 μL | Approximate values which can be used in the assay |
| $R_\# = 200$ pmol/100 μL | |
| $R^0 = 100$ nM | |
| $A = 75 \times 25$ mm² | Standard microscope slide area |
| $r = 0.7$ μm | Co-localization threshold distance used in our experiments |
| $\alpha = 0.8$ | Approximate values based on the ACP functional assay |
| $\tau = 0.8$ | |
| $U = 10$ μM | Assumed non-specific protein-probe complex dissociation constant |
| $\beta = 0.75$ | Refer to (3) |
| $\gamma = 0.75$ | |

Figure 17:
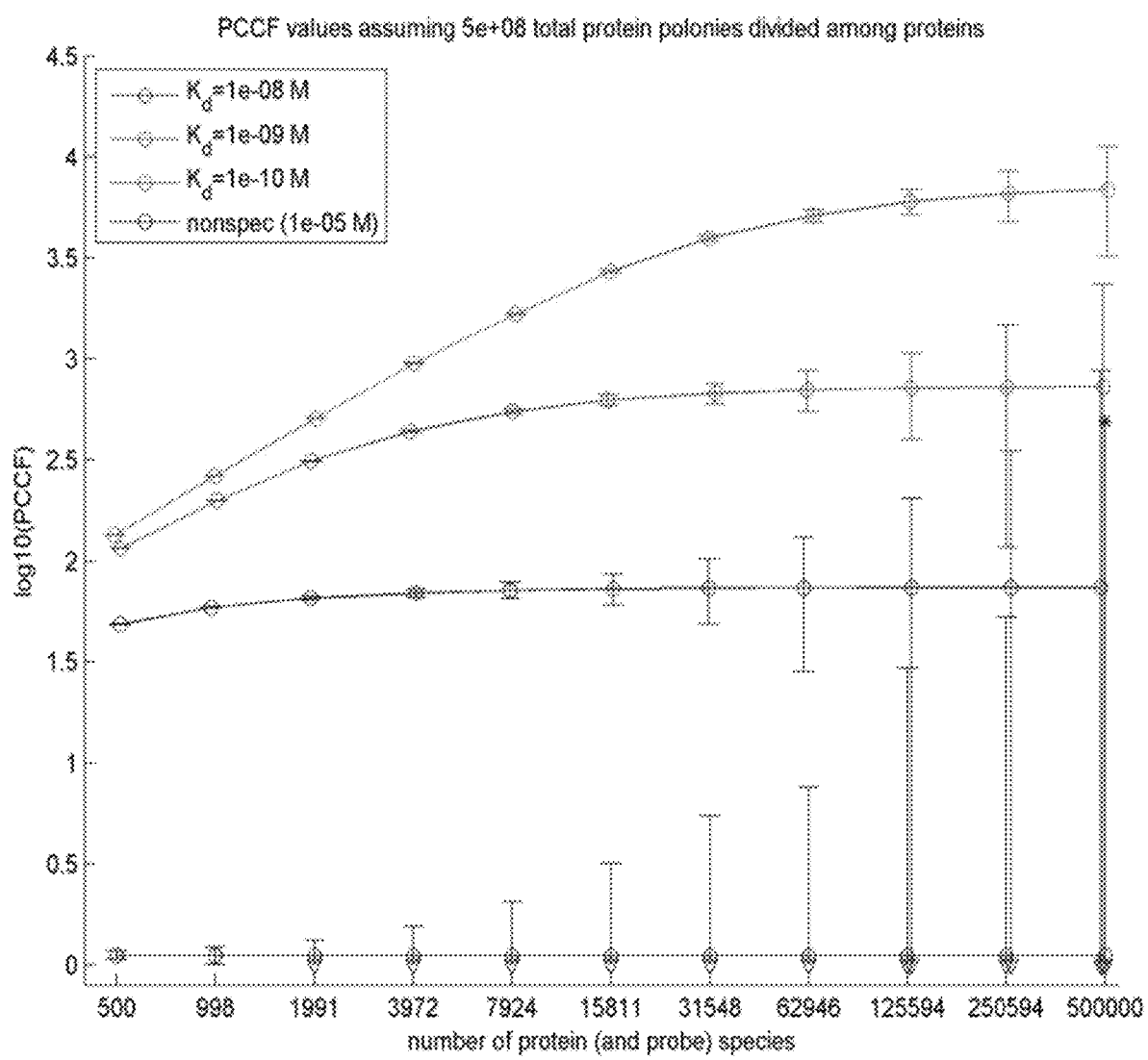
FIG. 17 graphically depicts simulation results of the mathematical modeling for a protein library vs. a probe library screening in a single assay. The mathematical modeling description provides additional details.

Results are summarized in FIG. 17. In FIG. 17, error bars span the range of the 1st and 99th percentiles of randomly simulated PCCF distributions as described above, with the following exception(s): (i) For large values of n, the 99th percentile of the non-specific PCCF distribution was no more than the central value computed by the model so that the upper error bar could be at or below the central value. In these cases the maximum value observed in the PCCF distribution was used to set the upper error bar instead of the 99th percentile, and the upper end of the error bar was marked with an asterisk (*). This situation arises because the number of $P_i$ and $R_i$ polonies becomes very small so that simulations result in no or very few co-localized polonies except for a small number of outliers. (ii) Because PCCFs are presented below via their log 10 values, PCCF values of 0 cannot be portrayed directly. However, in some cases the 1st percentiles of PCCF values were 0, and this is indicated by the use of a downward pointing arrowhead on the lower error bars. Note that markers and error bars are slightly jittered in order to allow overlapping error bars to be seen clearly. For each set of $K_D$, n, and $N_i$ values, 10,000 random simulations were performed.

A conclusion that may be drawn from these simulations is that order-of-magnitude differences between specific $K_D$s can be clearly distinguished from each and from non-specific binding in mixtures of up to ~63,000 distinct protein and probe species under the conditions assumed in the model. Note, however, that while the lack of overlap between error bars that indicate 1st and 99th percentiles implies that the PCCF distributions for these different KDs overlap with P<0.0001, these probabilities are not corrected for multiple hypotheses.

REFERENCES IN THIS EXAMPLE (1) Philimonenko et al. (2000) J. Struct. Biol. 132:201
(2) Hanisch and Stoyan (1979) Math. Operationsforsch. Statist., Ser. Statitics 14:559
(3) Mitra and Church (1999) Nucleic Acids Res. 27:e34

EXAMPLE VII

Methods

DNA Construction

Figure 10:
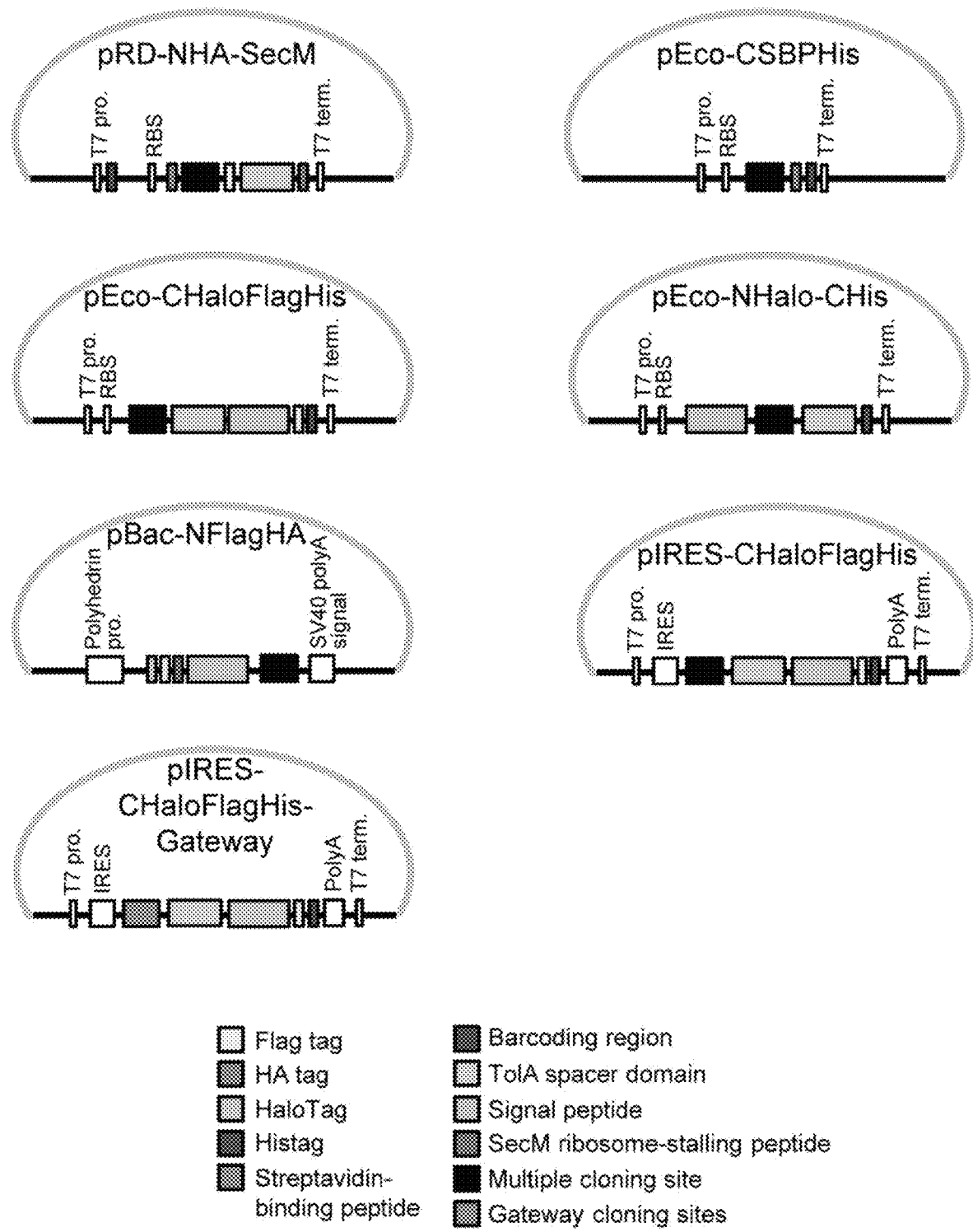
FIG. 10 schematically depicts Expression vectors described herein. pRD-NHA-SecM, the vector for ribosome display; pEco-CSBPHis, pEco-CHaloFlagHis and pEco-NHalo-CHis, vectors for E. coli in vivo and in vitro protein expression; pBac-NFlagHA, the Baculovirus expression vector for GPCRs; pIRES-CHaloFlagHis and pIRES-CHaloFlagHis-Gateway, vectors for expression of fusion proteins in the human IVT system. Refer to FIG. 16 for their DNA sequences.

Protein coding sequences were synthesized (Genewiz and IDT), PCR amplified from plasmids or genomic DNA, or transferred from Gateway-adapted human ORF clones31 (refer to FIG. 15 for DNA sources, sequences and construction methods), and inserted into expression vectors containing a multiple cloning site or Gateway recombination sites (refer to FIG. 10 for plasmid construction and FIG. 16 for plasmid and primer sequences) for in vitro or in vivo protein translation.

Ribosome Display-Based Protein Barcoding

For protein libraries of relatively small size (e.g., ≤200 in this work), a barcoding sequence can be introduced to DNA templates by performing individual PCR reactions with a barcoded primer. Barcoded linear DNA templates were pooled and in vitro transcribed using a HiScribe T7 kit (NEB). Transcribed mRNAs were treated with a DNA-free kit (Ambion), purified with an RNeasy Mini kit (Qiagen) and quantified by Nanodrop 1000 (Thermo Scientific). To generate mRNA-cDNA hybrids, cDNAs were synthesized by incubating ~0.10 µM mRNA, 1 µM 5'-acrydite and desthiobiotin-modified primer, 0.5 mM each dNTP, 10 U/µL SuperScript III, 2 U/µL RNaseOUT (Invitrogen) and 5 mM dithiothreitol (DTT) in a buffer (50 mM Tris-HCl, pH 8.3, 75 mM KCl, and 5 mM MgCl2) at 50° C. for ~30 min. Resultant mRNA-cDNA hybrids were enriched by isopropanol precipitation and purified with streptavidin-coated magnetic beads (Dynabeads M-270 Streptavidin, Life Technologies). A PURExpress Δ Ribosome kit (NEB) was applied to display proteins on $E.$ $coli$ ribosomes. Typically, a 250 µL IVT reaction with ~0.40 µM mRNA-cDNA hybrids and ~0.30 µM ribosome was incubated at 37° C. for 30 min, quenched by addition of 250 µL ice-cold buffer HKM (50 mM HEPES, pH 7.0, 250 mM KOAc, 25 mM Mg(OAc)2, 0.25 U/mL RNasin (Promega), 0.5 mg/mL chloramphenicol, 5 mM 2-mercaptoethanol and 0.1% (v/v) Tween 20) and centrifuged (14,000 g, 4° C.) for 10 min to remove insoluble components. PRMC complexes, always kept on ice or in cold room, were subjected to two-step Flag tag and desthiobiotin tag affinity purification to enrich full-length and barcoded target proteins. Thus, proteins were sequentially purified using anti-Flag M2 (Sigma-Aldrich) and the streptavidin magnetic beads, which were blocked with the buffer HKM supplemented with 100 µg/mL yeast tRNA and 10 mg/mL BSA. The bound proteins were eluted with the buffer HKM containing 100 µg/ml Flag peptide or 5 mM biotin, and their barcoding DNAs were quantitated by real-time PCR.

Protein Expression and Purification and HaloTag-Based Barcoding

His-tagged HaloTag-TolA, HaloTag-DsRed-TolA, Ras-TolA-HaloTag and β-arr2-TolA-HaloTag were expressed in $E.$ $coli$ or using an $E.$ $coli$ IVT system for relatively large or small-scale production. Proteins were expressed in an OverExpress C41(DE3) strain (Lucigen) with 1 mM isopropyl-D-D-galactopyranoside (IPTG) induction at 30° C. for 8-10 h and purified using immobilized metal affinity chromatography (IMAC) at 4° C. In brief, harvested cells were resuspended in a lysis buffer (50 mM sodium phosphate, pH 8.0, 300 mM NaCl, 10 mM imidazole and 20% glycerol) and disrupted by French press. Supernatants of cell lysates were loaded on a 5 ml HisTrap column (GE Healthcare) and non-specifically bound components were washed off with a buffer (50 mM sodium phosphate, pH 8.0, 300 mM NaCl, 20 mM imidazole and 10% glycerol). His-tagged proteins were eluted with a buffer (50 mM sodium phosphate, pH 8.0, 300 mM NaCl, 250 mM imidazole and 10% glycerol), concentrated with Amicon Ultra-15 centrifugal filter units (Millipore), buffer exchanged to a storage buffer (50 mM HEPES, pH 7.0, 150 mM KOAc and 20% glycerol) using a PD10 desalting column (GE Healthcare), flash frozen in 100-500 DL aliquots by liquid N2 and stored at −80° C. Relatively small amounts of proteins were synthesized in an $E.$ $coli$ crude extract (RTS 100 $E.$ $coli$ HY, 5 PRIME) at 30° C. for 4 h, and similarly purified with His-tag magnetic beads (Dynabeads His-tag, Life Technologies).

Human ADRB2, CHRM1 and CHRM2 were expressed in baculovirus-infected Sf9 cells (Life Technologies) and solubilized with detergents similarly as previously described32, 33. To reduce protein denaturation during purification, a recently developed method was followed in which solubilized GPCRs are immediately assembled into GPCR-nanodisc complexes before affinity purification34. Briefly, synthesized GPCR genes were inserted into a pBac-NFlagHA vector and thus GPCRs were expressed as a fusion protein bearing an N-terminal Flag and a HA tag and a HaloTag. Cells were harvested at two days after transfection, homogenized in a lysis buffer (50 mM Tris-HCl, pH 7.4, 50 mM NaCl and 1 mM EDTA) supplemented with a protease inhibitor (PI) cocktail (Roche) and centrifuged to collect the membrane fractions. The membranes were solubilized in a solubilization buffer (50 mM Tris-HCl, pH 7.4, 150 mM NaCl, 5 mM CaCl2), 5 mM MgCl2, 2 mM EDTA, 10% glycerol and 1% n-dodecyl-β-d-maltopyranoside (DDM)) supplemented with a PI cocktail (Set III, EMD Biosciences) and centrifuged at 15,000 g for 15 min; the supernatants were subjected to a bicinchoninic acid assay (Thermo Scientific) to determine protein concentration. The nanodiscs were assembled by incubating 90 µM MSP1E3D1 (Sigma-Aldrich), 8 mM POPC, 40 mM DDM and 180 µg total membrane protein in a reconstitution buffer (50 mM Tris pH 7.4, 150 mM NaCl, 5 mM CaCl2), 5 mM MgCl2, 2 mM EDTA and 2% glycerol) on ice for 45 min, followed by removal of the detergent using Bio-Beads SM-2 (Bio-Rad) 34. GPCR-nanodisc complexes were bound to anti-Flag M1 agarose resin (Sigma-Aldrich) and eluted with a conjugation buffer C1 (50 mM HEPES, pH 7.5, 150 mM NaCl, 2 mM EDTA and 5% glycerol) in the presence of 0.2 mg/mL Flag peptide. Ligand binding activities of purified GPCRs were measured by a time-resolved fluorescence resonance energy transfer assay (Cisbio Bioassays), in which the HaloTagged GPCRs were labelled with HaloTag-terbium cryptate (Lumi4-Tb) and interacted with fluorescent ligands, L0011GRE (ADRB2 antagonist) and L0040RED (CHRM1 and CHRM2 agonist).

Human protein genes were sub-cloned into pIRES-CHaloFlagHis or pIRES-CHaloFlagHis-Gateway containing an internal ribosome entry site (IRES) for in vitro protein synthesis with a human IVT kit (Thermo Scientific). Proteins were translated at 30° C. for 2 h and purified with the anti-Flag M2 or His-tag magnetic beads. Membrane proteins were stabilized by addition of preassembled nanodiscs (2 µL MembraneMax reagent/50 µL reaction, Life Technologies). HaloTag fusion proteins can be semi-quantitatively analyzed by in-gel fluorescence detection. Thus, HaloTag domains were covalently labeled with a fluorescent reporter HaloTMR (Promega) and subsequently analyzed by SDS-PAGE and fluorescent gel imaging with a Typhoon Trio Imager (GE Healthcare).

220-bp double stranded barcoding DNAs were prepared in parallel by PCR amplification with a universal template (FIG. 16) and one primer bearing a barcoding sequence. Modifications of desthiobiotin, acrydite and HaloTag ligand were introduced by a secondary PCR with the modified primers. A HaloTag ligand was conjugated to the primer by incubating the amino modified oligo (100 µM) and 5 mM succinimidyl ester (04) ligand (Promega) in a conjugation buffer C2 (50 mM Na2HPO4, pH 8.0 and 150 mM NaCl) at room temperature for 1 h; the modified oligo was purified by reverse-phase high-performance liquid chromatography using a Source 15RPC column (GE Healthcare) and an elution gradient of 3-70% CH3CN/H2O (0.1 M triethylamine acetate). To generate protein-DNA conjugates, we typically incubated equal molar amounts (e.g., ~0.5 µM) of modified barcoding DNAs and HaloTagged proteins in the conjugation buffer C1 with gentle shaking at room temperature for 4-6 h; the conjugates were purified with the anti-Flag M2 or His-tag and then the streptavidin magnetic beads.

Barcoded proteins can be eluted in corresponding assay buffers (see below) in the presence of 5 mM biotin.

Ras-Raf-RBD Binding Assay

Prior to the barcoding, the *E. coli* expressed and purified Ras protein was saturated with a non-hydrolyzable GTP analog, Gpp(NH)p, by EDTA-enhanced nucleotide exchange as previously described35. 2 nM mixed Raf-RBD WT and mutants displayed on PRMC complexes were incubated with different concentrations of barcoded Ras in an assay buffer A1 (50 mM HEPES, pH 7.5, 100 mM NaCl, 10 mM MgCl2, 0.5 mM DTT and 0.1% (v/v) Tween 20) in the presence of 0.5 mM Gpp(NH)p for 1 h. After reaching equilibrium, Ras-Raf-RBD complexes were crosslinked with 0.5 mM BS(PEG)5 at 4° C. for 1 h. The reaction was quenched by adding Tris-HCl, pH 8.0 to a final concentration of 50 mM. Free barcoded Ras protein can contribute to random Raf-RBD polony co-localization which affects accuracy of the measurement, and thus was removed by affinity purification to enrich HA-tagged Raf-RBD proteins. Thus, the samples were incubated with anti-HA magnetic beads (Thermo Scientific) at 4° C. for ~2 h and eluted with an array deposition buffer (20 mM HEPES, pH 7.0, 50 mM KOAc, 6 mM Mg(OAc)2, 0.5 mg/mL chloramphenicol, 0.25 U/mL RNasin (Promega) and 0.1% Tween 20) in the presence of 2 mg/mL HA peptide.

GPCR Profiling Assay

Mixed barcoded GPCRs were assayed with 100 µM alprenolol, pindolol, isoproterenol, atropine and carbachol (Sigma-Aldrich) and 100 nM xanomeline (Tocris Bioscience). A GPCR-β-arr2 binding assay was performed by mixing a ligand with ~1 nM GPCR-nanodisc complexes in an assay buffer A2 (20 mM HEPES, pH 7.5, 50 mM KOAc, 2 mM EDTA and 5 mM MgCl2), followed by addition of 10 nM GRK2 (Life Technologies), 0.1 mM ATP, 10 nM G protein β1γ2 subunits (KeraFAST) and 5 nM barcoded β-arr2 in a total volume of 25 µL. Compounds were assayed in parallel using a multi-well plate, and the reactions were incubated at 30° C. for 30 min. Similarly as described above, GPCR-β-arr2 complexes were crosslinked and both crosslinked and free GPCRs were purified from the reactions with the anti-HA magnetic beads. Proteins were pooled and analyzed on a single array.

ScFv Binding Profiling and Immunoprecipitation Assay

Error-prone PCR was performed for ten scFv genes previously synthesized10 by using a random mutagenesis kit (Clontech) at the condition of 3.5 mutations per 1,000 bp. Twenty mutants for each scFv were randomly picked and pooled to constructed a scFvs library. Ribosome display of the scFv library was specifically performed with the PURExpress Δ Ribosome kit supplemented with disulfide bond enhancers (NEB, 10 µL of the enhancer 1 and 2 for a 250 µL reaction). The binding assay was performed by incubating scFvs (~5.5 nM) and mixed barcoded human proteins (~1.8 µM) in a buffer A3 (50 mM HEPES, pH 7.5, 100 mM NaCl, 10 mM MgCl2 and 0.1% (v/v) Tween 20) at 4° C. for 4 h. Similarly as above, scFv-human protein complexes were crosslinked and HA-tagged scFvs in free and bound forms were enriched by the anti-HA magnetic beads and eluted in the buffer HKM.

For the immunoprecipitation assay, selected scFv genes were subcloned into pEco-CSBP and the scFv fusions bearing a C-terminal SBP tag were in vitro synthesized using a PURExpress IVT kit (NEB) supplemented with the disulfide bond enhancers. In each binding assay, a 10 µL IVT reaction (typically containing 0.1-0.4 µM translated scFvs) was incubated with 2 µL human protein (4.6-9.5 nM) labelled by Halo-TMR in the buffer A3 at 4° C. for 4 h. ScFvs and bound human proteins were pulled down with the streptavidin magnetic beads and then analyzed by SDS-PAGE and fluorescence gel imaging.

Array Deposition

Barcoded proteins were diluted with the deposition buffer to a 10× deposition concentration between 0.1 to 1 nM. Because the presence of oxygen can inhibit the gel polymerization, a gel-casting solution (6.66% acrylamide/bis-acrylamide (19:1, molecular grade, Ambion) and two 5'-acrydite-modified bridge amplification primers (111 M each) in the deposition buffer) were degassed with argon and mixed with diluted proteins by a 9:1 volume ratio in an anaerobic chamber (Coy Lab). To form a gel layer of less than 5-µm thickness, ~20 µL of the gel-casting mix, immediately after addition of 0.1% (v/v) TEMED and 0.05% (w/v) ammonium persulfate, was applied to a glass microscope slide surface pretreated with Bind-Silane (GE Healthcare)7,13, and a coverslip was placed on the top of the liquid and tightly pressed to form a liquid layer evenly spread over the glass surface. The gel was polymerized in the anaerobic chamber for 4 h. After removal of the coverslip, the slide was washed with Milli-Q H2O and dried by a quick spin.

Polony Amplification, Linearization and Blocking

The protein-loaded slide was assembled in a FC 81 transmission flow cell containing a 1.85-mm-thick polycarbonate flow channel (BioSurface Technologies), and thus reagents and buffers can be sequentially added in cycles for polony amplification, linearization and blocking. Flow cell components including the channel, a coverslip and tubing were sequentially cleaned by sonication in 5% Contrad 70, 1 M NaOH, 0.1 N HCl and Milli-Q H2O, and air dried in an AirClean PCR hood. Prior to the amplification, mRNAs can be digested with 10 U/mL RNase H (NEB) in a digesting buffer (50 mM Tris-HCl, pH 8.3, 75 mM KCl, 3 mM MgCl2 and 0.1% (v/v) Triton X-100) at 37° C. for 20 min. Polony amplification, linearization and blocking were performed similarly as a Illumina cluster generation protocol12. Typically, immobilized barcoding DNAs were subjected to 32-35 cycles of isothermal bridge amplification at 60° C. For each cycle, the flow cell was washed with deionized formamide (Ambion) and an amplification buffer (20 mM Tris-HCl, pH 8.8, 10 mM ammonium sulfate, 2 mM magnesium sulfate, 0.1% (v/v) Triton X-100, 1.3% (v/v) DMSO and 2M betaine) and incubated with 200 µM dNTPs and 80 U/mL Bst polymerase (NEB) in the amplification buffer for 5 min. Resulted double-stranded polonies were linearized by incubated the flow cell with 10 U/mL USER enzyme (NEB) in a linearization buffer (20 mM Tris-HCl, pH 8.8, 10 mM KCl, 10 mM ammonium sulfate, 2 mM magnesium sulfate and 0.1% (v/v) Triton X-100) at 37° C. for 1 h; excised strands were eluted with a wash buffer W1 (1×SSC and 70% formamide). Exposed 3'-OH ends of DNAs were blocked by incubating the flow cell for three times with M ddNTPs and 250 U/mL terminal transferase (NEB) in a blocking buffer (20 mM Tris-acetate, pH 7.9, 50 mM KOAc, 10 mM Mg(OAc)2 and 0.25 mM CoCl2) at 37° C. for 10 min.

DNA Sequencing

Linearized and 3'-OH blocked polonies were analyzed by hybridization with fluorescently labeled oligos, SBE or sequencing by ligation similarly as previously described13, 14. The assays can be performed within the flow cell or a gasket chamber assembled with the slide taken out of the flow cell and a microarray gasket slide (Agilent Technologies). Oligos (IDT) and dideoxynucleotides (PerkinElmer) were labelled by fluorescein/FAM, Cy3/Ty563 or Cy5/Ty665 for three-color imaging. Although four-color imaging is typical for DNA sequencing, only three channels were applied in our platform to minimize crosstalk between channels. In brief, polonies were hybridized with oligos (2 µM each) in a hybridization buffer (5×SSC and 0.1% (v/v) Tween 20) at 60° C. for 10 min, and the flow cell was cooled to 40° C. and washed with a wash buffer W2 (0.3×SSC and 0.1% (v/v) Tween 20). The SBE was performed by incubating primer-bound polonies with fluorescently labeled ddNTPs (1 µM each) and 0.32 U/µl Thermo Sequenase (GE Healthcare) in an extension buffer (26 mM Tris-HCl, pH 9.5, 6.5 mM MgCl2 and 0.05% (v/v) Tween 20) at 60° C. for 5 min; excess ddNTPs were removed with the wash buffer W2. For each sequencing-by-ligation cycle, sequencing primer-bound polonies were probed with a query primer set (fluorescent nonamers, 2 µM each subpool) in a ligation buffer (50 mM Tris-HCl, pH 7.6, 10 mM MgCl2, 1 mM ATP and 5 mM DTT) in the presence of 30 U/µl T4 DNA ligase (Enzymatics). The ligation was incubated at room temperature for 20 min, then increased to 35° C. and stayed for 40 min. Before the next cycle, the hybridized primers were stripped with the buffer W1 at 60° C., followed by wash with the buffer W2. To facilitate deconvolution of co-localized polonies from two protein libraries, each library was separately sequenced by using a distinct sequencing primer.

Image Acquisition, Processing and Base Calling

Fluorescence imaging was conducted with a Leica AM TIRF MC system including a DMI6000 B inverted microscope, a motorized scanning stage and a Hamamatsu C9100-02 electron multiplying CCD camera (1000×1000 pixels, Hamamatsu Photonics). Polony images were acquired under an epi-illumination mode by using a 20× objective (HCX PL Fluotar L, N.A. 0.40, Leica) or 40× (HCX PL APO, N.A. 0.85, Leica) and from three channels (fluorescein, Cy3 and Cy5) using, respectively, 488, 561 and 635 nm lasers and excitation-emission filter pairs of 490/20-525/50, 552/24-605/65 and 635/10-720/60, respectively. Raw images were exported by LAS AF Lite software (Leica) and processed using ImageJ and MATLAB (R2011a) scripts to remove background fluorescence and exclude small-size impurities and large-scale structures. Image analyses and base calling were conducted similarly as previously described14. In brief, MATLAB scripts were applied to identify polony coordinates by finding local maxima or weighted centroids, construct a reference image containing all detected polonies by super-imposing images taken in the first cycle, and align images from later cycles to the reference image. Thus, a set of fluorescence values for each acquisition cycle as well as the coordinates were obtained for barcode identification and polony co-localization analyses. Given programmable synthetic barcodes, only a few sequencing cycles were required for the protein libraries used in this work (e.g., 5 cycles for the library of 200 scFvs barcoded by a 5-bp sequence composed of A, T and C).

Co-Localization Analysis and Statistics

To align reference images of two protein libraries, polonies were hybridized with both sequencing primers labelled by Cy3 or Cy5, and thus their images were super-imposed to serve as a cross-library reference. MATLAB scripts calculated the offset of reference images generated from two sequencing rounds, measured distances between all polony positions identified from the two libraries, and compared them to a defined threshold to determine the co-localization. A polony exclusion effect36,37 was considered usually observed for competitive co-amplification of co-localized templates, and an optimized threshold distance was set to be 0.7 µm. Total and co-localized polony numbers were computed for each paired polony species at each imaging position. Co-localization statistics were calculated using Student's t-tests based on measurements at all imaged positions. In addition, a pair cross-correlation function (PCCF) statistic38 was applied to compare observed with random polony co-localization and study their co-localization patterns.

EXAMPLE VIII

REFERENCES

1 Shendure, J. & Ji, H. Next-generation DNA sequencing. Nat. Biotechnol. 26, 1135-1145 (2008).
2 Dreze, M. et al. High-quality binary interactome mapping. Methods Enzymol. 470, 281-315 (2010).
3 MacBeath, G. & Schreiber, S. L. Printing proteins as microarrays for high-throughput function determination. Science 289, 1760-1763 (2000).
4 Gavin, A. C. et al. Functional organization of the yeast proteome by systematic analysis of protein complexes. Nature 415, 141-147 (2002).
5 Weiss, S. Fluorescence spectroscopy of single biomolecules. Science 283, 1676-1683 (1999).
6 Hanes, J. & Pluckthun, A. In vitro selection and evolution of functional proteins by using ribosome display. Proc. Natl. Acad. Sci. U.S.A. 94, 4937-4942 (1997).
7 Mitra, R. D. & Church, G. M. In situ localized amplification and contact replication of many individual DNA molecules. Nucleic Acids Res. 27, e34 (1999).
8 Shimizu, Y. et al. Cell-free translation reconstituted with purified components. Nat. Biotechnol. 19, 751-755 (2001).
9 Tian, J. D. et al. Accurate multiplex gene synthesis from programmable DNA microchips. Nature 432, 1050-1054 (2004).
10 Kosuri, S. et al. Scalable gene synthesis by selective amplification of DNA pools from high-fidelity microchips. Nat. Biotechnol. 28, 1295-U1108 (2010).
11 Los, G. V. et al. HatoTag: A novel protein labeling technology for cell imaging and protein analysis. ACS Chem. Biol. 3, 373-382 (2008).
12 Bentley, D. R. et al. Accurate whole human genome sequencing using reversible terminator chemistry. Nature 456, 53-59 (2008).
13 Mitra, R. D. et al. Digital genotyping and haplotyping with polymerase colonies. Proc. Natl. Acad. Sci. U.S.A. 100, 5926-5931 (2003).
14 Shendure, J. et al. Accurate multiplex polony sequencing of an evolved bacterial genome. Science 309, 1728-1732 (2005).
15 Heikal, A. A., Hess, S. T., Baird, G. S., Tsien, R. Y. & Webb, W. W. Molecular spectroscopy and dynamics of intrinsically fluorescent proteins: Coral red (dsRed) and yellow (Citrine). Proc. Natl. Acad. Sci. U.S.A. 97, 11996-12001 (2000).
16 Vetter, I. R. & Wittinghofer, A. Signal transduction—The guanine nucleotide-binding switch in three dimensions. Science 294, 1299-1304 (2001).
17 Block, C., Janknecht, R., Herrmann, C., Nassar, N. & Wittinghofer, A. Quantitative structure-activity analysis correlating Ras/Raf interaction in vitro to Raf activation in vivo. Nat. Struct. Biol. 3, 244-251 (1996).
18 Kiel, C. et al. Improved binding of raf to Ras.GDP is correlated with biological activity. J. Biol. Chem. 284, 31893-31902 (2009).
19 Overington, J. P., Al-Lazikani, B. & Hopkins, A. L. Opinion-How many drug targets are there?Nat. Rev. Drug Disc. 5, 993-996 (2006).

20 Zhang, R. & Xie, X. Tools for GPCR drug discovery. Acta Pharmacol. Sin. 33, 372-384 (2012).
21 Denisov, I. G., Grinkova, Y. V., Lazarides, A. A. & Sligar, S. G. Directed self-assembly of monodisperse phospholipid bilayer nanodiscs with controlled size. J. Am. Chem. Soc. 126, 3477-3487 (2004).
22 Leitz, A. J., Bayburt, T. H., Barnakov, A. N., Springer, B. A. & Sligar, S. G. Functional reconstitution of □2-adrenergic receptors utilizing self-assembling Nanodisc technology. Biotechniques 40, 601-610 (2006).
23 Whorton, M. R. et al. A monomeric G protein-coupled receptor isolated in a high-density lipoprotein particle efficiently activates its G protein. Proc. Natl. Acad. Sci. U.S.A. 104, 7682-7687 (2007).
24 Luttrell, L. M. & Lefkowitz, R. J. The role of □-arrestins in the termination and transduction of G-protein-coupled receptor signals. J. Cell Sci. 115, 455-465 (2002).
25 Gurevich, V. V. et al. Arrestin interactions with G-protein-coupled receptors—Direct binding-studies of wild-type and mutant arrestins with rhodopsin, □□-adrenergic, and m2-muscarinic cholinergic receptors. J. Biol. Chem. 270, 720-731 (1995).
26 Yu, H. et al. Next-generation sequencing to generate interactome datasets. Nat. Methods 8, 478-480 (2011).
27 Michaud, G. A. et al. Analyzing antibody specificity with whole proteome microarrays. Nat. Biotechnol. 21, 1509-1512 (2003).
28 Zhu, J. et al. Protein interaction discovery using parallel analysis of translated ORFs (PLATO). Nat. Biotechnol. 31, 331-334 (2013).
29 Kleiner, R. E., Dumelin, C. E. & Liu, D. R. Small-molecule discovery from DNA-encoded chemical libraries. Chemical Society Reviews 40, 5707-5717 (2011).
30 Lee, J., Daugharthy, E., Scheiman, J. & Church, G. M. Highly multiplexed subcellular RNA sequencing in situ. Science, in press (2014).
31 Rual, J. F., Hill, D. E. & Vidal, M. ORFeome projects: gateway between genomics and omics. Curr. Opin. Chem. Biol. 8, 20-25 (2004).
32 Parker, E. M., Kameyama, K., Higashijima, T. & Ross, E. M. Reconstitutively active G protein-coupled receptors purified from baculovirus-infected insect cells. J. Biol. Chem. 266, 519-527 (1991).
33 Kobilka, B. K. Amino and carboxyl terminal modifications to facilitate the production and purification of a G protein-coupled receptor. Anal. Biochem. 231, 269-271 (1995).
34 Mitra, N. et al. Calcium-Dependent Ligand Binding and G-protein Signaling of Family B GPCR Parathyroid Hormone 1 Receptor Purified in Nanodiscs. ACS Chem. Biol. 8, 617-625 (2013).
35 John, J., Frech, M. & Wittinghofer, A. Biochemical properties of Ha-ras encoded p21 mutants and mechanism of the autophosphorylation reaction. J. Biol. Chem. 263, 11792-11799 (1988).
36 Mitra, R. D., Shendure, J., Olejnik, J., Edyta Krzymanska, O. & Church, G. M. Fluorescent in situ sequencing on polymerase colonies. Anal. Biochem. 320, 55-65 (2003).
37 Aach, J. & Church, G. M. Mathematical models of diffusion-constrained polymerase chain reactions: basis of high-throughput nucleic acid assays and simple self-organizing systems. J. Theor. Biol. 228, 31-46 (2004).
38 Philimonenko, A. A., Janacek, J. & Hozak, P. Statistical evaluation of co-localization patterns in immunogold labeling experiments. J. Struct. Biol. 132, 201-210 (2000).

SEQUENCE LISTING

```
Sequence total quantity: 36
SEQ ID NO: 1              moltype = DNA  length = 4222
FEATURE                   Location/Qualifiers
misc_feature              1..4222
                          note = EXPRESSION VECTOR pRD-NHA-SecM
source                    1..4222
                          mol_type = other DNA
                          organism = synthetic construct
SEQUENCE: 1
ggatctcgat cccgcgaaat taatacgact cactataggg aatgatacgg cgaccaccga    60
ggggggggag agaatgagga acccgggaac aatgatgaa tccctaggtt ggcttaccaa   120
aaatgaagct gatgaatact ccctcaaaga caattgtcaa ccttacttgt ccattcctga   180
agaaatatta tatttataca acttacccat agaatcctat ttactaggaa aggaaaagcc   240
tcctatttat aaaaattgga tagagctttc tcaacaacag tggaatatca atgatagaac   300
aattgccgat ttattagatg gggtcttaat aataccatcg tatgccgtct tctgcttgtt   360
cccctctaga aataattttg tttaactta agaaggagat atatcgatgg cctaccccta   420
cgacgtgccc gactacgccc tggccaccac cgcgatcgcc atggaacata tggctagcga   480
attcgagctc aagcttggcg gcagcggcgg cggcagcggc ggcggcagcg gcgattataa   540
agatgatgat gataaaggcg gcgcgggcag cggcgcgggc agcggcagca gcactagtca   600
gaagcaagct gaagaggcgg cagcgaaagc ggccgaaagc gctaaagcga aggccgaagc   660
agatgctaaa gctgcggaag aagcagcgaa gaaagcggct gcagacgcaa agaaaaaagc   720
agaagcagaa gccgccaaag ccgcagccga agcgcagaaa aaagccgagg cagccgctgc   780
ggcactgaag aagaaagcgg aagcggcaga agcagctgca gctgaagcaa gaaagaaagc   840
ggcaactgaa gctgctgaaa aagccaaagc agaagctgca aagaaagcgg ctgctgaaaa   900
ggctgcagct gataagaaaa cggcagcaga gaaagctgca gccgacaaaa aagcagcaga   960
aaaagcggct gctgaaaagg cagcagctga taagaaagca gcggcagaaa aagccgccgc  1020
agacaaaaaa gcggcagcgg caaaagctgc agctgaaaaa gccgctgcag caaaagcggc  1080
cgcagaggca gatgatattt tcggtgagct ggcaaaattc agcacgcccg tctggataag  1140
ccaggcgcaa ggcatccgtg ctggccctac cgcacacctt actggtgtgc gggagcaact  1200
agcataaccc cttggggcct ctaaacgggt cttgagggggt ttttttgggat cctctagagt  1260
cgacctgcag gcatgcaagc tgatccggct gctaacaaag cccgaaagga agctgagttg  1320
gctgctgcca ccgctgagca ataactagca taaccccttg gggcctctaa acgggtcttg  1380
aggggttttt tgctgaaagg aggaactata tccggttcgc ttgctgtcca taaaaccgcc  1440
```

-continued

```
cagtctagct atcgccatgt aagcccactg caagctacct gctttctctt tgcgcttgcg    1500
ttttcccttg tccagatagc ccagtagctg acattcatcc ggggtcagca ccgtttctgc    1560
ggactggctt tctacgtgtt ccgcttcctt tagcagccct tgcgccctga gtgcttgcgg    1620
cagcgtgagc ttcaaaagaa ttgccagctg gggcgccctc tggtaaggtt gggaagccct    1680
gcaaagtaaa ctggatggct ttcttgccgc caagtactg atgcgcagg ggatcaagat      1740
ctgatcaaga gacaggatga cggtcgtttc gcatgcttga acaagatgga ttgcacgcag    1800
gttctccggc cgcttgggtg gagaggctat tcgctatga ctgggcacaa cagacaatcg     1860
gctgctctga tgccgccgtg ttccggctgt cagcgcaggg gcgcccggtt cttttttgtca   1920
agaccgacct gtccggtgcc ctgaatgaac tgcaggacga ggcacgcgg ctatcgtggc     1980
tggccacgac gggcgttcct tgcgcagctg tgctcgacgt tgtcactgaa gcgggaaggg   2040
actggctgct attgggcgaa gtgccggggc aggatctcct gtcatctcac cttgctcctg   2100
ccgagaaagt atccatcatg gctgatgcaa tgcggcggct gcatacgctt gatccggcta   2160
cctgcccatt cgaccaccaa gcgaaacatc gcatcgagcg agcacgcact cggatggaag   2220
ccggtcttgt cgatcaggat gatctgacg aagagcatca ggggctcgcg ccagccgaa     2280
tgttcgccag gctcaaggcg cgtatgccgg atggtgagga tctcgtcgtg actcatggcg   2340
atgcctgctt gccgaatatc atggtggaaa atggccgctt ttctggattc atcgactgtg   2400
gccggctggg tgtggcggac cgctatcagg acatagcgtt ggctaccgt gatattgctg    2460
aagagcttgg cggcgaatgg gctgaccgct tcctcgtgct ttacggtatc gccgctccg    2520
attcgcagcg catcgccttc tatcgccttc ttgacgagt cttctgagcg ggactctggg    2580
gttcgaaatg accgaccaag cgacgcccaa ccggtatcag ctcactcaaa ggcggtaata   2640
cggttatcca cagaatcagg gataacgca ggaaagaaca tgtgagcaaa aggccagcaa    2700
aaggccagga accgtaaaaa ggccgcgttg ctggcgtttt tccataggct ccgcccccct   2760
gacgagcatc acaaaaatcg acgctcaagt cagaggtggc gaaacccgac aggactataa   2820
agataccagg cgtttccccc tggaagctcc ctcgtgcgct ctcctgttcc gaccctgccg   2880
cttaccggat acctgtccgc ctttctccct tcggaagcg tggcgctttc tcatagctca    2940
cgctgtaggt atctcagttc ggtgtaggtc gttcgctcca agctgggctg tgtgcacgaa   3000
ccccccgttc agcccgaccg ctgcgcctta tccggtaact atcgtcttga gtccaacccg   3060
gtaagacacg acttatcgcc actggcagca gccactggta acaggattag cagagcgagg   3120
tatgtaggcg gtgctacaga gttcttgaag tggtggccta actacggcta cactagaagg   3180
acagtatttg gtatctgcgc tctgctgaag ccagttacct tcggaaaaag agttggtagc    3240
tcttgatccg gcaaacaaac caccgctggt agcggtggtt ttttttgttg caagcagcag   3300
attacgcgca gaaaaaaagg atttcaagaa gatccttga tcttttctac ggggtctgac    3360
gctcagtgga acgaaaactc acgttaaggg attttggtca tgagattatc aaaaaggatc    3420
ttcacctaga tccttttata gtccggaaat acaggaaccgc acgtcggatg gcccttcgct  3480
gggatggtga aaccatgaaa aatggcagct tcagtggatt aagtggggt aatgtggct    3540
gtaccctctg gttgcatagg tattcatacg gttaaaattt atcaggcgcg attgcggcag   3600
ttttttcgggt ggtttgttgc catttttacc tgtctgctgc cgtgatcgcg ctgaacgcgt  3660
tttagcggtg cgtacaatta agggattatg gtaaatccac ttactgtctg ccctcgtagc   3720
catcgagata aaccgcagta ctccggccac gatgcgtccg gcgtagagga tcgagatctt   3780
ttcagcctga tacagattaa atcagaacgc agaagcggtc tgataaaaca gaatttgcct   3840
ggcggcagta gcgcggtggt cccacctgac cccatgccga actcagaagt gaaacgccgt   3900
agcgccgatg gtagtgtggg gtctcccat gcgagagtag ggaactgcca ggcatcaaat    3960
aaaacgaaag gctcagtcga aagactgggc ctttcgttt atctgttgtt tgtcggtgaa    4020
cgctctcctg agtaggacaa atccgccggg agcggatttg aacgttgcga agcaacggcc   4080
cggagggtgg cgggcaggac gcccgccata aactgccagg catcaaatta agcagaaggc   4140
catcctgacg gatggccttt ttgcgtttct acaaactctt tgtttatttt ttctaaatac   4200
attcaaatat gtatccgctc at                                             4222
```

SEQ ID NO: 2          moltype = DNA   length = 5372
FEATURE               Location/Qualifiers
misc_feature          1..5372
                      note = EXPRESSION VECTOR pEco-CSBP
source                1..5372
                      mol_type = other DNA
                      organism = synthetic construct
SEQUENCE: 2

```
agatctcgat cccgcgaaat taatacgact cactataggg gaattgtgag cggataacaa    60
ttcccctcta gaaataattt tgtttaactt taagaaggag atatacatat ggaattctta   120
attaagctgc aggagctcgt cgacgcggcc gcactcgaga agcttggcgg cagcggcatg   180
gacgagaaga ccaccggctg gcggggcggc cacgtggtgg agggcctggc cggcgagctg   240
gagcagctgc gggccaggct ggagcaccac cctcagggcc agcgggaggc cggcggcagc   300
ggccaccacc accaccacca ctgagctgag caataactag cataacccct ggggcctct    360
aaacgggtct tgaggggttt tttgctgaaa ggaggaacta tatccggatt ggcgaatggg   420
acgcgccctg tagcggcgca ttaagcgcgg cgggtgtggt ggttacgcgc agcgtgaccg   480
ctacacttgc cagcgcccta gcgcccgctc cttttcgctt ttctccttcc tttctcgcca   540
cgttcgccgg ctttccccgt caagctctaa atcgggggct ccctttaggg ttccgattta   600
gtgctttacg gcacctcgac cccaaaaaac ttgattaggg tgatggttca cgtagtgggc   660
catcgccctg atagacggtt tttcgccctt tgacgttgga gtccacgttc tttaatagtg   720
gactcttgtt ccaaactgga acaacactca accctatctc ggtctattct tttgatttat   780
aagggatttt gccgatttcg gcctattggt taaaaatga gctgatttaa caaaaattta   840
acgcgaattt taacaaaata ttaacgttta caatttcagg tggcactttt cggggaaatg   900
tgcgcggaac ccctatttgt ttatttttct aaatacattc aaatatgtat ccgctcatga   960
attaattctt agaaaaactc atcgagcatc aaatgaaact gcaattatt catatcagga   1020
ttatcaatac catatttaatg aaaaagccgt ttctgtaatg aaggagaaaa ctcaccgagg   1080
cagttccata ggatggcaag atcctggtat cggtctgcga ttccgactcg tccaacatca   1140
atacaaccta ttaatttccc ctcgtcaaaa ataaggttat caagtgagaa atcaccatga   1200
gtgacgactg aatccggtga gaatggcaaa agtttatgca tttctttcca gacttgttca   1260
acaggccagc cattacgctc gtcatcaaaa tcactcgcat caaccaaacc gttattcatt   1320
cgtgattgcg cctgagcgag acgaaatacg cgatcgctgt taaaaggaca attacaaaca   1380
```

-continued

```
ggaatcgaat gcaaccggcg caggaacact gccagcgcat caacaatatt ttcacctgaa  1440
tcaggatatt cttctaatac ctggaatgct gttttcccgg ggatcgcagt ggtgagtaac  1500
catgcatcat caggagtacg gataaaatgc ttgatggtcg gaagaggcat aaattccgtc  1560
agccagttta gtctgaccat ctcatctgta acatcattgg caacgctacc tttgccatgt  1620
ttcagaaaca actctggcgc atcgggcttc ccatacaatc gatagattgt cgcacctgat  1680
tgcccgacat tatcgcgagc ccatttatac ccatataaat cagcatccat gttggaattt  1740
aatcgcggcc tagagcaaga cgtttcccgt tgaatatggc tcataacacc ccttgtatta  1800
ctgtttatgt aagcagacag ttttattgtt catgaccaaa atcccttaac gtgagttttc  1860
gttccactga gcgtcagacc ccgtagaaaa gatcaaagga tcttcttgag atccttttt  1920
tctgcgcgta atctgctgct tgcaaacaaa aaaaccaccg ctaccagcgg tggtttgttt  1980
gccggatcaa gagctaccaa ctctttttcc gaaggtaact ggcttcagca gagcgcagat  2040
accaaatact gtccttctag tgtagccgta gttaggccac cacttcaaga actctgtagc  2100
accgcctaca tacctcgctc tgctaatcct gttaccagtg gctgctgcca gtggcgataa  2160
gtcgtgtctt accgggttgg actcaagacg atagttaccg gataaggcgc agcggtcggg  2220
ctgaacgggg ggttcgtgca cacagcccag cttggagcga acgacctaca ccgaactgag  2280
atacctacag cgtgagctat gagaaagcgc cacgcttccc gaaggagaa aggcggacag  2340
gtatccggta agcggcaggg tcggaacagg agagcgcacg agggagcttc caggggggaaa  2400
cgcctggtat ctttatagtc ctgtcgggtt tcgccacctc tgacttgagc gtcgatttt  2460
gtgatgctcg tcagggggc ggagcctatg gaaaaacgcc agcaacgcgg cctttttacg  2520
gttcctggcc ttttgctggc cttttgctca catgttcttt cctgcgttat cccctgattc  2580
tgtgataac cgtattaccg cctttgagtg agctgatacc gctcgccgca gccgaacgac  2640
cgagcgcagc gagtcagtga gcgaggaagc ggaagagcgc ctgatgcggt attttctcct  2700
tacgcatctg tgcggtattt cacaccgcat atatggtgca ctctcagtac aatctgctct  2760
gatgccgcat agttaagcca gtatacactc cgctatcgct acgtgactgg gtcatggctg  2820
cgccccgaca cccgccaaca cccgctgacg cgccctgacg ggcttgtctg ctcccggcat  2880
ccgcttacag acaagctgtg accgtctccg ggagctgcat gtgtcagagg ttttcaccgt  2940
catcaccgaa acgcgcgagg cagctgcggt aaagctcatc agcgtggtcg tgaagcgatt  3000
cacagatgtc tgcctgttca tccgcgtcca gctcgttgag tttctccaga agcgttaatg  3060
tctggcttct gataaagcgg gccatgttaa gggcggtttt ttcctgtttg gtcactgatg  3120
cctccgtgta agggggattt ctgttcatgg gggtaatgat accgatgaaa cgagagagga  3180
tgctcacgat acgggttact gatgatgaac atgcccggtt actggaacgt tgtgagggta  3240
aacaactggc ggtatggatg cggcgggacc agagaaaaat cactcagggt caatgccagc  3300
gcttcgttaa tacagatgta ggtgttccac agggtagcca gcagcatcct gcgatgcaga  3360
tccgaaacat aatggtgcag ggcgctgact tccgcgtttc cagactttac gaaacacgga  3420
aaccgaagac cattcatgtt gttgctcagg tcgcagacgt tttgcagcag cagtcgcttc  3480
acgttcgctc gcgtatcggt gattcattct gctaaccagt aaggcaaccc cgccagccta  3540
gccgggtcct caacgacagg agcacgatca tgcgcacccg tggggccgcc atgccggcga  3600
taatggcctg cttctcgccg aaacgtttgg tggcgggacc agtgacgaag gcttgagcga  3660
gggcgtgcaa gattccgaat accgcaagcg acaggccgat catcgtcgcg ctccagcgaa  3720
agcggtcctc gccgaaaatg acccagagcg ctgccggcac ctgtcctacg agttgcatga  3780
taaagaagac agtcataagt gcggcgacga tagtcatgcc ccgcgcccac cggaaggagc  3840
tgactgggtt gaaggctctc aagggcatcg gtcgagatcc cggtgcctaa tgagtgagct  3900
aacttacatt aattgcgttg cgctcactgc ccgctttcca gtcgggaaac ctgtcgtgcc  3960
agctgcatta atgaatcggc caacgcgcgg ggagaggcgg tttgcgtatt gggcgccagg  4020
gtggtttttc ttttcaccag tgagacgggc aacagctgat tgcccttcac cgcctggccc  4080
tgagagagtt gcagcaagcg gtccacgctg gtttgcccca gcaggcgaaa atcctgtttg  4140
atggtggtta acggcgggat ataacatgag ctgtcttcgg tatcgtcgta tcccactacc  4200
gagatatccg caccaacgcg cagcccggac tcggtaatgg cgcgcattgc gcccagcgcc  4260
atctgatcgt tggcaaccag catcgcagtg gaacgatgc cctcattcag catttgcatg  4320
gtttgttgaa aaccggacat ggcactccag tcgccttccc gttccgctat cggctgaatt  4380
tgattgcgag tgagatattt atgccagcca gccagacgca gacgcgccga gacagaactt  4440
aatgggcccg ctaacagcgc gatttgctgg tgacccaatg cgaccagatg ctccacgccc  4500
agtcgcgtac cgtcttcatg ggagaaaata atactgttga tgggtgtctg gtcagagaca  4560
tcaagaaata acgccggaac attagtgcag gcagcttcca cagcaatggc atcctggtca  4620
tccagcggat agttaatgat cagcccactg acgcgttgcg cgagaagatt gtgcaccgcc  4680
gctttacagg cttcgacgcc gcttcgttct accatcgaca ccaccacgct ggcacccagt  4740
tgatcggcgc gagatttaat cgccgcgaca atttgcgacg cgcgtgcag ggccagactg  4800
gaggtggcaa cgccaatcag caacgactgt ttgcccgcca gttgttgtgc cacgcggttg  4860
ggaatgtaat tcagctcgc catcgccgct tccacttttt cccgcgtttt cgcagaaacg  4920
tggctggcct ggttcaccac gcgggaaacg gtctgataag agacaccggc atactctgcg  4980
acatcgtata acgttactgg tttcacattc accaccctga attgactctc ttccgggcgc  5040
tatcatgcca taccgcgaaa ggttttgcgc cattcgatgg tgtccgggat ctcgacgctc  5100
tcccttatgc gactcctgca ttaggaagca gcccagtagt aggttgaggc cgttgagcac  5160
cgccgccgca aggaatggtg catgcaagga ggtggcgcc aacagtcccc ggccagtgg  5220
gcctgccacc atacccacgc cgaaacaagc gctcatgagc ccgaagtggc gagcccgatc  5280
ttccccatcg gtgatgtcgg cgatataggc gccagcaacc gcacctgtgg cgccggtgat  5340
gccgccacg atgcgtccgg cgtagaggat cg                                5372
```

| | | |
|---|---|---|
| SEQ ID NO: 3 | moltype = DNA  length = 6449 | |
| FEATURE | Location/Qualifiers | |
| misc_feature | 1..6449 | |
| | note = EXPRESSION VECTOR pEco-CHaloFlagHis | |
| source | 1..6449 | |
| | mol_type = other DNA | |
| | organism = synthetic construct | |

SEQUENCE: 3

```
agatctcgat cccgcgaaat taatacgact cactataggg gaattgtgag cggataacaa   60
ttcccctcta gaaataattt tgtttaactt taagaaggag atatacatat ggaattctta  120
attaagctgc aggagctcgt cgacgcggcc gcactcgaga agcttggcgg cagcggccag  180
```

```
aagcaagctg aagaggcggc agcgaaagcg gcggcagatg ctaaagcgaa ggccgaagca  240
gatgctaaag ctgcggaaga agcagcgaag aaagcggctg ccgacgcaaa gaaaaaagca  300
gaagcagaag ccgccaaagc cgcagccgaa gcgcagaaaa aagccgaggc agccgctgcg  360
gcactgaaga agaaagcgga agcggcagaa gcagctgccg ctgaagcaag aaagaaagcg  420
gcaactgaag gcggcagcgg catggctgag atcggcacgg gtttccccct cgaccccccac  480
tacgtggagg tgctgggtga gcgtatgcac tacgtggacg tgggtccccg tgacggcacc  540
cccgtgctgt tcctgcacgg taaccccacc tcctcctacg tgtggcgtaa catcatcccc  600
cacgtggctc ccacccaccg ttgcatcgct cccgacctga tcggtatggg taagtccgac  660
aagcccgacc tgggttactt cttcgacgac cacgtgcgtt tcatgdacgc tttcatcgag  720
gctctgggtc tggaggaggt ggtgctggtg atccacgact ggggtccgc tctgggtttc  780
cactgggcta agcgtaaccc cgagcgtgtg aagggtatcg ctttcatgga gttcatccgt  840
cccatcccca cctgggacga gtgggccgag ttcgctcgtg agaccttcca ggctttccgt  900
accaccgacg tgggtcgtaa gctgatcatc gaccagaaca tgttcatcga gggcaccctg  960
cctatgggtg tggtgcgtcc cctgaccgag gtggagatgg accactaccg tgagcccttc 1020
ctgaaccccg tggaccgtga gcccctgtgg cgtttcccca acgagctgcc catcgctggt 1080
gagcccgcta acatcgtggc tctggtggag gagtacatgg actggctgca ccagtccccc 1140
gtgcccaagc tgctgttctg gggcaccccc ggtgtgctga tccccccgc tgaggctgct 1200
cgtctggcta agtccctgcc caactgcaag gctgtggaca tcggtccccg tctgaacctg 1260
ctccaggagg acaaccccga cctgatcggt tccgagatcg ctcgttggct gtccaccctg 1320
gagatttccg tggtggttc cggtgattat aaagatgatg atgataaagg cggcgcgggc 1380
caccaccacc accaccactg agctgagcaa taactagcat aaccccttgg ggcctctaaa 1440
cgggtcttga ggggtttttt gctgaaagga ggaactatat cctggattgc gaatgggacg 1500
cgccctgtag cggcgcatta agcgcggcgg gtgtggtggt tacgcgcagc gtgaccgcta 1560
cacttgccag cgccctagcg cccgctcctt tcgctttctt cccttccttt ctcgccacgt 1620
tcgccggctt tccccgtcaa gctctaaatc ggggctccc tttagggttc cgatttagtg 1680
ctttacggca cctcgacccc aaaaaacttg attaggggtga tggttcacgt agtgggccat 1740
cgccctgata gacggttttt cgccctttga cgttggagtc cacgttcttt aatagtggac 1800
tcttgttcca aactgggaaca acactcaacc ctatctcggt ctattctttt gatttataag 1860
ggattttgcc gatttcggcc tattggttaa aaaatgagct gatttaacaa aaatttaacg 1920
cgaattttaa caaaatatta acgtttacaa tttcaggttgg cacttttcgg ggaaatgtgc 1980
gcggaacccc tatttgttta ttttttctaaa tacattcaaa tatgtatccg ctcatgaatt 2040
aattcttaga aaaactcatc gagcatcaaa tgaaactgca atttattcat atcaggatta 2100
tcaataccat attttgaaa aagccgtttc tgtaatgaag gagaaaactc accgaggcag 2160
ttccatagga tggcaagatc ctggtatcgg tctgcgattc cgactcgtcc aacatcaata 2220
caacctatta atttcccctc gtcaaaaata aggttatcaa gtgagaaatc accatgagtg 2280
acgactgaat ccggtgagaa tggcaaaagt ttatgcattt ctttccagac ttgttcaaca 2340
ggccagccat tacgctcgtc atcaaaatca ctcgcatcaa ccaaaccgtt attcattcgt 2400
gattgcgcct gagcgagacg aaatacgcga tcgctgttaa aaggacaatt acaaacagga 2460
atcgaatgca accggcgcag gaacactgcc agcgcatcaa caatattttc acctgaattca 2520
ggatattctt ctaatacctg gaatgctgtt ttcccgggga tcgcagtggt gagtaaccat 2580
gcatcatcag gagtacggat aaaatgcttg atggtcggaa gaggcataaa ttccgtcagc 2640
cagtttagtc tgaccatctc atctgtaaca tcattggcaa cgctaccttt gccatgtttc 2700
agaaacaact ctggcgcatc gggcttccca tacaatcgat agattgtcgc acctgattgc 2760
ccgacattat cgcgagccca tttatacccca tataaatcag catccatgtt ggaatttaat 2820
cgcggcctag agcaagacgt ttcccgttga atatggctca taacacccct tgtattactg 2880
tttatgtaag cagacagttt tattgttcat gaccaaaatc ccttaacgtg agttttcgtt 2940
ccactgagcg tcagacccg tagaaaagat caaaggatct cttgagatc ctttttttct 3000
gcgcgtaatc tgctgcttgc aaacaaaaaa accaccgcta ccagcggtgg tttgtttgcc 3060
ggatcaagag ctaccaactc ttttttccgaa ggtaactggc ttcagcagag cgcagatacc 3120
aaatactgtc cttctagtgt agccgtagtt aggccaccac ttcaagaact ctgtagcacc 3180
gcctacatac ctcgctctgc taatcctgtt accagtgctg gctgccagtg gcgataagtc 3240
gtgtcttacc gggttggact caagacgata gttaccggat aaggcgcagc ggtcgggctg 3300
aacgggggggt tcgtgcacac agcccagctt ggagcgaacg acctacaccg aactgagata 3360
cctacagcgt gagctatgag aaagcgccac gcttcccgaa gggagaaagg cggacaggta 3420
tccggtaagc ggcagggtcg gaacaggaga gcgcacgagg gagcttccag ggggaaacgc 3480
ctggtatctt tatagtcctg tcgggtttcg ccacctctga cttgagcgtc gatttttgtg 3540
atgctcgtca gggggggcgga gcctatgaaa aacgccagc aacgcggcct ttttacggtt 3600
cctggccttt tgctggcctt ttgctcacat gttctttcct gcgttatccc ctgattctgt 3660
ggataaccgt attaccgcct ttgagtgagc tgataccgct cgccgcagcc gaacgaccga 3720
gcgcagcgag tcagtgagcg aggaagcgga agagcgcctg atgcggtatt ttctccttac 3780
gcatctgtgc ggtatttcac accgcatata tggtgcactc tcagtacaat ctgctctgat 3840
gccgcatagt taagccagta tacactccgc tatcgctacg tgactgggtc atggctgcgc 3900
cccgacaccc gccaacaccc gctgacgcgc cctgacgggc ttgtctgctc ccggcatccg 3960
cttacagaca agctgtgacc gtctccggga gctgcatgtg tcagaggttt tcaccgtcat 4020
caccgaaacg cgcgaggcag ctgcggtaaa gctcatcagc gtggtcgtga agcgattcac 4080
agatgtctgc ctgttcatcc gcgtccagct cgttgagttt ctccagaagc gttaatgtct 4140
ggcttctgat aaagcgggcc atgttaaggg cggttttttc ctgtttggtc actgatgcct 4200
ccgtgtaagg gggatttctg ttcatggggg taatgatacc gatgaaacga gagaggatgc 4260
tcacgatacg ggttactgat gatgaacatg cccggttact ggaacgtttgt gagggtaaac 4320
aactggcggt atggatgcgg cgggaccaga gaaaaatcac tcagggtcaa tgccagcgct 4380
tcgttaatac agatgtaggt gttccacagg gtagccagca gcatcctgcg atgcagatcc 4440
ggaacataat ggtgcagggc gctgacttcc gcgtttccag actttacgaa acacggaaac 4500
cgaagaccat tcatgttgtt gctcaggtcg cagacgtttt gcagcagcag tcgcttcacg 4560
ttcgctcgcg tatcggtgat tcattctgct aaccagtaag gcaacccgt cagtcagccc 4620
gggtcctcaa cgacaggagc acgatcatgc gcacccgtgg ggccgccatg ccggcgataa 4680
tggcctgctt ctcgccgaaa cgtttggtgg cgggaccagt gacgaaggct tgagcgaggg 4740
cgtgcaagat tccgaatacc gcaagcgaca ggccgatcat cgtcgcgctc cagcgaaagc 4800
ggtcctcgcc gaaaatgacc cagagcgctg ccggcacctg tcctacgagt tgcatgataa 4860
agaagacagt cataagtgcg gcgacgatag tcatgccccg cgcccaccgg aaggagctga 4920
```

```
ctgggttgaa ggctctcaag ggcatcggtc gagatcccgg tgcctaatga gtgagctaac  4980
ttacattaat tgcgttgcgc tcactgcccg ctttccagtc gggaaacctg tcgtgccagc  5040
tgcattaatg aatcggccaa cgcgcgggga gaggcggttt gcgtattggg cgccagggtg  5100
gttttttcttt tcaccagtga gacgggcaac agctgattgc ccttcaccgc ctggccctga  5160
gagagttgca gcaagcggtc cacgctggtt tgccccacgg ggcgaaaatc ctgtttgatg  5220
gtggttaacg gcgggatata acatgagctg tcttcggtat cgtcgtatcc cactaccgag  5280
atatccgcac caacgcgcag cccggactcg gtaatggcgc gcattgcgcc cagcgccatc  5340
tgatcgttgg caaccagcat cgcagtggga acgatgccct cattcagcat ttgcatggtt  5400
tgttgaaaac cggacatggc actccagtcg ccttcccgtt ccgctatcgg ctgaatttga  5460
ttgcgagtga gatatttatg ccagccagcc agacgcagac gcgccgagac agaacttaat  5520
gggcccgcta acagcgcgat ttgctggtga cccaatgcga ccagatgctc cacgcccagt  5580
cgcgtaccgt cttcatggga gaaaataata ctgttgatgg gtgtctggtc agagacatca  5640
agaaataacg ccggaacatt agtgcaggca gcttccacag caatggcatc ctggtcatcc  5700
agcggatagt taatgatcag cccactgacg cgttgcgcga agagttgcac cgccgct     5760
ttacaggctt cgacgccgct tcgttctacc atcgacacca ccacgctggc acccagttga  5820
tcggcgcgag atttaatcgc cgcgacaatt tgcgacggcg cgtgcagggc cagactggag  5880
gtggcaacgc caatcagcaa cgactgtttg ccgccagtt gttgtgccac gcggttggga  5940
atgtaattca gctcccgcat cgccgcttcc acttttccc gcgttttcgc agaaacgtgg  6000
ctggcctggt tcaccacgcg ggaaacggtc tgataagaga caccggcata ctctgcgaca  6060
tcgtataacg ttactggttt cacattcacc accctgaatt gactctcttc cgggcgctat  6120
catgccatac cgcgaaggt tttgcgccat tcgatggtgt ccgggatctc gacgctctcc  6180
cttatgcgac tcctgcatta ggaagcagcc cagtagtagg ttgaggccgt tgagcaccgc  6240
cgccgcaagg aatggtgcat gcaaggagat ggcgcccaac agtccccgg ccacggggcc  6300
tgccaccata cccacgccga aacaagcgct catgagcccg aagtggcgag cccgatcttc  6360
cccatcggtg atgtcggcga tataggcgcc agcaaccgca cctgtggcgc cggtgatgcc  6420
ggccacgatg cgtccggcgt agaggatcg                                     6449
```

SEQ ID NO: 4                 moltype = DNA   length = 4603
FEATURE                   Location/Qualifiers
misc_feature         1..4603
                         note = EXPRESSION VECTOR pEco-NHalo-CHis
source                    1..4603
                         mol_type = other DNA
                         organism = synthetic construct
SEQUENCE: 4

```
ggatctcgat cccgcgaaat taatacgact cactataggg agaccacaac ggtttcccga    60
attgtgagcg gataacaata gaaataattt tgtttaactt taagaaggag atatatcgat   120
ggcagaaatc ggtactggct ttccattcga cccccattat gtggaagtcc tgggcgagcg   180
catgcactac gtcgatgttg gtccgcgcga tggcacccct ggctgttcc tgcacggtaa   240
cccgacctcc tcctacgtgt ggcgcaacat catcccgcat gttgcaccga cccatcgctg   300
cattgctcca gacctgatcg gtatgggcaa atccgcacaaa ccagacctgg gttatttctt   360
cgacgaccac gtccgcttca tggatgcctt catcgaagcc ctgggtctgg aagaggtcgt   420
cctggtcatt cacgactggg gctccgctct gggtttcaac tgggccaagc gcaatccaga   480
gcgcgtcaaa ggtattgcat ttatggagtt catccgccct atcccgacct gggacgaatg   540
gccagaattt gcccgcgaga ccttccaggc cttccgcacc accgacgtcg gccgcaagct   600
gatcatcgat cagaacgttt ttatcgaggg tacgctgccg atgggtgtcg tccgcccgct   660
gactgagtcg gagatggacc attaccgcga gccgttcctg aatcctgttg accgcgagcc   720
actgtggcgc ttcccaaacg agctgccaat cgccggtgag ccagcgaaca tcgtcgcgct   780
ggtcgaagaa tacatggact ggctgcacca gtccctgtc cgaagctgc tgttctgggg   840
caccccaggc gttctgatcc caccggccga agccgctcgc ctggccaaaa gctgcctaa    900
ctggacaagct gtggacatcg gccgggtct gaatctgcaa gaagaca acccggacct    960
gatcggcagc gagatcgcgc gctggctgtc gacgctcgag atttccggcg agccaaccac  1020
tgaggatctg tactttcaga gcgataacgc gatcgccatg gaacatatgg ctagcgaatt  1080
cgagctcaag cttcagaagc aagctgaaga ggcggcagcg aaagcggcgg cagatgctaa  1140
agcaggcc gaagcagatg ctaaagctgc ggaagaagca ggcgaagaag cggctgcaga  1200
cgcaaagaaa aagcgaagc cagaagcgc caaagcgcga gccgaagcgc agaaaaagc  1260
cgaggcagcc gctgcggcac tgaagaagaa agcggaagcg gcagaagcag ctgcagctga  1320
agcaagaaaa aaagcggcaa ctgaagctgc tgaaaaagcc aaagcagaag ctgagaagaa  1380
agcggctgct gaaaggctg cagctgataa gaaagcggca gcagagaaag ctgcagccga  1440
caaaaaagca gcagaaaaag cggcagaaag gctgataaga agcagcggc  1500
agaaaaagcc gccgcagaca aaaagcggc agcggcaaaa gctgcagctg aaaaagccgc  1560
tgcagcaaaa gcgccgcag aggcagatga tattttcggt gagctacacc accaccacca  1620
ccactgagga tcctctagag tcgacctgca ggcatgcaag ctgatccggc tgctaacaaa  1680
gcccgaaagg aagctgagtt ggctgctgcc accgctgagc aataactagc ataaccctt  1740
ggggcctcta aacgggtctt gaggggttt ttgctgaaag gaggaactat atccggttcg  1800
cttgctgtcc ataaaaccgc ccagtctagc tatcgccatg taagcccact gcaagctacc  1860
tgctttctct ttgcgcttgc gttttccctt gtccagatag cccagtagct gacattcatc  1920
cggggtcagc accgtttctg cggactggct ttctacgtgt tccgcttcct ttagcagccc  1980
ttgcgccctg agtgcttgcg gcagcgtgag cttcaaaaga attgccagct ggggcgccct  2040
ctggtaaggt tgggaagccc tgcaaagtaa actggatggc tttcttgccg ccaaggatct  2100
gatggcgcag gggatcaaga tctgatcaag acaggatg acggtcgttt cgcatgcttg  2160
aacaagatga ttgcacgca ggttctccgg ccgcttgggt ggagaggcta ttcggctatg  2220
actgggcaca acagacaatc ggctgctctg atgccgccgt gttccggctg tcagcgcagg  2280
ggcgcccggt tctttttgtc aagaccgacc tgtccggtgc cctgaatgaa ctgcaggacg  2340
aggcagcgcg gctatcgtgg ctggccacga cgggcgttcc ttgcgcagct gtgctcgacg  2400
ttgtcactga agcggaagg gactggctgc tattgggcga agtgccgggg caggatctcc  2460
tgtcatctca ccttgctcct gccgagaaag tatccatcat ggctgatgca atgcggcggc  2520
tgcatacgct tgatccggct acctgcccat tcgaccacca agcgaaacat cgcatcgagc  2580
gagcacgcac tcggatggaa gccggtcttg tcgatcagga tgatctggac gaagagcatc  2640
```

```
agggctcgc gccagccgaa ctgttcgcca ggctcaaggc gcgtatgccg gatggtgagg    2700
atctcgtcgt gactcatggc gatgcctgct tgccgaatat catggtggaa aatggccgct    2760
tttctggatt catcgactgt ggccggctgg gtgtggcgga ccgctatcag gacatagcgt    2820
tggctacccg tgatattgct gaagagcttg gcggcgaatg ggctgaccgc ttcctcgtgc    2880
tttacggtat cgccgctccc gattcgcagc gcatcgcctt ctatcgcctt cttgacgagt    2940
tcttctgagc gggactctgg ggttcgaaat gaccgaccaa gcgacgccca accggtatca    3000
gctcactcaa aggcggtaat acggttatcc acagaatcag gggataacgc aggaaagaac    3060
atgtgagcaa aaggccagca aaaggccagg aaccgtaaaa aggccgcgtt gctggcgttt    3120
ttccataggc tccgcccccc tgacgagcat cacaaaaatc gacgctcaag tcagaggtgg    3180
cgaaacccga caggactata aagataccag gcgtttcccc ctggaagctc cctcgtgcgc    3240
tctcctgttc cgaccctgcc gcttaccgga tacctgtccg cctttctccc ttcgggaagc    3300
gtggcgcttt ctcatagctc acgctgtagg tatctcagtt cggtgtaggt cgttcgctcc    3360
aagctgggct gtgtgcacga accccccgtt cagcccgacc gctgcgcctt atccggtaac    3420
tatcgtcttg agtccaaccc ggtaagacac gacttatcgc cactggcagc agccactggt    3480
aacaggatta gcagagcgag gtatgtaggc ggtgctacag agttcttgaa gtggtggcct    3540
aactacggct acactagaag gacagtattt ggtatctgcg ctctgctgaa gccagttacc    3600
ttcggaaaaa gagttggtag ctcttgatcc ggcaaacaaa ccaccgctgg tagcggtggt    3660
ttttttgttt gcaagcagca gattacgcgc agaaaaaaag gatttcaaga agatccttg    3720
atcttttcta cggggtctga cgctcagtgg aacgaaaact cacgttaagg gattttggtc    3780
atgagattat caaaaaggat cttcacctag atccttttat agtccggaaa tacaggaacg    3840
cacgctggat ggcccttcgc tgggatggtg aaaccatgaa aaatggcagc ttcagtggat    3900
taagtggggg taatgtcatc tgttacccct ggttgcatag gtattcatac ggttaaaatt    3960
tatcaggcgc gattgcggca gttttccggg tggtttgttg ccatttttac ctgtctgctg    4020
ccgtgatcgc gctgaacgcg ttttagcggt gcgtacaatt aagggattat ggtaaatcca    4080
cttactgtct gccctcgtag ccatcgagat aaaccgcagt actccggcca cgatgcgtcc    4140
ggcgtagagg atcgagatct tttcagcctg atacagatta aatcagaacg aagaagcgtt    4200
ctgataaaac agaatttgcc tggcggcagt agcgcggtgg tcccacctga ccccatgccg    4260
aactcagaag tgaaacgccg tagcgccgat ggtagtgtgg ggtctcccca tgcgagagta    4320
gggaactgcc aggcatcaaa taaaacgaaa ggctcagtcg aaagactggg cctttcgttt    4380
tatctgttgt ttgtcggtga acgctctcct gagtaggaca atccgccgg gagcggattt    4440
gaacgttgcg aagcaacggc ccggagggtg gcgggcagga cgcccgccat aaactgccag    4500
gcatcaaatt aagcagaagg ccatcctgac ggatggcctt tttgcgtttc tacaaactct    4560
tttgtttatt tttctaaata cattcaaata tgtatccgct cat                      4603
```

SEQ ID NO: 5        moltype = DNA   length = 5792
FEATURE                Location/Qualifiers
misc_feature       1..5792
                       note = EXPRESSION VECTOR pBac-NFlagHA
source                 1..5792
                       mol_type = other DNA
                       organism = synthetic construct
SEQUENCE: 5

```
gacgcgccct gtagcggcgc attaagcgcg gcgggtgtgg tggttacgcg cagcgtgacc      60
gctacacttg ccagcgccct agcgcccgct cctttcgctt tcttcccttc ctttctcgcc     120
acgttcgccg gctttccccg tcaagctcta aatcgggggc tccctttagg gttccgattt     180
agtgctttac ggcacctcga ccccaaaaaa cttgattagg gtgatggttc acgtagtggg     240
ccatcgccct gatagacggt ttttcgccct ttgacgttgg agtccacgtt ctttaatagt     300
ggactcttgt tccaaactgg aacaacactc aaccctatct cggtctattc ttttgattta     360
taagggattt tgccgatttc ggcctattgg ttaaaaaatg agctgattta acaaaaattt     420
aacgcgaatt ttaacaaaat attaacgttt acaatttcag gtggcacttt tcggggaaat     480
gtgcgcggaa cccctatttg tttatttttc taaatacatt caaatatgta tccgctcatg     540
agacaataac cctgataaat gcttcaataa tattgaaaaa ggaagagtat gagtattcaa     600
catttccgtg tcgcccttat tccctttttt gcggcatttt gccttcctgt ttttgctcac     660
ccagaaacgc tggtgaaagt aaaagatgct gaagatcagt tgggtgcacg agtgggttac     720
atcgaactgg atctcaacag cggtaagatc cttgagagtt ttcgccccga agaacgtttt     780
ccaatgatga gcactttaaa gttctgctat gtggcgcgg tattatcccg tattgacgcg     840
ggcaagagc aactcggtcg ccgcatacac tattctcaga atgacttggt tgagtactca     900
ccagtcacag aaaagcatct tacggatggc atgacagtaa gagaattatg cagtgctgcc     960
ataaccatga gtgataacac tgcggccaac ttacttctga caacgatcgg aggaccgaag    1020
gagctaaccg cttttttgca caacatgggg gatcatgtaa ctcgccttga tcgttgggaa    1080
ccggagctga atgaagccat accaaacgac gagcgtgaca ccacgatgcc tgtagcaatg    1140
gcaacaacgt tgcgcaaact attaactggc gaactactta ctctagcttc ccggcaacaa    1200
ttaatagact ggatggaggc ggataaagtt gcaggaccac ttctgcgctc ggcccttccg    1260
gctggctggt ttattgctga taaatctgga gccggtgagc gtgggtctcg cggtatcatt    1320
gcagcactgg ggccagatgg taagccctcc cgtatcgtag ttatctacac gacggggagt    1380
caggcaacta tggatgaacg aaatagacag atcgctgaga taggtgcctc actgattaag    1440
cattggtaac tgtcagacca agtttactca tatatacttt agattgattt aaaacttcat    1500
ttttaattta aaaggatcta ggtgaagatc ctttttgata atctcatgac caaaatccct    1560
taacgtgagt tttcgttcca ctgagcgtca gaccccgtag aaaagatcaa aggatcttct    1620
tgagatcctt ttttctgcgc gtaatctgct gcttgcaaa caaaaaaacc accgctacca    1680
gcggtggttt gtttgccgga tcaagagcta ccaactcttt ttccgaaggt aactggcttc    1740
agcagagcgc agataccaaa tactgtcctt ctagtgtagc cgtagttagg ccaccacttc    1800
aagaactctg tagcaccgcc tacatacctc gctctgctaa tcctgttacc agtggctgct    1860
gccagtggcg ataagtcgtg tcttaccggg ttggactcaa gacgatagtt accggataag    1920
gcgcagcggt cgggctgaac ggggggttcg tgcacacagc ccagcttgga gcgaacgacc    1980
tacaccgaac tgagatacct acagcgtgag cattgagaaa gcgccacgct tcccgaaggg    2040
agaaaggcgg acaggtatcc ggtaagcggc agggtcggaa caggagagcg cacgagggag    2100
cttccagggg gaaacgcctg gtatctttat agtcctgtcg ggtttcgcca cctctgactt    2160
gagcgtcgat ttttgtgatg ctcgtcaggg gggcggagcc tatggaaaaa cgccagcaac    2220
```

```
gcggccttttt tacggttcct ggccttttgc tggccttttg ctcacatgtt ctttcctgcg   2280
ttatccctg attctgtgga taaccgtatt accgcctttg agtgagctga taccgctcgc    2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggacg aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacgca aggtgctgtg    3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
gttcgcccag gactctagct atagttctag tggttggcta cgtatactcc ggaatattaa   3900
tagatcatga agataattaa aatgataacc atctcgcaaa taaataagta ttttactgtt   3960
ttcgtaacag ttttgtaata aaaaaaccta taaatattcc ggattattca taccgtccca   4020
ccatcgggcg cggatcctcg atgaagacca tcatcgctct gtcctacatc ttctgcctgt   4080
tgttcgctga ctacaaggac gacgacgacg cttcctccta cccctacgac gtgcccgact   4140
acgctatggc tgagatcggc accggtttcc ccttcgaccc ccactacgtg gaggtgctgg   4200
gtgagcgtat gcactacgtg gacgtgggtc ccgtgacgg caccccccgtg ctgttcctgc   4260
acggtaaccc cacctcctcc tacgtgtggc gtaacatcat ccccacgtg gctcccaccc   4320
accgttgcat cgctcccgac ctgatccgta tgggtaagtc cgacaagccc gacctgggtt   4380
acttcttcga cgaccacgtg cgtttcatgg acgctttcat cgaggctctg ggtctggagg   4440
aggtggtgct ggtgatccac gactgggggtt ccgctctggg ttttccactgg gctaagcgta   4500
accccgacgc tgtgaagggt atcgcttttca tggagttcat ccgtcccatc cccaccggg   4560
acgagtggcc cgagttcgct cgtgagacct tccaggcttt ccgtaccacc gacgtgggtc   4620
gtaagctgat catcgaccag aacgtgttca tcgagggcac cctgccttatg ggtgtggtgc   4680
gtccctgac cgaggtggag atggaccact accgtgagcc cttcctgaac cccgtggacc   4740
gtgagccct gtggcgtttc cccaacgagc tgcccatcgc tggtgagccc gctaacatcg   4800
tggctctggt ggaggagtac atggactggc tgcaccagtc ccccgtgccc aagctgctgt   4860
tctggggcac ccccggtgtg ctgatccccc ccgctgaggc tgctcgtctg gctaagtccc   4920
tgcccaactg caaggctgtg gacatcggtc ccggtctgaa cctgctccag gaggacaacc   4980
ccgacctgat cggttccgag atcgctcgtt ggctgtccac cctggagatc tccggtggtg   5040
gttccgtgc catggaacat atggctagcg aattcaaagg cctacgtcga cgagctcact   5100
agtcgcggcc gctttcgaat ctagagcctg cagtctcgag gcatgcggta ccaagcttgt   5160
cgagaagtac tagaggatca taatcagcca taccacattt gtagaggttt tacttgcttt   5220
aaaaaacctc ccacacctcc ccctgaacct gaaacataaa atgaatgcaa ttgttgttgt   5280
taacttgttt attgcagctt ataatggtta caaataaagc aatagcatca caaatttcac   5340
aaataaagca ttttttttcac tgcattctag ttgtggtttg tccaaactca tcaatgtatc   5400
ttatcatgtc tggatctgat cactgcttga gcctaggaga tccgaaccag ataagtgaaa   5460
tctagttcca aactattttg tcattttaa ttttcgtatt agcttacgac gctacaccca   5520
gttcccatct atttttgtcac tcttccctaa ataatcctta aaaactccat ttccacccct   5580
cccagttccc aactattttg tccgcccaca gcggggcatt ttcttcctg ttatgttttt   5640
aatcaaacat cctgccaact ccatgtgaca aaccgtcatc ttcggctact ttttctctgt   5700
cacagaatga aaatttttct gtcatctctt cgttattaat gtttgtaatt gactgaatat   5760
caacgcttat ttgcagcctg aatggcgaat gg                                 5792
SEQ ID NO: 6           moltype = DNA   length = 4830
FEATURE                Location/Qualifiers
misc_feature           1..4830
                       note = EXPRESSION VECTOR pIRES-CHaloFlagHis
source                 1..4830
                       mol_type = other DNA
                       organism = synthetic construct
SEQUENCE: 6
taatacgact cactataggg cgaattaatt ccggttattt tccaccatat tgccgtcttt    60
tggcaatgtg agggcccgga aacctggccc tgtcttcttg acgagcattc ctaggggtct   120
ttcccctctc gccaaaggaa tgcaaggtct gttgaatgtc gtgaaggaag cagttcctct   180
ggaagcttct tgaagacaaa caacgtctgt agcgacccct tgcaggcagc ggaacccccc   240
acctggcgac aggtgcctct gcggccaaaa gccacgtgta taagatacac ctgcaaaggc   300
ggcacaaccc cagtgccacg ttgtgagttg gatagttgtg gaaagagtca aatggctcac   360
ctcaagcgta ttcaacaagg ggctgaagga tgcccagaag gtaccccatt gtatgggatc   420
tgatctgggg cctcggtgca catgctttac atgtgtttag tcgaggttaa aaaacgtcta   480
ggccccccga accacgggga cgtggttttc ctttgaaaaa cacgatgata atatggccac   540
cacccatatg ggatccgaat tcgatatctt aattaagctg caggagctcg tcgacgcggc   600
```

```
cgcactcgag cagaagcaag ctgaagaggc ggcagcgaaa gcggcggcag atgctaaagc    660
gaaggccgaa gcagatgcta aagctgcgga agaagcagcg aagaaagcgg ctgccgacgc    720
aaagaaaaaa gcagaagcag aagccgccaa agccgcagcc gaagcgcaga aaaaagccga    780
ggcagccgct gcggcactga agaagaaagc ggaagcggca gaagcagctg ccgctgaagc    840
aagaaagaaa gcggcaactg aaggccgcag cggcatggcg gagatcggca ccggtttcat    900
cttcgaccec cactacgtgg aggtgctggg tgagcgtatg cactacgtgg acgtgggtcc    960
ccgtgacggc accccgtgc tgttcctgca cggtaacccc acctcctcct acgtgtggcg   1020
taacatcatc ccccacgtgg ctcccaccca ccgttgcatc gctcccgacc tgatcggtat   1080
gggtaagtcc gacaagcccg acctgggtta cttcttcgac gaccacgtgc gtttcatgga   1140
cgctttcatc gaggctctgg gtctggagga ggtggtgctg gtgatccacg actggggttc   1200
cgctctgggt ttccactggg ctaagcgtaa ccccgagcgt gtgaagggta tcgctttcat   1260
ggagttcatc cgtcccatcc ccacctggga cgagtggccc gagttcgctc gtgagacctt   1320
ccaggctttc cgtaccaccg acgtgggtcg taagctgatc atcgaccaga acgtgttcat   1380
cgagggcacc ctgcctatgg gtgtggtgcg tcccctgacc gaggtggaga tggaccacta   1440
ccgtgagccc ttcctgaacc ccgtggaccg tgagccctg tggcgtttcc ccaacgagtc   1500
gcccatcgct ggtgagcccg ctaacatcgt ggctctggtg gaggagtaca tggactggct   1560
gcaccagtcc cccgtgccca gctgctgtt ctggggcacc cccggtgtgc tgatccccc   1620
cgctgaggct gctcgtctgg ctaagtccct gcccaactgc aaggctgtgg acatcggtcc   1680
cggtctgaac ctgctccagg aggacaaccc cgacctgatc ggttccgaga tcgctcgttg   1740
gctgtccacc ctggagattt ccggtggtgg ttccggtgat tataaagatg atgatgataa   1800
aggcggcgcg ggcaccacc accaccacca ctgagatctg actgaaaaaa aaaaaaaaaa   1860
aaaaaaaaaa aaagtttaa aactactagtcc gctgagcaat aactagcata acccttggg   1920
gcctctaaac gggtcttgag gggtttttg ctgaaaggag gaactatatc cgggcttcct   1980
cgctcactga ctcgctgcgc tcggtcgttc ggctgcggcg agcggtatca gctcactcaa   2040
aggcggtaat acgttatcc acagaatcag gggataacgc aggaaagaac atgtgagcaa   2100
aaggccagca aaaggccagg aaccgtaaaa aggccgcgtt gctggcgttt ttccataggc   2160
tccgccccc tgacgagcat cacaaaaatc gacgctcaag tcagaggtgg cgaaacccga   2220
caggactata agataccag gcgtttcccc ctggaagctc cctcgtgcgc tctcctgttc   2280
cgaccctgcc gcttaccgga tacctgtccg ccttctccc ttcgggaagc gtggcgcttt   2340
ctcatagctc acgctgtagg tatctcagtt cggtgtaggt cgttcgctcc aagctgggct   2400
gtgtgcacga accccccgtt cagcccgacc gctgcgcctt atccggtaac tatcgtcttg   2460
agtccaaccc ggtaagacac gacttatcgc cactggcagc agccactggt aacaggatta   2520
gcagagcgag gtatgtaggc ggtgctacag agttcttgaa gtggtggcct aactacggct   2580
acactagaag gacagtattt ggtatctgcg ctctgctgaa gccagttacc ttcggaaaaa   2640
gagttggtag ctcttgatcc ggcaaacaaa ccaccgctgg tagcggtggt ttttttgttt   2700
gcaagcagca gattacgcgc agaaaaaag gatctcaaga agatcctttg atcttttcta   2760
cggggtctga cgctcagtgg aacgaaaact cacgttaagg gatttggtc atgagattat   2820
caaaaaggat cttcacctag atccttttaa attaaaaatg aagttttaaa tcaatctaaa   2880
gtatatatga gtaaacttgg tctgacagtt accaatgctt aatcagtgag gcacctatct   2940
cagcgatctg tctatttcgt tcatccatag ttgcctgact ccccgtcgtg tagataacta   3000
cgatacggga gggcttacca tctggcccca gtgctgcaat gataccgcga gacccacgct   3060
caccggctcc agatttatca gcaataaacc agccagccgg aagggccgag cgcagaagtg   3120
gtcctgcaac tttatccgcc tccatccagt ctattaattg ttgccgggaa gctagagtaa   3180
gtagttcgcc agttaatagt ttgcgcaacg ttgttgccat tgctacaggc atcgtggtgt   3240
cacgctcgtc gtttggtatg gcttcattca gctccggttc ccaacgatca aggcgagtta   3300
catgatcccc catgttgtgc aaaaaagcgg ttagctcctt cggtcctccg atcgttgtca   3360
gaagtaagtt ggccgcagtg ttatcactca tggttatggc agcactgcat aattctctta   3420
ctgtcatgcc atccgtaaga tgcttttctg tgactggtga gtactcaacc aagtcattct   3480
gagaatagtg tatgcggcga ccgagttgct cttgcccggc gtcaatacgg gataataccg   3540
cgccacatag cagaacttta aaagtgctca tcattggaaa acgttcttcg ggcgaaaac   3600
tctcaaggat cttaccgctg ttgagatcca gttcgatgta acccactcgt gcacccaact   3660
gatcttcagc atcttttact ttcaccagcg tttctgggtg agcaaaaaca ggaaggcaaa   3720
atgccgcaaa aaagggaata agggcgacac ggaaatgttg aatactcata ctcttccttt   3780
ttcaatatta ttgaagcatt tatcagggtt attgtctcat gagcggatac atatttgaat   3840
gtatttagaa aaataaacaa ataggggttc cgcgcacatt tccccgaaaa gtgccacctg   3900
acgtctaaga aaccattatt atcatgacat taacctataa aaataggcgt atcacgaggc   3960
cctttcgtct cgcgcgtttc ggtgatgacg gtgaaaacct ctgacacatg cagctcccgg   4020
agacggtcac agcttgtctg taagcggatg ccgggagcag acaagcccgt cagggcgcgt   4080
cagcgggtgt tggcgggtgt cggggctggc ttaactatgc ggcatcagag cagattgtac   4140
tgagagtgca ccatatatgc ggtgtgaaat accgcacaga tgcgtaagga gaaaataccg   4200
catcaggaaa ttgtaaacgt taatattttg ttaaaattcg cgttaaattt ttgttaaatc   4260
agctcatttt ttaaccaata ggccgaaatc ggcaaaatcc cttataaatc aaaagaatag   4320
accgagatag ggttgagtgt tgttccagtt tggaacaaga gtccactatt aaagaacgtg   4380
gactccaacg tcaaagggcg aaaaaccgtc tatcagggcg atggcccact acgtgaacca   4440
tcaccctaat caagttttt ggggtcgagg tgccgtaaag cactaaatcg gaaccctaaa   4500
gggagccccc gatttagagc ttgacgggga aagccggcga acgtggcgag aaaggaaggg   4560
aagaaagcga aggagcgggc gctagggcg ctggcaagtg tagcggtcac gctgcgcgta   4620
accaccacac ccgccgcgct taatgcgccg ctacagggcg cgtcgcgcca ttcgccattc   4680
aggctgcgca actgttggga agggcgatcg gtgcgggcct cttcgctatt acgccagctg   4740
gcgaaagggg gatgtgctgc aaggcgatta agttgggtaa cgccagggtt ttcccagtca   4800
cgacgttgta aaacgacggc cagtgaattg                                   4830

SEQ ID NO: 7          moltype = DNA   length = 6485
FEATURE               Location/Qualifiers
misc_feature          1..6485
                      note = EXPRESSION VECTOR pIRES-CHaloFlagHis-Gateway
source                1..6485
                      mol_type = other DNA
                      organism = synthetic construct
```

```
SEQUENCE: 7
taatacgact cactataggg cgaattaatt ccggttattt tccaccatat tgccgtcttt    60
tggcaatgtg agggcccgga aacctggccc tgtcttcttg acgagcattc ctagggtct   120
ttcccctctc gccaaaggaa tgcaaggtct gttgaatgtc gtgaaggaag cagttcctct   180
ggaagcttct tgaagacaaa caacgtctgt agcgacccct tgcaggcagc ggaaccccc    240
acctggcgac aggtgcctct gcggccaaaa gccacgtgta taagatacac ctgcaaaggc   300
ggcacaaccc cagtgccacg ttgtgagttg atagttgtg gaaagagtca aatggctcac    360
ctcaagcgta ttcaacaagg ggctgaagga tgcccagaag gtaccccatt gtatgggatc   420
tgatctgggg cctcggtgca catgctttac atgtgtttag tcgaggttaa aaaacgtcta   480
ggcccccga accacgggga cgtggttttc ctttgaaaaa cacgatgata atatggccac    540
cacccatatg ggaacaagtt tgtacaaaaa agctgaacga gaaacgtaaa atgatataaa   600
tatcaatata ttaaattaga ttttgcataa aaaacagact acataatact gtaaaacaca   660
acatatccag tcactatggc ggccgcatta ggcacccccag gctttacact ttatgcttcc   720
ggctcgtata atgtgtggat tttgagttag gatccgtcga gatttttcagg agctaaggaa   780
gctaaaatgg agaaaaaaat cactggatat accaccgttg atatatccca atggcatcgt   840
aaagaacatt ttgaggcatt tcagtcagtt gctcaatgta cctataacca gaccgttcag   900
ctggatatta cggccttttt aaagaccgta aagaaaaata agcacaagtt ttatccggcc   960
tttattcaca ttcttgcccg cctgatgaat gctcatccga aattccgtat ggcaatgaaa  1020
gacggtgagc tggtgatatg ggatagtgtt caccccttgtt acaccgtttt ccatgagcaa  1080
actgaaacgt tttcatcgct ctggagtgaa taccacgacg atttccggca gtttctacac  1140
atatattcgc aagatgtggc gtgttacggt gaaaacctgg cctatttccc taagggtttt  1200
attgagaata tgtttttcgt ctcagccaat ccctgggtga gtttcaccag ttttgattta  1260
aacgtggcca atatgacaa cttcttcgcc cccgttttca ccatgggcaa atattatacg  1320
caaggcgaca aggtgctgat gccgctggcg attcaggttc atcatgccgt ttgtgatggc  1380
ttccatgtcg gcagaatgct taatgaatta caacagtact gcgatgagtg gcagggcggg  1440
gcgtaaacgc gtggatccgg cttactaaaa gccagataac agtatgcgta tttgcgcgct  1500
gattttgtcg gtataagaat atatactgat atgtatacc gaagtatgtc aaaaagaggt  1560
atgctatgaa gcagcgtatt acagtgacag ttgacagcga cagctatcag ttgctcaagg  1620
catatatgat gtcaatatct ccggtctggt aagcacaacc atgcagaatg aagcccgtcg  1680
tctgcgtgcc gaacgctgga aagcggaaaa tcaggaaggg atggctgagg tcgcccggtt  1740
tattgaaatg aacggctctt ttgctgacga aacaggggc tggtgaaatg cagtttaagg  1800
tttacaccta taaagagag agccgttatc gtctgtttgt ggatgtacag agtgatatta  1860
ttgacacgcc cgggcgacgg atggtgatcc ccctggccag tgcacgtctg ctgtcagata  1920
aagtctcccg tgaactttac ccggtggtgc atatcgggga tgaaagctgg cgcatgatga  1980
ccaccgatat ggccagtgtg ccggtctccg ttatcgggga agaagtggct gatctcagcc  2040
accgcgaaaa tgacatcaaa aacgccatta acctgatgtt ctggggaata taatgtcag   2100
gctccctta acacagccag tctgcaggtc gaccatagtg actggatatg ttgtgtttta  2160
cagtattatg tagtctgttt tttatgcaaa atctaattta atatattgat atttatatca  2220
ttttacgttt ctcgttcagc tttcttgtac aaagtggtgc tcgagcagaa gcaagtgaa   2280
gaggcggcag cgaaagcggc ggcagatgct aaagcgaagg ccgaagcaga tgctaaagct  2340
gcggaagaag cagcgaagaa agcggctgcc gacgcaaaga aaaagcaga agcagaagcc  2400
gccaaagccg cagccgaagc gcagaaaaaa gccgaggcag ccgctgcggc actgaagaag  2460
aagcggaaga cggcagaagc agctgccgct gaagcaagaa aagcggc aactgaaggc  2520
ggcagcggca tggctgagat cggcaccggt tccccttcg accccacta cgtggaggtg  2580
ctgggtgagc gtatgcacta cgtggacgtg gtcccgtg acggcacccc cgtgctgttc  2640
ctgcacggta accccacctc ctcctacgtg tggcgtaaca tcatccccca cgtggctccc  2700
acccacgtt gcatcgctcc cgacctgatc ggtatggta agtccgacaa gcccgacctg  2760
ggttacttct tcgacgacca cgtgcgtttc atggacgctt tcatcgaggc tctgggtctg  2820
gaggaggtgg tgctggtgat ccacgactgg ggttccgctc tgggtttcca ctgggctaag  2880
cgtaaccccg agcgtgtgaa gggtatcgct ttcatggagt tcatccgtcc catccccacc  2940
tgggacgagt ggcccagtt cgctcgtgag accttccgag ctttccgtac caccgacgtg  3000
ggtcgtaagc tgatcatcga ccagaacgtg ttcatcgagg gcaccctgcc tatgggtgtg  3060
gtgcgtcccc tgaccgaggt ggagatggac cactaccgtg agcccttcct gaaccccgtg  3120
gaccgtgagc ccctgtggcg tttccccaac gagctgccca tcgctggtga gcccgctaac  3180
atcgtggctc tggtggagga gtacatggac tggctgcacc agtcccccgt gcccaagctg  3240
ctgttctggg gcaccccgg tgtgctgatc ccccgctg aggctgctcg tctggctaag  3300
tccctgccca actgcaaggc tgtggacatc ggtcccggtc tgaacctgct ccaggaggac  3360
aacccgacc tgatcggttc cgagatcgct cgttggctgt ccaccctgga gatttccggt  3420
ggtggttccg gtgattataa agatgatgat gataaaggcg gcgcggccca ccaccaccac  3480
caccactgag atctgactga aaaaaaaaa aaaaaaaaaa aaaaaaaag tttaaacact  3540
agtccgctga gcaataacta gcataacccc ttggggcctc taaacgggtc ttgaggggtt  3600
ttttgctgaa aggaggaact atatccgggc ttcctcgctc actgactcgc tgcgctcggt  3660
cgttcggctg cggcgagcgg tatcagctca ctcaaaggcg gtaatacggt tatccacaga  3720
atcaggggat aacgcaggaa agaacatgtg agcaaaaggc cagcaaaagg ccaggaaccg  3780
taaaaaggcc gcgttgctgg cgtttttcca taggctccgc cccctgacg agcatcacaa  3840
aaatcgacgc tcaagtcaga ggtggcgaaa cccgacagga ctataaagat accaggcgtt  3900
tccccctgga agctccctcg tgcgctctcc tgttccgacc ctgccgctta ccggatacct  3960
gtccgccttt ctcccttcgg gaagcgtggc gctttctcat agctcacgct gtaggtatct  4020
cagttcggtg taggtcgttc gctccaagct gggctgtgtg cacgaacccc ccgttcagcc  4080
cgaccgctgc gccttatccg gtaactatcg tcttgagtcc aacccggtaa gacacgactt  4140
atcgccactg gcagcagcca ctggtaacag gattagcaga gcgaggtatg taggcggtgc  4200
tacagagttc ttgaagtggt ggcctaacta cggctacact agaaggacag tatttggtat  4260
ctgcgctctg ctgaagccag ttaccttcgg aaaaagagtt ggtagctctt gatccggcaa  4320
acaaaccacc gctggtacg gtggtttttt tgtttgcaag cagcagatta cgcgcagaaa  4380
aaaaggatct caagaagatc ctttgatctt ttctacgggg tctgacgctc agtggaacga  4440
aaactcacgt taagggattt tggtcatgag attatcaaaa aggatcttca cctagatcct  4500
tttaaattaa aaatgaagtt ttaaatcaat ctaaagtata tatgagtaaa cttggtctga  4560
cagttaccaa tgcttaatca gtgaggcacc tatctcagcg atcgtgtctat tcgttcatc  4620
catagttgcc tgactccccg tcgtgtagat aactacgata cgggagggct taccatctgg  4680
```

```
ccccagtgct gcaatgatac cgcgagaccc acgctcaccg gctccagatt tatcagcaat   4740
aaaccagcca gccggaaggg ccagcgcag  aagtggtcct gcaactttat ccgcctccat   4800
ccagtctatt aattgttgcc gggaagctag agtaagtagt tcgccagtta atagtttgcg   4860
caacgttgtt gccattgcta caggcatcgt ggtgtcacgc tcgtcgtttg gtatggcttc   4920
attcagctcc ggttcccaac gatcaaggcg agttacatga tcccccatgt tgtgcaaaaa   4980
agccggttagc tccttcggtc ctccgatcgt tgtcagaagt aagttggccg cagtgttatc   5040
actcatggtt atggcagcac tgcataattc tcttactgtc atgccatccg taagatgctt   5100
ttctgtgact ggtgagtact caaccaagtc attctgagaa tagtgtatgc ggcgaccgag   5160
ttgctcttgc ccggcgtcaa tacgggataa taccgcgcca catagcagaa ctttaaaagt   5220
gctcatcatt ggaaaacgtt cttcggggcg aaaactctca aggatcttac cgctgttgag   5280
atccagttcg atgtaaccca ctcgtgcacc caactgatct tcagcatctt ttactttcac   5340
cagcgtttct gggtgagcaa aaacaggaag gcaaaatgcc gcaaaaaagg gaataagggc   5400
gacacggaaa tgttgaatac tcatactctt ccttttcaa tattattgaa gcatttatca   5460
gggttattgt ctcatgagcg gatacatatt tgaatgtatt tagaaaaata aacaaatagg   5520
ggttccgcgc acatttcccc gaaaagtgcc acctgacgtc taagaaacca ttattatcat   5580
gacattaacc tataaaaata ggcgtatcac gaggcccttt cgtctcgcgc gtttcggtga   5640
tgacggtgaa aacctctgac acatgcagct cccggagacg gtcacagctt gtctgtaagc   5700
ggatgccggg agcagacaag cccgtcaggg cgcgtcaggg ggtgttggcg ggtgtcgggg   5760
ctggcttaac tatgcggcat cagagcagat tgtactgaga gtgcaccata tgcggtgt    5820
gaaataccgc acagatgcgt aaggagaaaa taccgcatca ggaaattgta aacgttaata   5880
ttttgttaaa attcgcgtta aattttgtt  aaatcagctc attttttaac caataggccg   5940
aaatcggcaa aatcccttat aaatcaaaag aatagaccga gatagggttg agtgttgttc   6000
cagtttggaa caagagtcca ctattaaaga acgtggactc caacgtcaaa gggcgaaaaa   6060
ccgtctatca gggcgatggc ccactacgtg aaccatcacc ctaatcaagt tttttggggt   6120
cgaggtgccg taaagcacta atcggaacc  ctaaagggag cccccgattt agagcttgac   6180
ggggaaagcc ggcgaacgtg gcgagaaagg aaggaaagga gcggaaagga gcgggcgcta   6240
gggcgctggc aagtgtagcg gtcacgctgc gcgtaaccac cacacccgcc gcgcttaatg   6300
cgccgctaca gggcgcgtcg cgccattcgc cattccaggct gcgcaactgt tgggaagggc   6360
gatcggtgcg ggcctcttcg ctattacgcc agctggcgaa aggggatgt  gctgcaaggc   6420
gattaagttg ggtaacgcca gggttttccc agtcacgacg ttgtaaaacg acggccagtg   6480
aattg                                                               6485

SEQ ID NO: 8             moltype = DNA  length = 66
FEATURE                  Location/Qualifiers
misc_feature             1..66
                         note = PRIMER Template barcoded (F)
misc_feature             50..54
                         note = n is a, c, or t
source                   1..66
                         mol_type = other DNA
                         organism = synthetic construct
SEQUENCE: 8
cgaaattaat acgactcact atagggaatg atacggcgac caccgagggn nnnnagaaa   60
tgagga                                                              66

SEQ ID NO: 9             moltype = DNA  length = 18
FEATURE                  Location/Qualifiers
misc_feature             1..18
                         note = PRIMER Template (R)
source                   1..18
                         mol_type = other DNA
                         organism = synthetic construct
SEQUENCE: 9
tgctagttgc tcccgcac                                                 18

SEQ ID NO: 10            moltype = DNA  length = 30
FEATURE                  Location/Qualifiers
misc_feature             1..30
                         note = RT primer
source                   1..30
                         mol_type = other DNA
                         organism = synthetic construct
SEQUENCE: 10
ttttttttc aagcagaaga cggcatacga                                     30

SEQ ID NO: 11            moltype = DNA  length = 172
FEATURE                  Location/Qualifiers
misc_feature             1..172
                         note = HALO TAG PRIMER
source                   1..172
                         mol_type = other DNA
                         organism = synthetic construct
SEQUENCE: 11
acttcagtac gtcactacca acaatgatgg aatccctagg ttggcttacc aaaaatgaag   60
ctgatgaata ctccctcaaa gacaattgtc aaccttactt gtccattcct gaagaaatat   120
tatatttata caacttaccc atagaatcct atcgtatgcc gtcttctgct tg           172

SEQ ID NO: 12            moltype = DNA  length = 50
FEATURE                  Location/Qualifiers
```

```
misc_feature              1..50
                          note = PRIMER Barcoding DNA (F)
misc_feature              25..28
                          note = n is a, c, or t
source                    1..50
                          mol_type = other DNA
                          organism = synthetic construct
SEQUENCE: 12
aatgatacgg cgaccaccga ggggnnnnac ttcagtacgt cactaccaac             50

SEQ ID NO: 13             moltype = DNA  length = 21
FEATURE                   Location/Qualifiers
misc_feature              1..21
                          note = PRIMER Barcoding DNA (R)
source                    1..21
                          mol_type = other DNA
                          organism = synthetic construct
SEQUENCE: 13
caagcagaag acggcatacg a                                            21

SEQ ID NO: 14             moltype = DNA  length = 29
FEATURE                   Location/Qualifiers
misc_feature              1..29
                          note = PRIMER Barcoding DNA modification (F)
source                    1..29
                          mol_type = other DNA
                          organism = synthetic construct
SEQUENCE: 14
tttttttta atgatacggc gaccaccga                                     29

SEQ ID NO: 15             moltype = DNA  length = 30
FEATURE                   Location/Qualifiers
misc_feature              1..30
                          note = Barcoding DNA modification (R)
source                    1..30
                          mol_type = other DNA
                          organism = synthetic construct
SEQUENCE: 15
tttttttttc aagcagaaga cggcatacga                                   30

SEQ ID NO: 16             moltype = DNA  length = 30
FEATURE                   Location/Qualifiers
misc_feature              1..30
                          note = PRIMER Bridge amplification (F)
source                    1..30
                          mol_type = other DNA
                          organism = synthetic construct
SEQUENCE: 16
tttttttttt aatgatacgg cgaccaccga                                   30

SEQ ID NO: 17             moltype = DNA  length = 30
FEATURE                   Location/Qualifiers
misc_feature              1..30
                          note = PRIMER Bridge amplification (R)
source                    1..30
                          mol_type = other DNA
                          organism = synthetic construct
SEQUENCE: 17
tttttttttt caagcagaag acggcaacga                                   30

SEQ ID NO: 18             moltype = DNA  length = 19
FEATURE                   Location/Qualifiers
misc_feature              1..19
                          note = PRIMER Sequencing 1_Cy3
source                    1..19
                          mol_type = other DNA
                          organism = synthetic construct
SEQUENCE: 18
cccgggttcc tcattctct                                               19

SEQ ID NO: 19             moltype = DNA  length = 19
FEATURE                   Location/Qualifiers
misc_feature              1..19
                          note = PRIMER Sequencing 2_Cy5
source                    1..19
                          mol_type = other DNA
                          organism = synthetic construct
SEQUENCE: 19
ggtagtgacg tactgaagt                                               19
```

| | | |
|---|---|---|
| SEQ ID NO: 20 | moltype = DNA length = 19 | |
| FEATURE | Location/Qualifiers | |
| misc_feature | 1..19 | |
| | note = PRIMER Sequencing 1 | |
| source | 1..19 | |
| | mol_type = other DNA | |
| | organism = synthetic construct | |
| SEQUENCE: 20 | | |
| cccgggttcc tcattctct | | 19 |
| | | |
| SEQ ID NO: 21 | moltype = DNA length = 19 | |
| FEATURE | Location/Qualifiers | |
| misc_feature | 1..19 | |
| | note = PRIMER Sequencing 2 | |
| source | 1..19 | |
| | mol_type = other DNA | |
| | organism = synthetic construct | |
| SEQUENCE: 21 | | |
| ggtagtgacg tactgaagt | | 19 |
| | | |
| SEQ ID NO: 22 | moltype = AA length = 15 | |
| FEATURE | Location/Qualifiers | |
| REGION | 1..15 | |
| | note = Avi tag | |
| source | 1..15 | |
| | mol_type = protein | |
| | organism = synthetic construct | |
| SEQUENCE: 22 | | |
| GLNDIFEAQK IEWHE | | 15 |
| | | |
| SEQ ID NO: 23 | moltype = AA length = 26 | |
| FEATURE | Location/Qualifiers | |
| REGION | 1..26 | |
| | note = calmodulin tag | |
| source | 1..26 | |
| | mol_type = protein | |
| | organism = synthetic construct | |
| SEQUENCE: 23 | | |
| KRRWKKNFIA VSAANRFKKI SSSGAL | | 26 |
| | | |
| SEQ ID NO: 24 | moltype = AA length = 8 | |
| FEATURE | Location/Qualifiers | |
| REGION | 1..8 | |
| | note = FLAG tag | |
| source | 1..8 | |
| | mol_type = protein | |
| | organism = synthetic construct | |
| SEQUENCE: 24 | | |
| DYKDDDDK | | 8 |
| | | |
| SEQ ID NO: 25 | moltype = AA length = 9 | |
| FEATURE | Location/Qualifiers | |
| REGION | 1..9 | |
| | note = HA tag | |
| source | 1..9 | |
| | mol_type = protein | |
| | organism = synthetic construct | |
| SEQUENCE: 25 | | |
| YPYDVPDYA | | 9 |
| | | |
| SEQ ID NO: 26 | moltype = AA length = 6 | |
| FEATURE | Location/Qualifiers | |
| REGION | 1..6 | |
| | note = His tag | |
| source | 1..6 | |
| | mol_type = protein | |
| | organism = synthetic construct | |
| SEQUENCE: 26 | | |
| HHHHHH | | 6 |
| | | |
| SEQ ID NO: 27 | moltype = AA length = 10 | |
| FEATURE | Location/Qualifiers | |
| REGION | 1..10 | |
| | note = Myc tag | |
| source | 1..10 | |
| | mol_type = protein | |
| | organism = synthetic construct | |
| SEQUENCE: 27 | | |

```
EQKLISEEDL                                                          10

SEQ ID NO: 28          moltype = AA   length = 15
FEATURE                Location/Qualifiers
REGION                 1..15
                       note = S tag
source                 1..15
                       mol_type = protein
                       organism = synthetic construct
SEQUENCE: 28
KETAAAKFER QHMDS                                                    15

SEQ ID NO: 29          moltype = AA   length = 38
FEATURE                Location/Qualifiers
REGION                 1..38
                       note = SBP tag
source                 1..38
                       mol_type = protein
                       organism = synthetic construct
SEQUENCE: 29
MDEKTTGWRG GHVVEGLAGE LEQLRARLEH HPQGQREP                            38

SEQ ID NO: 30          moltype = AA   length = 13
FEATURE                Location/Qualifiers
REGION                 1..13
                       note = Softag 1
source                 1..13
                       mol_type = protein
                       organism = synthetic construct
SEQUENCE: 30
SLAELLNAGL GGS                                                      13

SEQ ID NO: 31          moltype = AA   length = 8
FEATURE                Location/Qualifiers
REGION                 1..8
                       note = Softag 3
source                 1..8
                       mol_type = protein
                       organism = synthetic construct
SEQUENCE: 31
TQDPSRVG                                                            8

SEQ ID NO: 32          moltype = AA   length = 14
FEATURE                Location/Qualifiers
REGION                 1..14
                       note = V5 tag
source                 1..14
                       mol_type = protein
                       organism = synthetic construct
SEQUENCE: 32
GKPIPNPLLG LDST                                                     14

SEQ ID NO: 33          moltype = AA   length = 8
FEATURE                Location/Qualifiers
REGION                 1..8
                       note = Xpress tag
source                 1..8
                       mol_type = protein
                       organism = synthetic construct
SEQUENCE: 33
DLYDDDDK                                                            8

SEQ ID NO: 34          moltype = AA   length = 16
FEATURE                Location/Qualifiers
REGION                 1..16
                       note = Isopeptag
source                 1..16
                       mol_type = protein
                       organism = synthetic construct
SEQUENCE: 34
TDKDMTITFT NKKDAE                                                   16

SEQ ID NO: 35          moltype = AA   length = 13
FEATURE                Location/Qualifiers
REGION                 1..13
                       note = SpyTag
source                 1..13
                       mol_type = protein
                       organism = synthetic construct
```

```
SEQUENCE: 35
AHIVMVDAYK PTK                                                                    13

SEQ ID NO: 36          moltype = AA  length = 8
FEATURE                Location/Qualifiers
REGION                 1..8
                       note = Strep-tag II
source                 1..8
                       mol_type = protein
                       organism = synthetic construct
SEQUENCE: 36
WSHPQFEK                                                                           8
```

What is claimed is:

1. A method for attaching a plurality of barcodes to a plurality of polypeptides comprising the steps of:
   1) attaching a barcode to a plurality of DNA template sequences to produce a plurality of barcoded mRNA sequences each comprising a barcode sequence and a protein coding sequence;
   2) performing reverse transcription of the barcoded mRNA sequences to produce a plurality of mRNA-cDNA hybrid sequences; and
   3) performing in vitro translation of the mRNA-cDNA hybrid sequences to generate a plurality of protein-ribosome-mRNA-cDNA complexes.

2. The method of claim 1, wherein the step 1) is performed using PCR and in vitro transcription.

3. The method of claim 1, wherein the plurality of protein-ribosome-mRNA-cDNA complexes are formed by in vitro translation and ribosome stalling.

4. The method of claim 1, wherein the plurality of DNA template sequences are synthesized in parallel on an immobilized support or individually synthesized as a mixture of random sequences on a support.

5. The method of claim 1, wherein each of the steps is performed in a single container, and a correlation between a barcoding sequence and a protein sequence is determined using massively parallel DNA sequencing.

6. The method of claim 1, wherein each of the barcoded mRNA sequences contains a polymerase promoter, and the mRNA sequences are synthesized from barcoded DNA templates by in vitro transcription in a single container.

7. The method of claim 1, wherein the reverse transcription is performed using universal primers, and the cDNA sequences are complementary upstream to a ribosome binding site of the barcoded mRNA sequences.

8. The method of claim 1, wherein ribosomes stall at the 3' end of the mRNA-cDNA hybrid sequences during in vitro translation due to one or both of a lack of stop codons or the presence of ribosome stalling peptide sequences.

9. The method of claim 1, wherein primers for cDNA synthesis contain one or both of 5' desthiobiotin modifications and 5' acrydite modifications.

10. The method of claim 1, wherein the protein-ribosome-mRNA-cDNA complexes are purified using a protein affinity tag and a cDNA desthiobiotin tag.

* * * * *